US008741292B2

(12) United States Patent
Beguin et al.

(10) Patent No.: US 8,741,292 B2
(45) Date of Patent: Jun. 3, 2014

(54) PROTEINS AND METHODS FOR MODULATING CELL ACTIVITY

(75) Inventors: Pascal Beguin, Singapore (SG); Walter Hunziker, Singapore (SG)

(73) Assignee: Agency for Science, Technology and Research, Connexis (SG)

( * ) Notice: Subject to any disclaimer, the term of this patent is extended or adjusted under 35 U.S.C. 154(b) by 26 days.

(21) Appl. No.: 12/735,420

(22) PCT Filed: Jan. 14, 2009

(86) PCT No.: PCT/SG2009/000024
§ 371 (c)(1), (2), (4) Date: Jul. 14, 2010

(87) PCT Pub. No.: WO2009/091341
PCT Pub. Date: Jul. 23, 2009

(65) Prior Publication Data
US 2011/0091464 A1    Apr. 21, 2011

Related U.S. Application Data

(60) Provisional application No. 61/011,292, filed on Jan. 15, 2008.

(51) Int. Cl.
*A61K 39/395* (2006.01)
*C07K 16/18* (2006.01)

(52) U.S. Cl.
USPC ................ 424/139.1; 424/130.1; 530/387.1; 530/387.9

(58) Field of Classification Search
None
See application file for complete search history.

(56) References Cited

FOREIGN PATENT DOCUMENTS

EP          1396543 A2     3/2004

OTHER PUBLICATIONS

Wells, J.A. (1990). Additivity of mutational effects in proteins. Biochemistry. 29(37):8509-8517.*
Ngo et al. (1994). Computational complexity, protein structure prediction, and the Levinthal paradox. In Merz and Le Grand (Eds.) The Protein Folding Problem and Tertiary Structure Prediction. Birkhauser:Boston, pp. 491-495.*
MacFarlane et al. (2009). European Journal of Pharmacology. 625:101-107.*
http://ibis.internal.epo.org/exam/dbfetch.jsp?id-EM_HTG:BC025527 printed on May 14,2012, citing "Mus musculus IN080 complex subunit E, mRNA (cDNA clone Image: 5323944), with apparent retainer intron". Proc. Natl. Acad. Sci. USA 99(26): 16899-16903 (2002).
http://ibis.internal.epo.org/exam/dbfetch.jsp?id-EM_RO:BC079045 printed on May 14, 2012 citing "Rattus norvegicus coiled-coil domain containing 95, mRNA (cDNA clone MGC: 93981 Image: 7115071), complete cds.", Proc. Natl. Acad. Sci. USA 99(26): 16899-16903 (2002).
http://ibis.internal.epo.org/exam/dbfetch. jsp?id=UNIPROT:Q6AYH2 printed on May 14, 2012 citing "RecName: Full=IN080 complex subunit E; AltName: Full=coiled-coil domain-containing protein 95;", Genome Res 14:2121-2127 (2004).
"The Status, Quality, and Expansion of the NIH Full-Length cDNA Project: The Mammalian Gene Collection (MGC)" http://www.genome.org/egl/dol/10.1101/gr 2596504, Cold Spring Harbor Laboratory Press ISSN 1088-9051/04, 2004.
Mahalaksmi, Ramasubbu N., "Nuclear Localization of Endogenous RGK Proteins and Modulation of Cell Shape Remodeling by Regulated Nuclear Transport", Traffic 2007; 8: pp. 1164-1178, 2007.
Mahalakshmi, Ramasubbu N., "Nuclear Transport of Kir/Gem Requires Specific Signals and Importin α5 and is Regulated by Calmodulin and Predicted Serine Phosphorylations", Traffic 2007:8 pp. 1150-1163, 2007.
Jin, Jingji, et al., "A Mammalian Chromatin Remodeling Complex with Similarities to the Yeast INO80 Complex", The Journal of Biological Chemistry vol. 280, No. 50, pp. 41207-4121, Dec. 16, 2005.
Mahalakshmi, R.N., "A regulatory role for Kir/Gem and the novel muscle-specific protein CCDC95 in myogenesis", IMCB Symposium 2008, Abstract 34, Aug. 13, 2008.
Extended European Search for EP Patent Application No. 09702757. 7-2406/2244725, PCT/SG2009000024, May 31, 2012.

* cited by examiner

*Primary Examiner* — Christine J Saoud
*Assistant Examiner* — Jon M Lockard
(74) *Attorney, Agent, or Firm* — MKG, LLC

(57) ABSTRACT

The present invention relates to a novel gene encoding a protein termed Coiled Coil Domain Containing 95 (CCDC95) or a peptide fragments thereof. The present invention also relates to the use of CCDC95 in Modulation of RGK small binding protein via altering concentration or sub-cellular localization of RGK small binding protein with CCDC95 or a peptide fragments thereof.

4 Claims, 21 Drawing Sheets

A
```
        1                                                                          70
human  MNGPADGEVDYKKKYRNLKRKLKFLIYEHECFQEELRKAQRKLLKVSRDKSFLLDRLLQYENVDEDSSDS
rat    -----
mouse  -----
drosophila --A--T-F-ER-K---K--------N-Y--DL--HTN--R------RT-------V--KPAK----

71                                                                         140
human  DATASSDNSETEGTPKLSDTPAPKRKRSPPLGGAPSPSSLSLPPSTGFPLQASGVPSPYLSSLASSRYPP
rat    ------------------------------M---------------S-----T--A----------PP---
mouse  ------------------------------M--V----------------T--A----------PP---

141                                                                        210
human  FPSDYLALQLPEPSPLRPKREKRPRLPRKLKMAVGPPDCPVGGPLTFPGRGSGAGVGTTLTPLPPPKMPP
rat    --------------------L-------------------------A--A-----S--AA-----------
mouse  --------------------L------------S------------A--A-----S--AA-----------

211              244
human  PTILSTVPRQMFSDAGSGDDALDGDDDLVIDIPE
rat    H-------Q-------------------------
mouse  H-------Q-------------------------
```

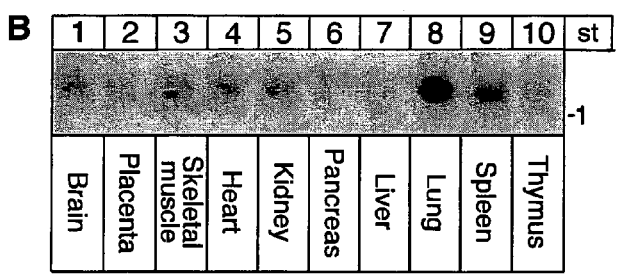

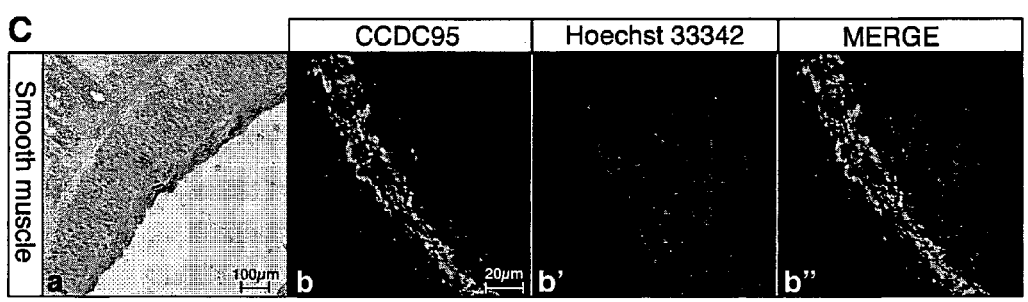

*Fig. 1*

SEQUENCE LISTING

<160> NUMBER OF SEQ ID NOS: 8

<210> SEQ ID NO 1
<211> LENGTH: 1216
<212> TYPE: DNA
<213> ORGANISM: Homo sapiens
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (1077)..(1077)
<223> OTHER INFORMATION: n is a, c, g, or t

<400> SEQUENCE: 1

```
antttcggca cagggcgtct ccggaagtgg aggcgggagc ggcacggcag ccactgcttg      60
gggtagcggg agggcagact ctgggcgcca ctcccgggcc ggtcatgaac gggccggcgg     120
acggcgaagt ggactacaaa aaaaaatacc ggaatctgaa gcggaagctc aagttcctca     180
tctacgagca cgagtgcttc caggaggagc tgaggaaagc gcaaaggaaa ttactgaagg     240
tgtcccggga caagagtttc ctcctagacc gacttctgca gtacgagaac gtggatgaag     300
actcttcgga ctcagatgcc actgcatcat cagataacag cgagacggag gggacaccca     360
agttgtctga cacaccggcc cctaagagga agagaagccc tccgctgggg ggcgccccct     420
ctccctccag cctctccctg cctccttcaa cagggtttcc ccttcaggcc tccggggtcc     480
cctccccata cctgagctcg ctggcctcct cccgctaccc cccattccct tctgactacc     540
```

-continued

```
tggccctgca gctgcccgag cccagtcccc tgaggcccaa gcgggagaaa cggccccgcc      600
tgccccggaa actcaagatg gcggtgggac cccccgactg ccctgtggga gggccgctga      660
ccttccctgg ccggggttct ggggctgggg tcgggacaac cctgaccccc ctcccacccc      720
ctaagatgcc ccccccacg atcctgagca cggtccctcg gcagatgttc agcgatgcag       780
gtagcgggga cgatgccttg gatggagacg atgacctggt gatcgacatc ccggagtgac      840
cgtgacatca cgccatgccc accacggccc gcccggcgc cctccccgtg ccagcacaca       900
cgagtccagc ttcctcggag gtgtttattg atgcccagct gccatgctcc ggccactgac      960
acaaccagaa aaggcgtaaa catgcacggg tgtcccccag gagggtggca ggggccctgc     1020
cttcaaaccc cggccccctc caggggacag ttatttaaac gagtggccgg gagcatntgc     1080
cacctgctgg ggaggcagag accctgcaat ggccacctct ttaaaagggc agctgtacag     1140
ggctaggttt tttcaatgaa gtttctgtat taaaggagtg gctctggaaa aaaaaaaaa      1200 aaaaaaaaaa aaaaa                                                      1216
```

<210> SEQ ID NO 2
<211> LENGTH: 244
<212> TYPE: PRT
<213> ORGANISM: Homo sapiens

<400> SEQUENCE: 2

```
Met Asn Gly Pro Ala Asp Gly Glu Val Asp Tyr Lys Lys Lys Tyr Arg
1               5                   10                  15

Asn Leu Lys Arg Lys Leu Lys Phe Leu Ile Tyr Glu His Glu Cys Phe
            20                  25                  30

Gln Glu Glu Leu Arg Lys Ala Gln Arg Lys Leu Leu Lys Val Ser Arg
        35                  40                  45

Asp Lys Ser Phe Leu Leu Asp Arg Leu Leu Gln Tyr Glu Asn Val Asp
    50                  55                  60

Glu Asp Ser Ser Asp Ser Asp Ala Thr Ala Ser Ser Asp Asn Ser Glu
65                  70                  75                  80

Thr Glu Gly Thr Pro Lys Leu Ser Asp Thr Pro Ala Pro Lys Arg Lys
                85                  90                  95

Arg Ser Pro Pro Leu Gly Gly Ala Pro Ser Pro Ser Ser Leu Ser Leu
            100                 105                 110

Pro Pro Ser Thr Gly Phe Pro Leu Gln Ala Ser Gly Val Pro Ser Pro
        115                 120                 125

Tyr Leu Ser Ser Leu Ala Ser Ser Arg Tyr Pro Pro Phe Pro Ser Asp
    130                 135                 140

Tyr Leu Ala Leu Gln Leu Pro Glu Pro Ser Pro Leu Arg Pro Lys Arg
145                 150                 155                 160

Glu Lys Arg Pro Arg Leu Pro Arg Lys Leu Lys Met Ala Val Gly Pro
                165                 170                 175

Pro Asp Cys Pro Val Gly Gly Pro Leu Thr Phe Pro Gly Arg Gly Ser
            180                 185                 190

Gly Ala Gly Val Gly Thr Thr Leu Thr Pro Leu Pro Pro Lys Met
        195                 200                 205

Pro Pro Pro Thr Ile Leu Ser Thr Val Pro Arg Gln Met Phe Ser Asp
    210                 215                 220

Ala Gly Ser Gly Asp Asp Ala Leu Asp Gly Asp Asp Leu Val Ile
225                 230                 235                 240

Asp Ile Pro Glu
```

```
<210> SEQ ID NO 3
<211> LENGTH: 2030
<212> TYPE: DNA
<213> ORGANISM: Mus musculus

<400> SEQUENCE: 3
gtctccggaa gtggaggtgt gagaggccgg gcggacttgg gtagcgggac tctactccgg      60
ggcgtttctc cctggcgggt catgaacgga ccagcggacg gcgaagtgga ctacaaaaag     120
aaatacagga atctgaagcg gaagctcaag ttcctcattt acgagcacga gtgcttccag     180
gaggagctca gaaaggcgca aaggaaattg ctgaaggttt cccgagacaa gagtttcctt     240
ctagatcgac ttctgcagta tgagaacgtg gatgaagact cctctgattc agatgccacc     300
gcatcttcag ataacagtga gacagagggg acacccaagt gtctgacacg ccagcccct     360
aagaggaaga gaagcccccc catgggaggt gtcccatccc cttccagcct ctccttgcct     420
ccttcaacag gctttcccct gcagacttct ggggccccct ccccatacct gagctcgctg     480
gcttctcccc cttacccccc attcccttct gactacctgg ccctgcagct gcctgagccc     540
agcccctga ggcccaagct ggagaaacgg ccccgcctac cccggaaact caagatgtcg     600
gttggacccc ctgactgccc cgtgggtggg ccgctggctt tccagccag gggttctggt     660
gccagtgttg gggcagccct gaccccctg cctcctccca agatgcctcc acatacaatc     720
ctgagcaccg tccctcagca gatgttcagc gatgcaggca gtggggatga cgccctggac     780
ggagatgacg acctggtgat cgacattcca gagtagccac ccagtgccac ctgccaggca     840
cctcacagca ctcctcctgt gccagcaaac tcaagcccac ttcctcaaga gatgtttatt     900
gatgcccagt tgccatgctt cggccactga cacaatcaga aaaggcgtaa acatgcacaa     960
tgtccccgag gaaggtggca gggtcctgcc cttacatccc agcccatcc agggaacagt    1020
tatttaaacg agtggccaaa agggtctgct acatcttcgg gaggtagaga cctacggtgg    1080
ccgcccttt agaagagcag ctacgcaggg ctgggattta gtgaaggctc tgtattaaag    1140
agttggctct ttctttcctt gtcctttcct ctatttggaa acgtcctcct ctaatcttcc    1200
ctaatccgac cccctccctg tggggcaggg accaggcag cctggaaagg ccaagaaagg    1260
agctgcagga tggggtgggg cactggcagg agactccac gtggccctgt gcacgggtgg    1320
ttgcatattt gcaggtaaca gcaaggcagg caggaggaag tttgcatatg tgaatatagc    1380
tctccacagt ccctcacaag aagacaggcc cgtcacagag actcacaaaa ataagacagg    1440
tagtgtgggg caggggcatc ccaccccatg taaacgtgca acacactcgt gcgaaggttg    1500
ggtactggac ccggccccag agggcctgtg atggacagct gctgttcact caagccaaag    1560
ggtaagcccc tgctgcaggg ggcagctcgc tggtcagagt atgccagcgc tccagggctg    1620
tgtccggctg atgtagacag tcattccagt gtttctgggc ctctcccgg gctcctggcc    1680
ccagagacac accacctgaa gaacaggcaa ggcaggccaa cgtgtcagcg cccactctcc    1740
tccacttccc tcagagcacc tggtgggctc tgccactcac ctatgaagtc attggatttg    1800
ccaatgtcgt agtcccagac tgtgacctcc agggtcttag tggccagagt ggagagttca    1860
atctcataga agaattcctg agaacaaagg caggcggtgc tttctgtgag gcctaaccac    1920
atcgctgtcc ccagcccaac tttatttcta ctccctgaca ttttaacctc attaaattcc    1980
ggatttagtt cttcttcttt acacatgttt tgtgcttgga tttcttatcc               2030

<210> SEQ ID NO 4
<211> LENGTH: 244
<212> TYPE: PRT
<213> ORGANISM: Mus musculus
```

-continued

<400> SEQUENCE: 4

| | | | | | | | | | | | | | | |
|---|---|---|---|---|---|---|---|---|---|---|---|---|---|---|
|Met|Asn|Gly|Pro|Ala|Asp|Gly|Glu|Val|Asp|Tyr|Lys|Lys|Lys|Tyr|Arg|
|1| | | |5| | | |10| | | | |15| | |

Asn Leu Lys Arg Lys Leu Lys Phe Leu Ile Tyr Glu His Glu Cys Phe
         20              25             30

Gln Glu Glu Leu Arg Lys Ala Gln Arg Lys Leu Leu Lys Val Ser Arg
     35              40              45

Asp Lys Ser Phe Leu Leu Asp Arg Leu Leu Gln Tyr Glu Asn Val Asp
       50              55              60

Glu Asp Ser Ser Asp Ser Asp Ala Thr Ala Ser Ser Asp Asn Ser Glu
65               70              75            80

Thr Glu Gly Thr Pro Lys Leu Ser Asp Thr Pro Ala Pro Lys Arg Lys
             85              90            95

Arg Ser Pro Pro Met Gly Gly Ala Pro Ser Pro Ser Ser Leu Ser Leu
         100             105           110

Pro Pro Ser Ser Gly Phe Pro Leu Gln Thr Ser Gly Ala Pro Ser Pro
        115            120           125

Tyr Leu Ser Ser Leu Ala Ser Pro Pro Tyr Pro Phe Pro Ser Asp
    130            135            140

Tyr Leu Ala Leu Gln Leu Pro Glu Pro Ser Pro Leu Arg Pro Lys Leu
145            150             155          160

Glu Lys Arg Pro Arg Leu Pro Arg Lys Leu Lys Met Ala Val Gly Pro
         165            170           175

Pro Asp Cys Pro Val Gly Gly Pro Leu Ala Phe Pro Ala Arg Gly Ser
        180            185           190

Gly Ala Ser Val Gly Ala Ala Leu Thr Pro Leu Pro Pro Lys Met
    195            200           205

Pro Pro His Thr Ile Leu Ser Thr Val Pro Gln Gln Met Phe Ser Asp
        210            215           220

Ala Gly Ser Gly Asp Asp Ala Leu Asp Gly Asp Asp Leu Val Ile
225            230             235          240

Asp Ile Pro Glu

<210> SEQ ID NO 5
<211> LENGTH: 2073
<212> TYPE: DNA
<213> ORGANISM: Rattus rattus

<400> SEQUENCE: 5

```
ccggaagtgg agggtgtgt gcgtgtgtgt atgtgtgtgt gtgtgtgtgt gtgtgagaga      60
gagaggacgg gcggacttgg gtagcgggac tctactccgg ggcgcttctc ccaggcgggt    120
catgaacgga ccagcggacg gcgaagtgga ctacaaaaag aaatacagga atctgaagcg    180
gaagctcaag ttcctcattt acgaacacga gtgcttccag gaggagctca ggaaggcgca    240
aagaaaattg ctgaaggttt cccgagacaa gagtttcctt ctagatcgac ttctgcagta    300
tgagaacgtg gatgaagact cttccgattc agatgccact gcgtcttcag acaacagtga    360
gaccgaaggg acgcccaagt tgtcggacac accagcccct aagaggaaga agcccccc     420
gatgggaggt gccccatccc cttccagcct ctcattgcct ccttcatcag gatttccccct    480
gcagacttct ggggcccct ccccatacct gagctcgctg gcttctcccc cttaccccc     540
attcccttct gactacctgg ccctgcagct gcctgagccc agcccctga ggccaagct      600
ggagaaacgg ccccgcctac cccggaaact caagatggcg gtgggccccc ctgactgccc    660
```

```
tgtgggtgga ccgctggctt tccctgccag gggttctggt gccagtgttg gggcagctct      720
gacccccctg cctcctccca agatgcctcc acatacaatc ctgagcaccg tccctcagca      780
gatgttcagc gatgccggca gcggagatga tgccctagac ggagatgatg acctggtgat      840
cgacatcccg gagtagccac tcagtgctac ctgccaggca ccccgcccag tgctcctcct      900
gagccagcac actgagccca cttcctcaag agatgtttat tgatgcccag ttgccatgct      960
tcggccactg acacaatcag aaaaggcgta acatgcaca aatgtccccg aggaaggtgg      1020
caggggccct gcccttacac ccaccccat cctgggaaca attatttaat gagtggccaa      1080
aagggtctgc tacatcttag gaaggtagag acccttggtg gccgcccctt tagaagagca      1140
gctgcgcagg gctgggacat tttaatgaag gctctgtatt aaagagttgg ctctttcttt      1200
ccttatcctt tcctctattt ggaaatgtcc tcctctaatc tcccctaatc ccacccctc       1260
cttgtggggc aggggaccag gcagcctgga gaggccaaga gaggagctgc aggattgggt      1320
ggggcactgg caggagactc ccacgtagcc ctgtgcatgg ggtggttgca tatttgcagg      1380
taagagcaag tcaggcagga ggaagtttgc atatgtgaat atagctctcc acatccctca      1440
caagaagata gacccacggt cacagagact cacaaaaata agacaggtag tgtggggcag      1500
gggcgtccca cccatgtaaa cgtgcaacac actcgtgcga aggttgggta ctggacccgg      1560
ccgcagaggg cctgtgctgg gcagctgcag tctgttcagg ccaacggcaa cgcccctgct      1620
gctgggggca gctcgctggt cagggtatgc cagcgctcca ctgctgtgtc cggctgatgt      1680
agacagtctc tccagtgttt ctgggcctct ccccggctc ctggccccag agacacacca       1740
cctgaagaac aggcaaggca ggccaacctg tcagtgccca ctctcttcca cttccctgac      1800
acctggtgga ctcctccact cacctatgaa gtcattggat ttgccaatgt cgtagtccca      1860
gactgtgact tccagggtct tggtagccag agtggagagt tccatctcat aaaagaattc      1920
ctgagaacaa ggcaggaggt gctttctgag agaccttctc acattgctct ccccagacca      1980
tcttgatttc tgctccctgc cattttttacc tcattaaatt ccgggttcag cgtcttcttc      2040
tttaaaaaaa aaaaaaaaaa aaaaaaaaaa aaa                                   2073
```

<210> SEQ ID NO 6
<211> LENGTH: 244
<212> TYPE: PRT
<213> ORGANISM: Rattus rattus

<400> SEQUENCE: 6

```
Met Asn Gly Pro Ala Asp Gly Glu Val Asp Tyr Lys Lys Lys Tyr Arg
1               5                   10                  15

Asn Leu Lys Arg Lys Leu Lys Phe Leu Ile Tyr Glu His Glu Cys Phe
            20                  25                  30

Gln Glu Glu Leu Arg Lys Ala Gln Arg Lys Leu Leu Lys Val Ser Arg
        35                  40                  45

Asp Lys Ser Phe Leu Leu Asp Arg Leu Leu Gln Tyr Glu Asn Val Asp
    50                  55                  60

Glu Asp Ser Ser Asp Ser Asp Ala Thr Ala Ser Ser Asp Asn Ser Glu
65                  70                  75                  80

Thr Glu Gly Thr Pro Lys Leu Ser Asp Thr Pro Ala Pro Lys Arg Lys
                85                  90                  95

Arg Ser Pro Pro Met Gly Gly Ala Pro Ser Pro Ser Ser Leu Ser Leu
            100                 105                 110

Pro Pro Ser Ser Gly Phe Pro Leu Gln Thr Ser Gly Ala Pro Ser Pro
            115                 120                 125
```

```
Tyr Leu Ser Ser Leu Ala Ser Pro Pro Tyr Pro Pro Phe Pro Ser Asp
    130                 135                 140

Tyr Leu Ala Leu Gln Leu Pro Glu Pro Ser Pro Leu Arg Pro Lys Leu
145                 150                 155                 160

Glu Lys Arg Pro Arg Leu Pro Arg Lys Leu Lys Met Ala Val Gly Pro
                165                 170                 175

Pro Asp Cys Pro Val Gly Gly Pro Leu Ala Phe Pro Ala Arg Gly Ser
            180                 185                 190

Gly Ala Ser Val Gly Ala Ala Leu Thr Pro Leu Pro Pro Pro Lys Met
        195                 200                 205

Pro Pro His Thr Ile Leu Ser Thr Val Pro Gln Gln Met Phe Ser Asp
    210                 215                 220

Ala Gly Ser Gly Asp Asp Ala Leu Asp Gly Asp Asp Asp Leu Val Ile
225                 230                 235                 240

Asp Ile Pro Glu

<210> SEQ ID NO 7
<211> LENGTH: 29
<212> TYPE: DNA
<213> ORGANISM: Artificial
<220> FEATURE:
<223> OTHER INFORMATION: Origene construct TI100126

<400> SEQUENCE: 7
aagatgcctc cacatacaat cctgagcac                                     29

<210> SEQ ID NO 8
<211> LENGTH: 29
<212> TYPE: DNA
<213> ORGANISM: Artificial
<220> FEATURE:
<223> OTHER INFORMATION: Origene construct TI100128

<400> SEQUENCE: 8
gatcgacttc tgcagtatga gaacgtgga                                     29
```

PROTEINS AND METHODS FOR MODULATING CELL ACTIVITY

CROSS-REFERENCE TO RELATED APPLICATION

This application is a U.S. National Stage Application of International No. PCT/SG2009/000024, which claims benefit of, and priority from, U.S. provisional patent application No. 61/011,292 filed on 15 Jan. 2008, the contents of both applications are fully incorporated herein by reference.

FIELD OF THE INVENTION

The present invention provides a method for modulating the activity of Voltage Gated Calcium Channels (VGCC) in a cell. In particular, the invention provided methods for modulating VGCC associated diseases (including ataxia, migraine, epilepsy, neurodegeneration, hypertension, cardiac disorders and diabetes) by up- or downregulation of CCDC95 and or its interaction with RGK proteins.

The present invention also relates to a method of modulating myogenesis through regulation of CCDC95 and or its interaction with RGK proteins which interaction can be used to regulate calcium channel activity, actin and microtubule dynamics which effect cell shape and cell differentiation among other activities.

BACKGROUND

The Ras superfamily of GTPases comprises the Ras, Rho, Rab, Arf and Ran subfamilies (Colicelli, 2004 *Sci. STKE.* 2004:RE13.). Within the Ras subfamily, the RGK family includes four members, Rad (Reynet and Kahn, 1993 *Science.* 262:1441-4), Rem (Finlin and Andres, 1997 *Mol. Biol. Cell.* 9:1449-63), Rem2 (Béguin et al., 2005, *Biochem. J.* 390:67-75) and Kir/Gem (Cohen et al., 1994 *Proc. Natl. Acad. Sci. U.S.A.* 91:12448-52). RGK small GTP-binding proteins regulate cellular processes as diverse as voltage gated calcium channel (VGCC) activity (Béguin et al., 2006 *J. Mol. Biol.* 355:34-46) and actin and microtubule dynamics (Pelosi et al., 2007 *Mol. Cell. Biol.* 27:6163-76).

Kir/Gem, a member of the multifunctional RGK small GTP-binding protein family, regulates VGCC activity and actin and microtubule cytoskeleton remodeling. Individual functions of Kir/Gem are dependent on its subcellular distribution. Nuclear localization, for example, prevents its inhibitory effect on the Rho-Rho kinase pathway associated with changes in cell shape without affecting downregulation of VGCC activity. The subcellular distribution of Kir/Gem is modulated by calmodulin, 14-3-3 and importin binding, which in turn is regulated by phosphorylation.

Despite conserved core domains for nucleotide binding, members of the RGK family show striking structural and functional differences to other proteins within the Ras subfamily. While Ras switches between an inactive GDP-bound and an active GTP-bound conformation, unique structural features in the Ras core domain suggest an unconventional mechanism of inactivation for RGK proteins (Kelly, 2005 *Trends Cell Biol.* 15:640-3). Another distinctive feature of RGK proteins when compared to Ras is their regulation at the transcriptional level. Kir/Gem expression is induced upon transformation of cells with the abl tyrosine kinase oncogene (Cohen et al., 1994 *Proc. Natl. Acad. Sci. U.S.A.* 91:12448-52) and the stimulation of endothelial cells with IL-1α or TNFα (Warton et al., 2004 *Gene.* 342:85-95) or of peripheral T cells with mitogens (Maguire et al., 1994 *Science.* 265:241-4). Deregulation of Kir/Gem and Rad were also reported in neuroblastoma (Leone et al., 2001 *Oncogene.* 20:3217-25) and breast cancer (Tseng et al., 2001 *Cancer Res.* 61:2071-9) cell lines, respectively. The short half-life of the mRNA (~30 min) (Cohen et al., 1994 *Proc. Natl. Acad. Sci. U.S.A.* 91:12448-52) and protein (~3 hrs) (Ward et al., 2004 *Mol. Cell. Biol.* 24:651-61) suggests that RGK protein levels are tightly regulated in response to specific stimuli.

RGK proteins are multifunctional regulators of several cellular processes, including ion channel activity and cell shape remodeling. Binding of RGK proteins to the auxiliary β-subunit regulates the activity of VGCC, also known as voltage-dependent calcium channels or VDCC, either by interfering with cell surface transport of VGCCs or suppressing $Ca_{2+}$ influx at the plasma membrane.

Voltage-gated calcium channels are a major route of calcium translocation across the plasma membrane of excitable cells. Intracellular calcium plays an important role in many biological processes such as calcium dependant neurotransmitter release, hormone secretion, muscle contraction and gene expression. More specifically, it is documented that abnormal levels of intracellular calcium create an imbalance in calcium homeostasis in a variety of cells, tissues and organs leading to many disorders. The conversions of the intracellular calcium flow by voltage-gated calcium channels is thought to impact a wide spectrum of biological responses and are implicated in several diseases, including ataxia, migraine, epilepsy, neurodegeneration, hypertension, cardiac disorders and diabetes. Currently there are several Calcium channel blockers used to treat some of these conditions. Compounds such as verapamil, isradipine, nefedipine, dilantizem and 1,4-dihydropine analogs of nefedipine interact with the L-type calcium channel to block calcium translocation and are widely used as antihypertensives, migraine treatment and in the treatment of certain vascular disorders. However, there are reports that therapeutic use of many calcium channel blockers is associated with potentially life-threatening side-effects. These include hypotension, constipation, decrease in insulin secretion leading to diabetes and heart block. Other calcium cannel blockers under development for use in disorders of the central nervous system and as analgesics include toxins that have been isolated from marine snails, scorpions, funnel web and tarantula spiders. The side effects and efficacy of such compounds are as yet unknown. Only two compounds have been found to act as agonists of voltage gated calcium channels, a dihydropyridine derivative BayK 8644 and Glycerotoxin isolated from sea worms. Despite the anticipated therapeutic effects of these compounds such as stimulating insulin secretion in diabetic and pre-diabetic living beings there has been severe side effects such as dystonic neurobehavioural syndrome, hypertension and arrhythmia during in vivo studies using BayK 8644 resulting in halted development of such compounds. There is a need for new agonists and antagonists capable of modulating voltage gated calcium channels to treat disorders associated with voltage gated calcium channels.

RGK proteins also act on the microtubule and actin cytoskeleton and their overexpression induces dendrite like extensions in COS-1 cells neurite outgrowth in neuroblastoma cells (Kir/Gem) and protrusions in endothelial cells (Rem). As shown for Kir/Gem and Rad, negative regulation of the Rho pathway by direct binding to Rho kinase and the Rho activating protein Gmip may account to a large extent for the effects of RGK proteins on cell morphology. Little is known about cell morthogenisis and the factors controlling cell shape and size.

Muscle formation involves the gradual differentiation of myocytes, which eventually fuse and exit the cell cycle to form multinucleated myotubes (Taylor, 2002 *Curr. Biol.* 12:R224-8). Myf5 and MyoD are primary muscle development factors (MRFs) required for the formation of skeletal myoblasts, whereas the secondary MRFs myogenin and MRF4 act as differentiation factors at later stages (Parker et al., 2003 *Nat. Rev. Genet.* 4:497-507). Myogenic differentiation relies on the activation of several signaling cascades, including the Rho-Rho kinase pathway (Bryan et al., 2005 *Cell. Mol. Life. Sci.* 62:1547-55) and apoptotic signals leading to the activation of caspases 3 and 12 (Fernando et al., 2002 *Proc. Natl. Acad. Sci. U.S.A.* 99:11025-30).

Many heart diseases result from a deficiency in the number of cardiomyocytes. Induction of new cardiomyocytes can possibly regenerate cardiac growth and potentially be used to treat such diseases. Heart tissue is the archetypical nonregenerative organ which is apparent from the rarity of cardiomyocyte tumors. A number of approaches have been used to regenerate myocardium in experimental animals. Some of these include genetic manipulation of cardiomycytes, transplantation of skeletal myoblasts, use of donor cardiomycytes or the use of various stem cell transplants (Rubart M & Field L. J. 2006. *annu rev. Physiol.* 68:29-49). Of these methods the use of donor cardiomycytes has been most successful however there are several obstacles to the successful use of such cells in therapy. The cells do not increase in volume and may not survive transplantation further effecting the volume of these cells, it is very difficult to have sufficient numbers of donor cells and there is a lack of adequate immune suppression to efficiently minimise rejection of the cells. Further it is difficult to study differentiation of cydiomyocytes as they only represent 20% of the cells present in an adult ventrical.

RGK small GTP-binding proteins regulate cellular processes as diverse as VGCC activity (Yada et al., 2007 *Circ. Res.* 101:69-77) and actin and microtubule dynamics (Piddini et al., 2001 *EMBO J.* 20:4076-87). This results in a wide variation in subcellular distribution of RGK proteins which can translocate to the nucleus, with differential effects on RGK protein function. RGK proteins still downregulate channel activity when they localize to the nucleus, but no longer affect cell shape (Béguin et al., 2006 *J. Mol. Biol.* 355:34-46). This coupling between specific function and subcellular localization requires tight regulation, which is accomplished by posttranslational modifications and the association of regulatory factors. Nuclear localization is mediated by the association of importins with NLSs on RGK proteins. The relevance of nuclear localization is not well understood but the presence of endogenous nuclear Kir/Gem and Rem2 in primary hippocampal neurons as well as in situ in cells of the brain and heart indicate it is important.

The present invention seeks to provide novel modulators of RGK small GTP-binding proteins to vary concentration and location in a cell for use in treating disorders related to RGK small GTP-binding proteins concentration and location in a cell.

Those skilled in the art will appreciate that the invention described herein is susceptible to variations and modifications other than those specifically described. The invention includes all such variation and modifications. The invention also includes all of the steps, features, formulations and compounds referred to or indicated in the specification, individually or collectively and any and all combinations or any two or more of the steps or features.

Each document, reference, patent application or patent cited in this text is expressly incorporated herein in their entirety by reference, which means that it should be read and considered by the reader as part of this text. That the document, reference, patent application or patent cited in this text is not repeated in this text is merely for reasons of conciseness.

Any manufacturer's instructions, descriptions, product specifications, and product sheets for any products mentioned herein or in any document incorporated by reference herein, are hereby incorporated herein by reference, and may be employed in the practice of the invention.

The present invention is not to be limited in scope by any of the specific embodiments described herein. These embodiments are intended for the purpose of exemplification only. Functionally equivalent products, formulations and methods are clearly within the scope of the invention as described herein.

The invention described herein may include one or more range of values (eg size, concentration etc). A range of values will be understood to include all values within the range, including the values defining the range, and values adjacent to the range which lead to the same or substantially the same outcome as the values immediately adjacent to that value which defines the boundary to the range.

Throughout this specification, unless the context requires otherwise, the word "comprise" or variations such as "comprises" or "comprising", will be understood to imply the inclusion of a stated integer or group of integers but not the exclusion of any other integer or group of integers. It is also noted that in this disclosure and particularly in the claims and/or paragraphs, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the invention.

Other definitions for selected terms used herein may be found within the detailed description of the invention and apply throughout. Unless otherwise defined, all other scientific and technical terms used herein have the same meaning as commonly understood to one of ordinary skill in the art to which the invention belongs.

SUMMARY OF THE INVENTION

We have identified a novel protein, CCDC95, predominantly expressed in muscle cells as interacting with a RGK small GTP-binding protein. CCDC95 mediates efficient nuclear localization of Kir/Gem via importins $\alpha 6$ and $\alpha 7$, bypassing the importin $\alpha 5$-dependent pathway previously described for Kir/Gem. In a tissue culture model for muscle differentiation, Kir/Gem redistributes from the nucleus to the cytosol during early stages of differentiation. At later stages, CCDC95 expression is induced and following myocyte fusion Kir/Gem and CCDC95 are found in apoptotic nuclei of myotubes. Overexpression of Kir/Gem, but not a mutant that localizes to the nucleus, interferes with myoblast differentiation.

These results uncover a novel function for Kir/Gem in muscle development. CCDC95 likely provides temporal regulation of the subcellular distribution of Kir/Gem during late stages of myoblast differentiation.

The present invention provides a method for modulating the activity of Voltage Gated Calcium Channels (VGCC) in a cell. In particular, the invention provided methods for modulating VGCC associated diseases (including ataxia, migraine, epilepsy, neurodegeneration, hypertension, cardiac disorders and diabetes) by up- or downregulation of CCDC95 and or its interaction with RGK proteins.

The present invention also provides to a method of modulating myogenesis in a patient, which method comprises the step of regulating CCDC95 and or its interaction with Kir/Gem which interaction regulates calcium channel activity, actin and microtubule dynamics which effect cell shape and cell differentiation among other activities.

CCDC95 polypeptides of the invention may also be used in methods of identifying substances capable of affecting RGK small GTP-binding proteins function, such as substances capable of modulating RGK small GTP-binding proteins. A substance identified by these methods may be used in a method of modulating calcium channel activity, myoblast differentiation and/or cell morthology.

In a particular embodiment, there is provided a method for screening the CCDC95 gene to identify mutations such as those that cause haploinsufficiency. To detect haploinsufficient CCDC95 gene mutations, a biological sample is preferably prepared and analysed for a difference between the sequence of the CCDC95 gene being analysed and the sequence of the wild-type CCDC95 gene. Mutant CCDC95 genes can be identified by any of the techniques described herein. The mutant alleles can then be sequenced to identify the specific mutation of the particular mutant allele.

Alternatively, mutant CCDC95 genes can be identified by detecting mutant (altered) CCDC95 proteins, using conventional techniques. The mutant genes are then sequenced to identify the specific mutation for each gene. The mutations, especially those that lead to an altered function of the CCDC95 protein, may then be used for the diagnostic and prognostic methods of the present invention.

The present invention also provides kits for screening patients that might be susceptible to disorders related to RGK small GTP-binding proteins, which ailments are linked to mutations in one or both CCDC95 alleles, for example a mutation resulting in haploinsufficiency of the CCDC95 gene, which kits comprise at least a polynucleotide complementary to the portion of the CCDC95 gene packaged in a suitable container, and instructions for its use to identify the CCDC95, which instructions also include a sequence listing of the complete or a substantially complete CCDC95 gene sequence that is capably of encoding a functional CCDC95 polypeptide sequence in a patient that is not suffering from the specified ailments.

The present invention also provides kits for screening patients to confirm and or identify that they are afflicted with disorders related to RGK small GTP-binding proteins which ailments are linked to haploinsufficiency of the CCDC95 gene, which kits comprise at least a polynucleotide complementary to the portion of the CCDC95 gene packaged in a suitable container, and instructions for its use to identify the CCDC95, which instructions also include a sequence listing of the complete or a substantially complete CCDC95 gene sequence that is capably of encoding a functional CCDC95 polypeptide sequence in a patient that is not suffering from the specified ailments.

In addition, the present invention provides methods of screening drugs for CCDC95 gene therapy to identify suitable drugs for restoring or blocking CCDC95 gene product function.

The present invention also provides the means necessary for production of gene-based therapies directed at CCDC95 genes in cells. These therapeutic agents may take the form of polynucleotides comprising all or a portion of the CCDC95 gene placed in appropriate vectors or delivered to target cells in more direct ways such that the function of the CCDC95 gene protein is reconstituted or blocked. Therapeutic agents may also take the form of polypeptides based on either a portion of, or the entire protein sequence of CCDC95 gene. These may functionally replace or block the activity of CCDC95 gene in vivo.

In a further aspect, the present invention provides a method of modulating a RGK small GTP-binding proteins comprising the step of varying the concentration of CCDC95 polypeptide or varying the concentration or subcellular location of peptide fragments of CCDC95 polypeptide.

In a further aspect, the present invention provides a composition for modulating a RGK small GTP-binding proteins comprising a CCDC95 polypeptide, CCDC95 mutants or CCDC95 peptide fragments.

Another aspect of the invention provides a system or kit for modulating the activity of RGK small GTP-binding proteins, the system comprising: a composition comprising a CCDC95 polypeptide or a peptide fragment of CCDC95, and a delivery agent.

Another aspect of the invention provides a method of directing stem cell differentiation comprising varying the concentration or subcellular location of a CCDC95 polypeptide. Preferably the stem cell is a myoblast.

The invention has a wide spectrum of useful applications The CCDC95 gene sequences and proteins described herein may be used in diagnostic/prognostic, therapeutic cell manipulation and drug screening methods described herein for a wide range of species. Further, probes and primers based on the CCDC95 gene sequences disclosed herein may be used to identify homologous CCDC95 gene sequences and proteins in other species.

A Amino acid sequences of human, rat and mouse CCDC95, Amino acids are shown in the one-letter code and residues conserved between species are indicated with a dashed line. The coiled-coil domain of CCDC95 is depicted by shading. The amino acid sequence of the coiled-coil domain of the fly orthologue is also shown.

B Northern blot analysis of CCDC95 expression in human tissues.

C and D Immunolocalization of CCDC95 in smooth muscle and heart. Mouse smooth muscle cryosections (C) were analyzed by immunohistochemistry (panel a) or confocal immunofluorescence microscopy (panel b and b") using CCDC95 antibodies. Nuclei were stained with Hoechst nuclear dye (blue, panel b'). Confocal immunofluorescence microscopy of mouse heart cryosections and primary cardiomyocytes (D) co-stained for CCDC95 (red) and cardiac troponin T (green) antibody. Areas of colocalization are in yellow in the merged image. Immunohistochemistry of heart using CCDC95 antibodies (panel a).

E Overexpressed CCDC95 localizes to the nucleus. COS-1 and H9c2 cardiomyocyte cells were transfected with the CCDC95 cDNA of processed for immunofluorescence microscopy. Areas of colocalization are in cyan in the merged image.

Figure 2:
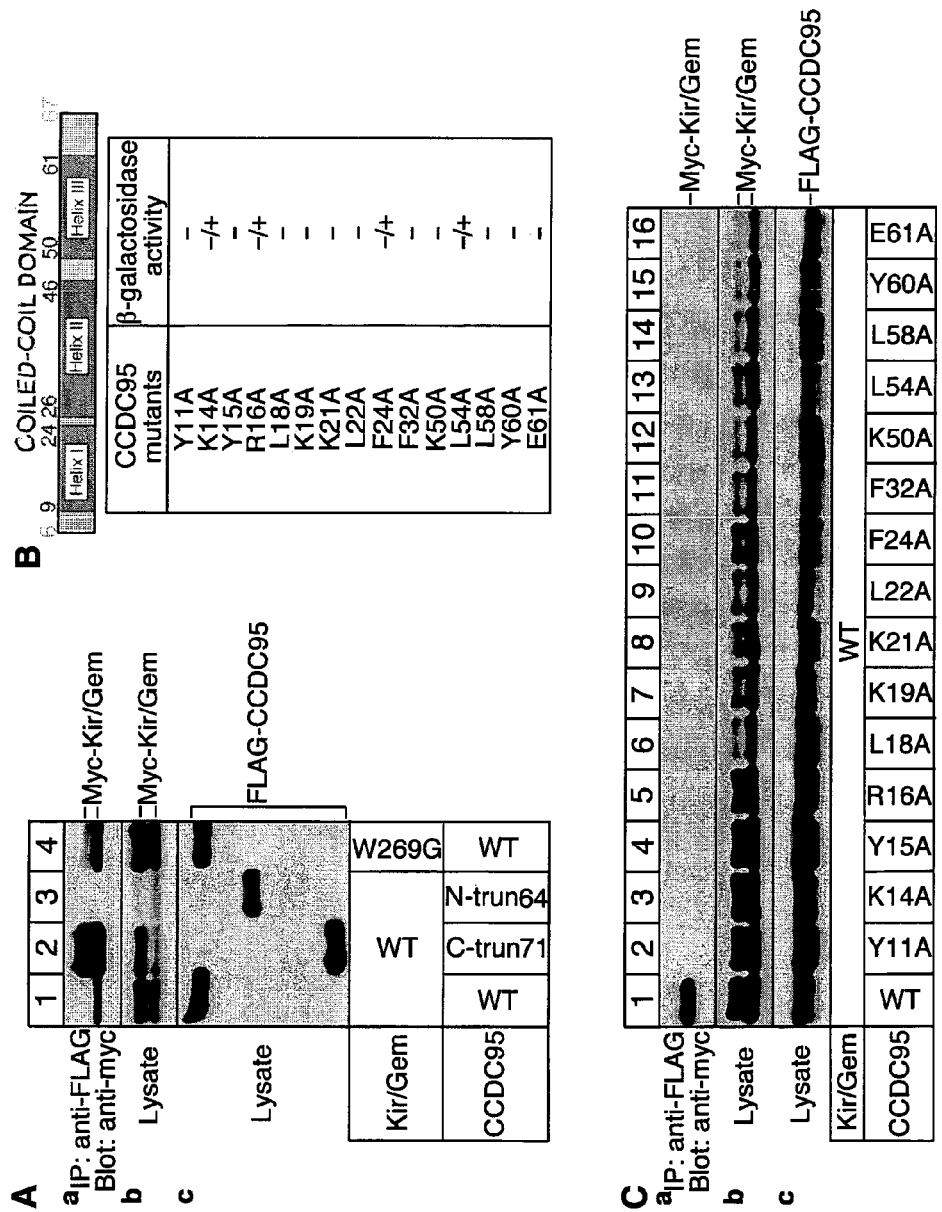
Figure 2:
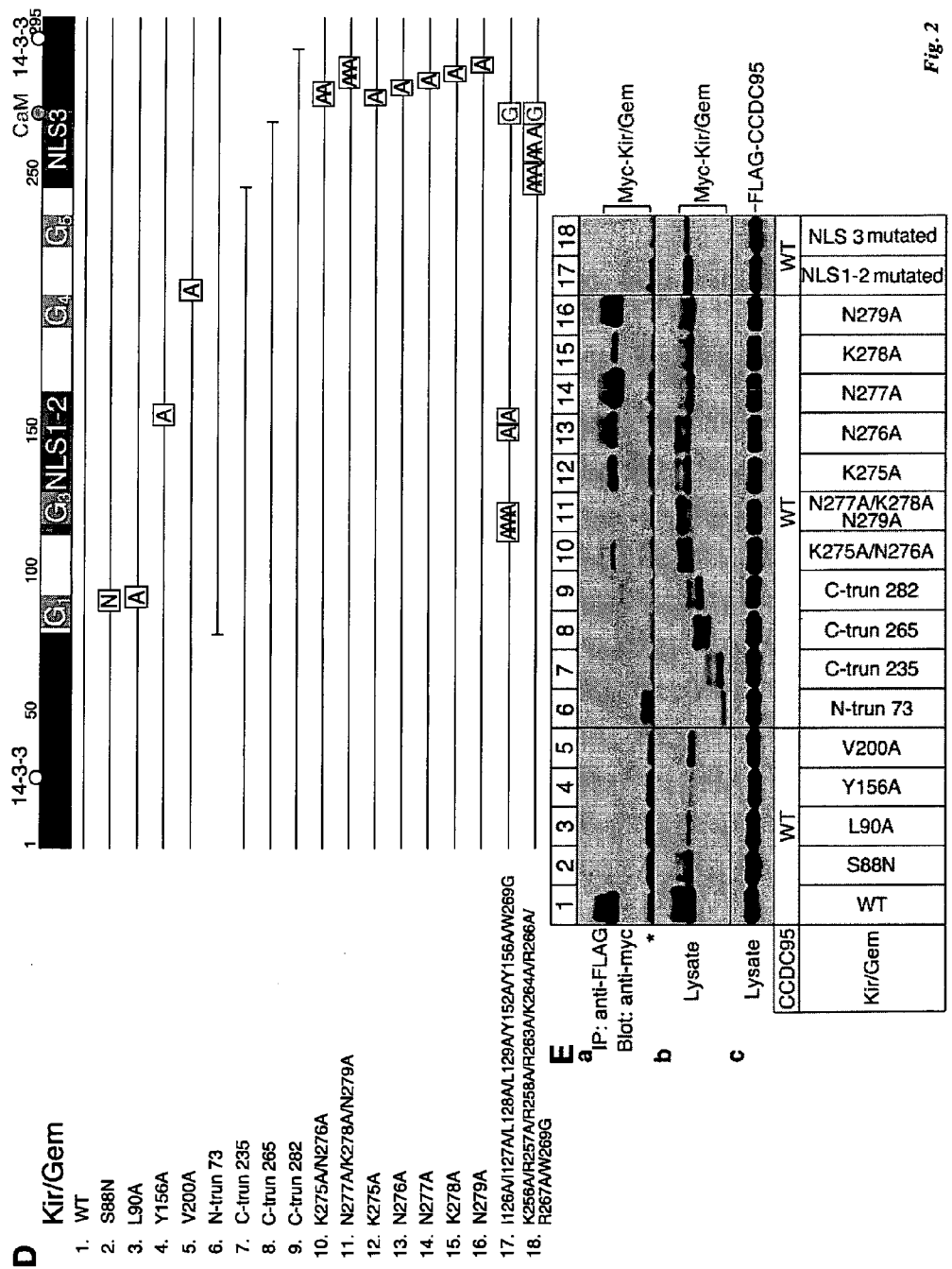

FIG. 2. Association of CCDC95 and Kir/Gem and mapping of the interacting domains.

A Coimmunoprecipitation of CCDC95 and Kir/Gem. (a) Cells were cotransfected with cDNAs for WT Myc-Kir/Gem or a mutant (W269G) defective in CaM binding and WT or truncated forms of FLAG-CCDC95. CCDC95 was then immunoprecipitated and associated Kir/Gem detected by Western blot using antibodies to the different tags. (b and c)

Cell lysates were blotted with antibodies to CCDC95 Myc (b) or FLAG (c) to monitor Kir/Gem and CCDC95 expression levels, respectively.

B and C Identification of residues in CCDC95 important for Kir/Gem binding. (B) List of the individual residues in CCDC95, which when substituted to Ala showed a reduced (−/+) or no (−) binding to Kir/Gem in a Y2H assay. (C) Coimmunoprecipitation of CCDC95 and Kir/Gem. (a) Cells were cotransfected with cDNAs for Myc-Kir/Gem and WT or mutated FLAG-CCDC95. CCDC95 was then immunoprecipitated and associated Kir/Gem was detected by Western blot using antibodies to the different tags. (b and c) Cell lysates were blotted with antibodies to Myc (b) or FLAG (c) to monitor Kir/Gem and CCDC95 expression levels, respectively.

D and E Identification of residues in Kir/Gem important for CCDC95 binding. (D) Schematic representation of Kir/Gem and the mutants used in this study. The Ras-like core domain (white), N- and C-terminal extensions (black), the location of the G1-G5 motifs involved in GTP binding (gray), NLS1-3 (blue) and the binding sites for 14-3-3 (white circles) and CaM (red circle) in Kir/Gem are indicated. N and C-terminal truncations (N-trun and C-trun) and amino acid substitutions are indicated. (E) Coimmunoprecipitation of CCDC95 and Kir/Gem. (a) Cells were cotransfected with cDNAs for FLAG-CCDC95 and WT or mutated Myc-Kir/Gem. CCDC95 was then immunoprecipitated and associated Kir/Gem was detected by Western blot using antibodies to the different tags. (b and c) Cell lysates were blotted with antibodies to Myc (b) or FLAG (c) to monitor Kir/Gem and CCDC95 expression levels, respectively.

Figure 3:
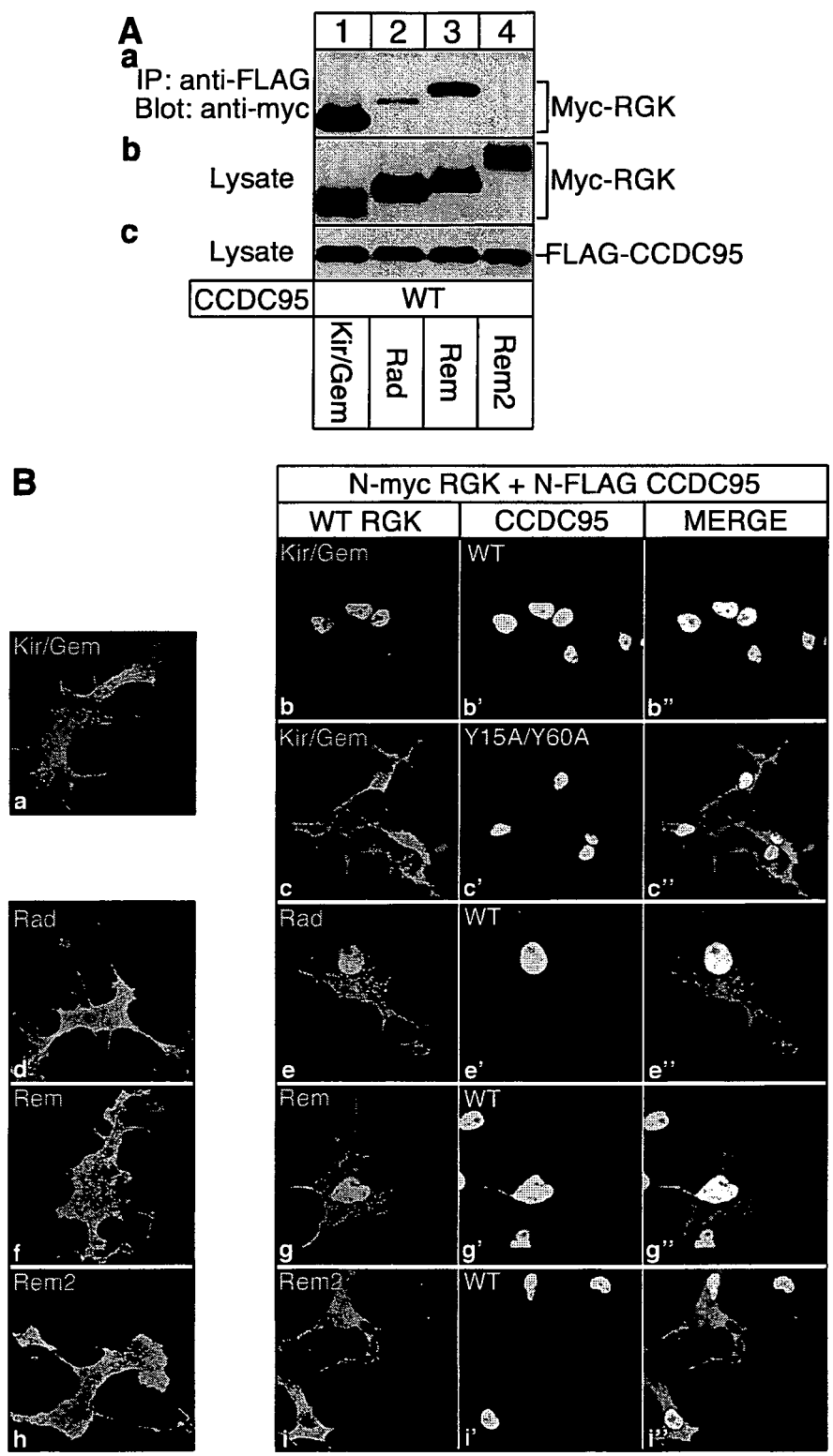
Figure 3:
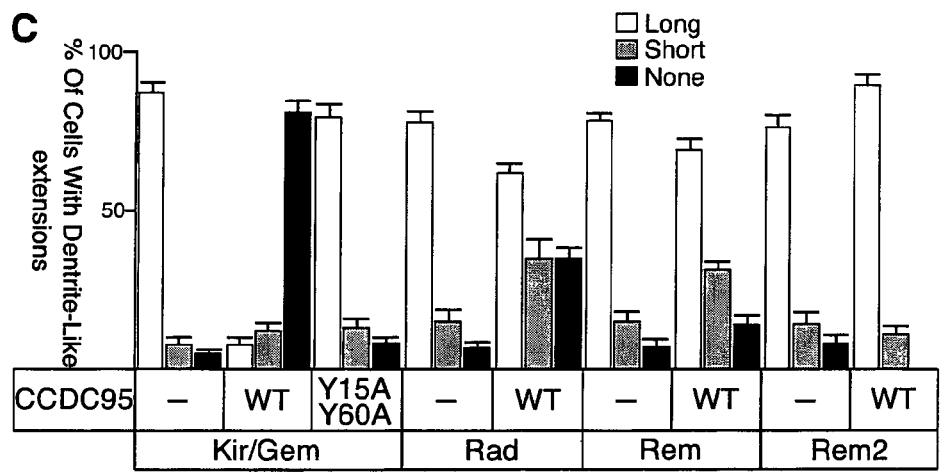
Figure 3:
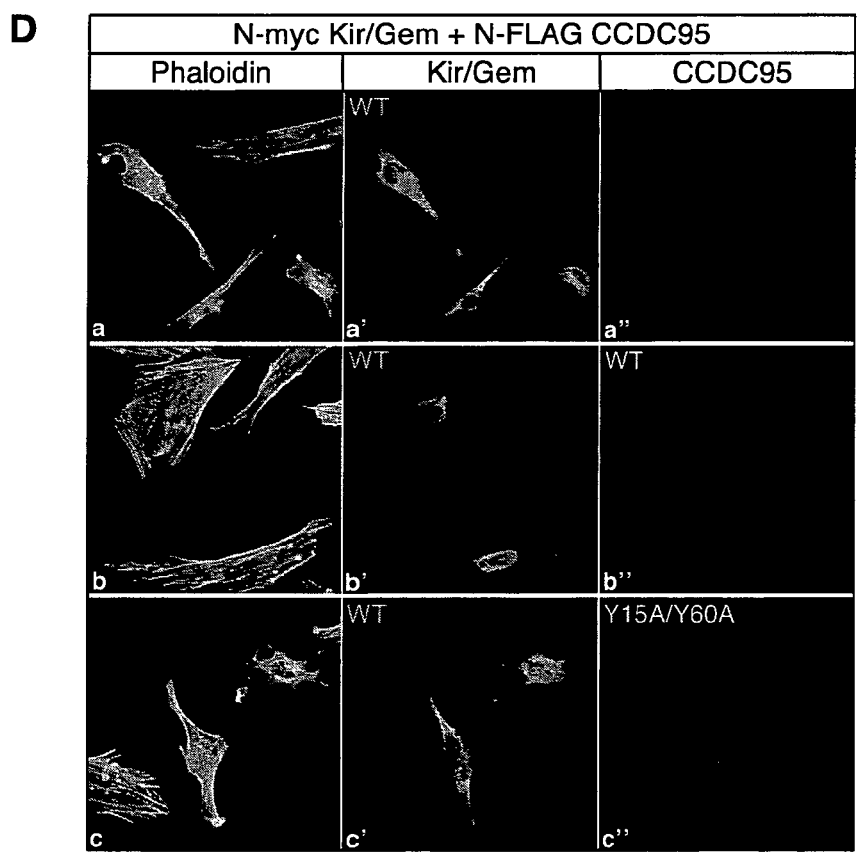

FIG. 3. Interaction of CCDC95 with other RGK family members and functional effect on Kir/Gem induced changes in cell morphology.

A Coimmunoprecipitation of CCDC95 with Rad, Rem and Rem-2. (a) Cells were cotransfected with cDNAs for CCDC95 FLAG-CCDC95 and Myc-Rad, Rem or Rem-2. CCDC95 was then immunoprecipitated and associated RGK proteins were detected by Western blot using anti-tag antibodies. (b and c) Cell lysates were blotted with anti-Myc (b) or anti-FLAG (c) antibodies to monitor RGK protein and CCDC95 expression levels, respectively.

B CCDC95 regulates the subcellular distribution of RGK proteins and Kir/Gem-mediated changes in cell morphology. COS-1 cells were transfected with cDNAs for Myc-RGK proteins, either alone or together with WT or mutated FLAGCCDC95. RGK (red) and CCDC95 (green) proteins where then localized by confocal immunoflourescence microscopy using anti-tag antibodies. Areas of colocalization are in yellow in the merged image.

C Quantification of the morphological changes (see Materials and Methods for details).

D CCDC95 abrogates the Kir/Gem induced collapse of stress fibers. Swiss 3T3 cells were transfected with cDNAs for Myc-Kir/Gem, either alone or together with WT or mutated FLAG-CCDC95. RGK (red) and CCDC95 (blue) proteins where then localized by confocal immunoflourescence microscopy using anti-tag antibodies. Actin filaments (green) were labelled with fluorescent phaloidin.

Figure 4:
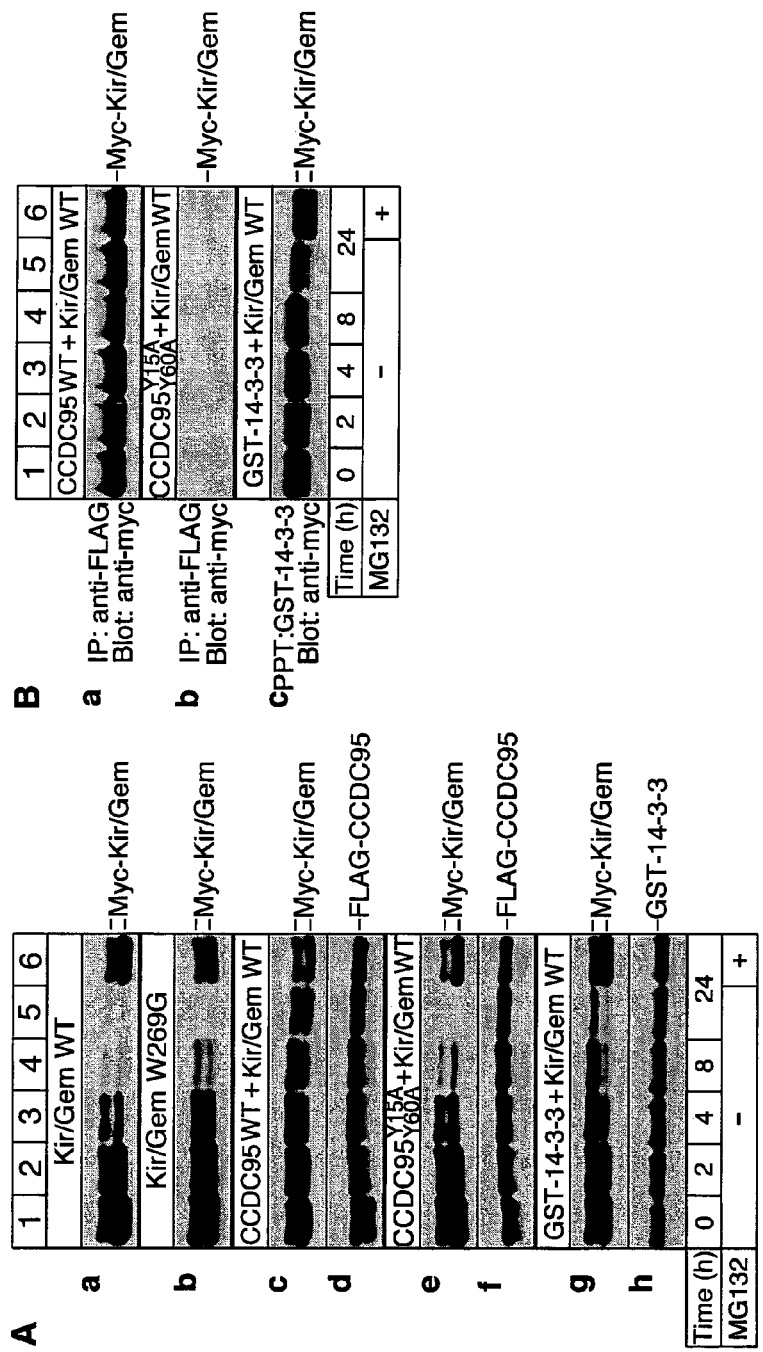

FIG. 4. CCDC95 stabilizes Kir/Gem

A Turnover of Kir/Gem and CCDC95. COS-1 cells were transfected with cDNAs from WT or mutated Myc-Kir/Gem, either alone or together with WT or mutated FLAG-CCDC95 or GST-14-3-3. Protein synthesis was blocked with cyclohex- imide, either in the presence of absence of a proteasome inhibitor (MG132). Cells were lysed at the indicated time points. Kir/Gem, CCDC95 and 14-3-3 were detected by Western blot using anti-tag antibodies.

B Association between CCDC95 and Kir/Gem following cycloheximide and MG132 treatment. An CCDC95 aliquot of the same lysates was used to coimmunoprecipitate Kir/Gem and WT or mutated CCDC95, or GST-14-3-3.

Figure 5:
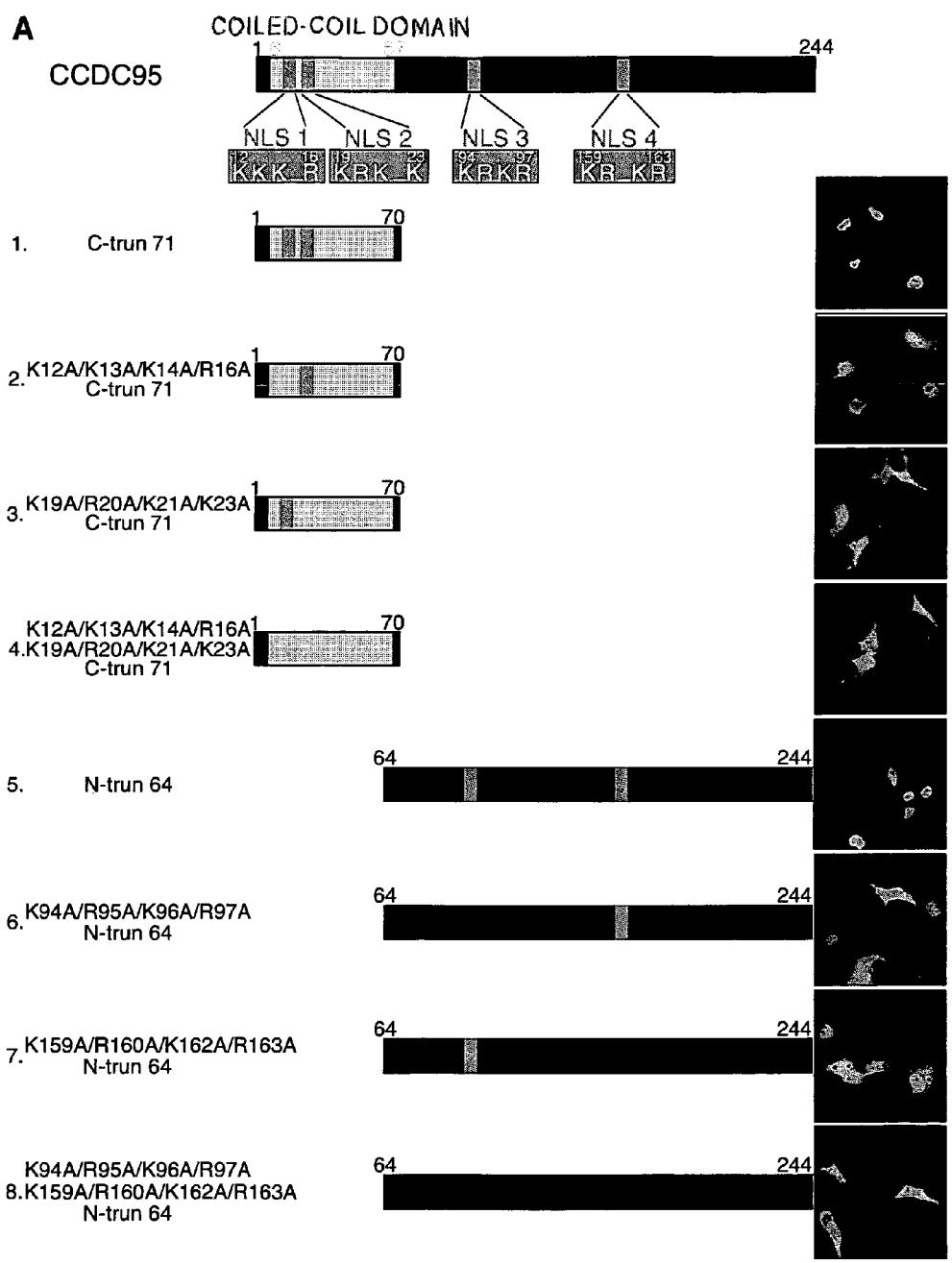
Figure 5:
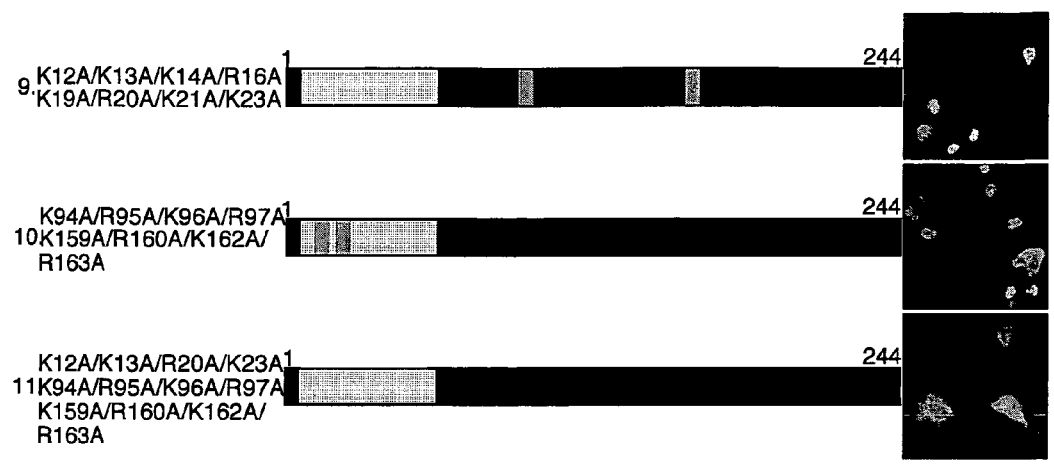
Figure 5:
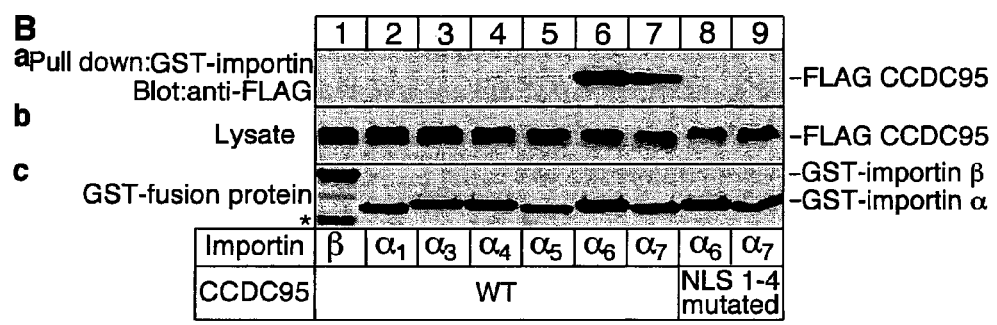
Figure 5:
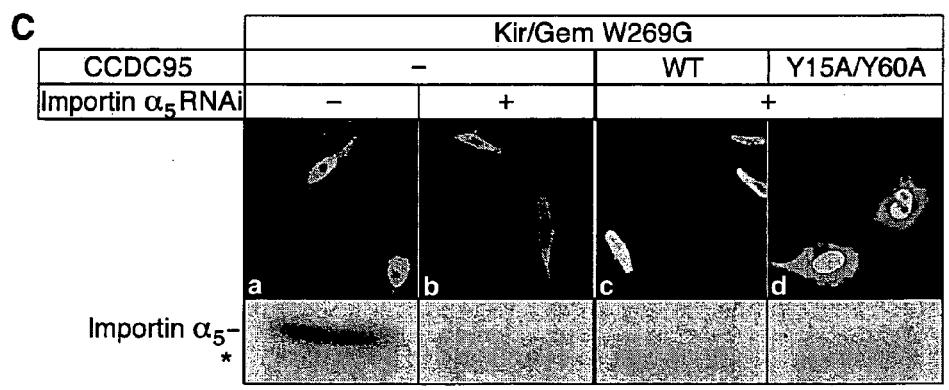

FIG. 5. CCDC95 interacts with specific importins via NLSs and participates in nuclear transport of Kir/Gem.

A Identification of NLSs in CCDC95. The coiled-coil domain (green) and the four identified NLSs (red) are depicted. COS-1 cells were transfected with cDNAs for WT FLAG-CCDC95 or the indicated truncations or mutations. CCDC95 (green) proteins where then localized by confocal immunoflourescence microscopy using anti-tag antibodies.

B Binding of importins to CCDC95. (a) Pull down experiment. Immobilized recombinant GST-importins were incubated with homogenates of cells expressing WT FLAG-CCDC95 or a mutant where all 4 NLSs were abolished (NLS1-4 mutated). Bound CCDC95 proteins were revealed by Western blot using anti-FLAG antibody. (b) Cell lysates were blotted with anti-FLAG antibody to monitor CCDC95 protein expression levels. (c) GST-importin fusion proteins were detected with an anti-GST antibody to verify that similar amounts of fusion protein were used in the assay. (C) CCDC95 participates in nuclear transport of Kir/Gem. Hela cells treated with RNAi to deplete importin α5 protein were transfected with a cDNAs for Myc-Kir/Gem W269G alone or together with WT or mutated FLAG-CCDC95. Kir/Gem (red) and CCDC95 (green) were detected by immunofluorescence microscopy using anti-tag antibodies, respectively. For the coexpression of Kir/Gem and CCDC95, only the merge image is shown (see FIG. 9 for separate images). Depletion of importin α5, expression in RNAi treated cells was monitored by Western blot. A non-specific band detected in addition to the importin is marked with an asterisk.

Figure 6:
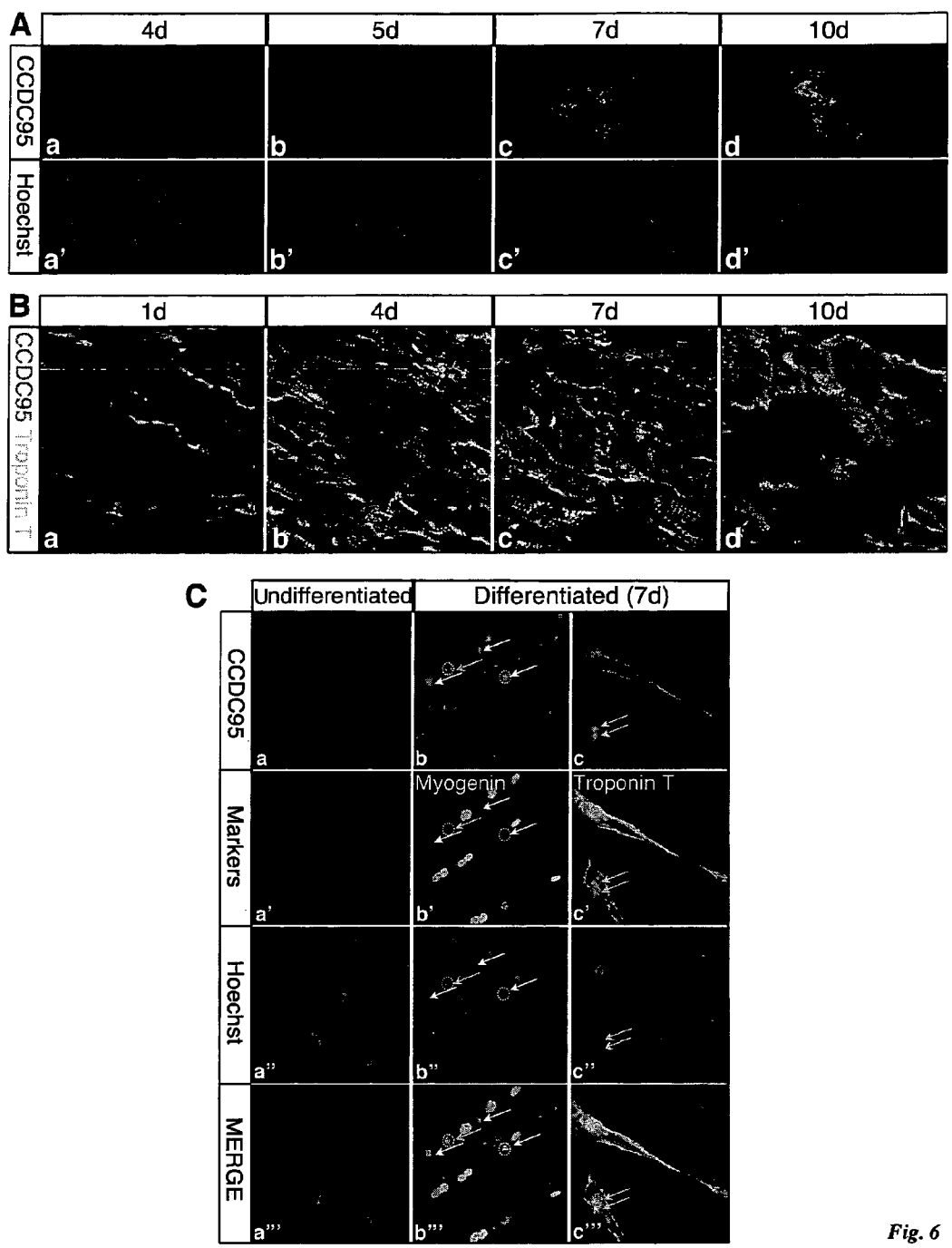
Figure 6:
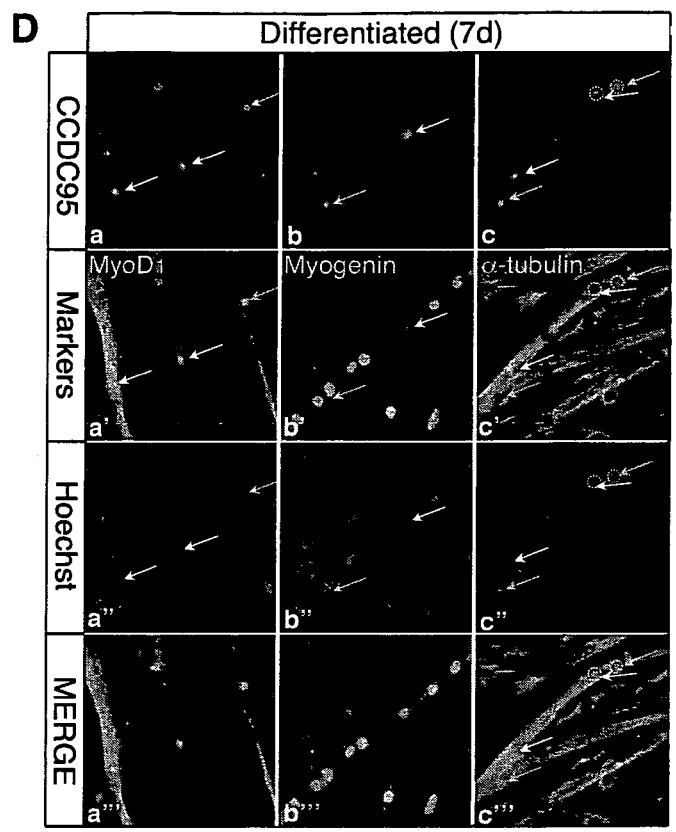
Figure 6:
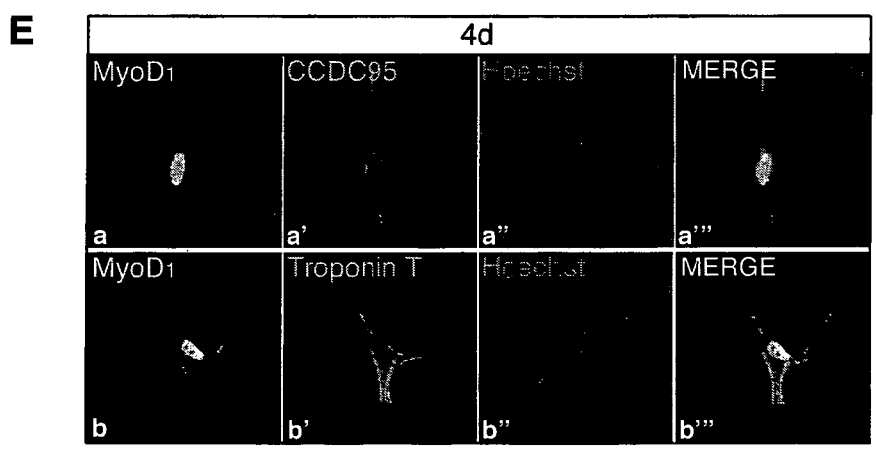

FIG. 6. CCDC95 expression is induced during muscle differentiation

A CCDC95 is induced in embryoid bodies. ES cells were differentiated into cardiomyocytes and cryosections of embryoid bodies. CCDC95 (red) and nuclei (blue) were detected at different time points using antibodies and Hoechst nuclear dye, respectively.

B CCDC95 expression in newborn and adult mice. Cryosections of heart from p1 to p10 old mice were stained with CCDC95 (red) and troponin T (green) antibodies. Areas of colocalization are in yellow in the merged images.

C CCDC95 is induced after in vitro myogenesis. H9c2 cardiomyocyte cells were differentiated for 7 days by serum withdrawal. Differentiated or undifferentiated cells were stained with antibodies to CCDC95 (red) and the muscle markers myogenin or troponin T (green). Nuclei (blue) were labelled with Hoechst nuclear dye (blue). The outline nuclear remnants are circled. White and grey arrows point to remnant nuclei containing either no chromatin or fragmented chromatin, respectively. Note that myogenin is absent from these structures.

D Nuclear remnants are embedded in the microtubule network and express MyoD. Differentiated H9c2 were labeled with antibodies to CCDC95 (red) and either MyoD, myogenin or α-tubulin (green). Nuclei (blue) were detected with Hoechst nuclear dye (blue). The structures labeled by circle or arrows are as described in (C).

E CCDC95 is induced after exogenous expression of MyoD in NIH3T3 fibroblasts. NIH3T3 cells were transfected with a cDNA for MyoD and after 4 days in culture stained with antibodies to MyoD (green) and CCDC95 or troponin T (red).

Figure 7:
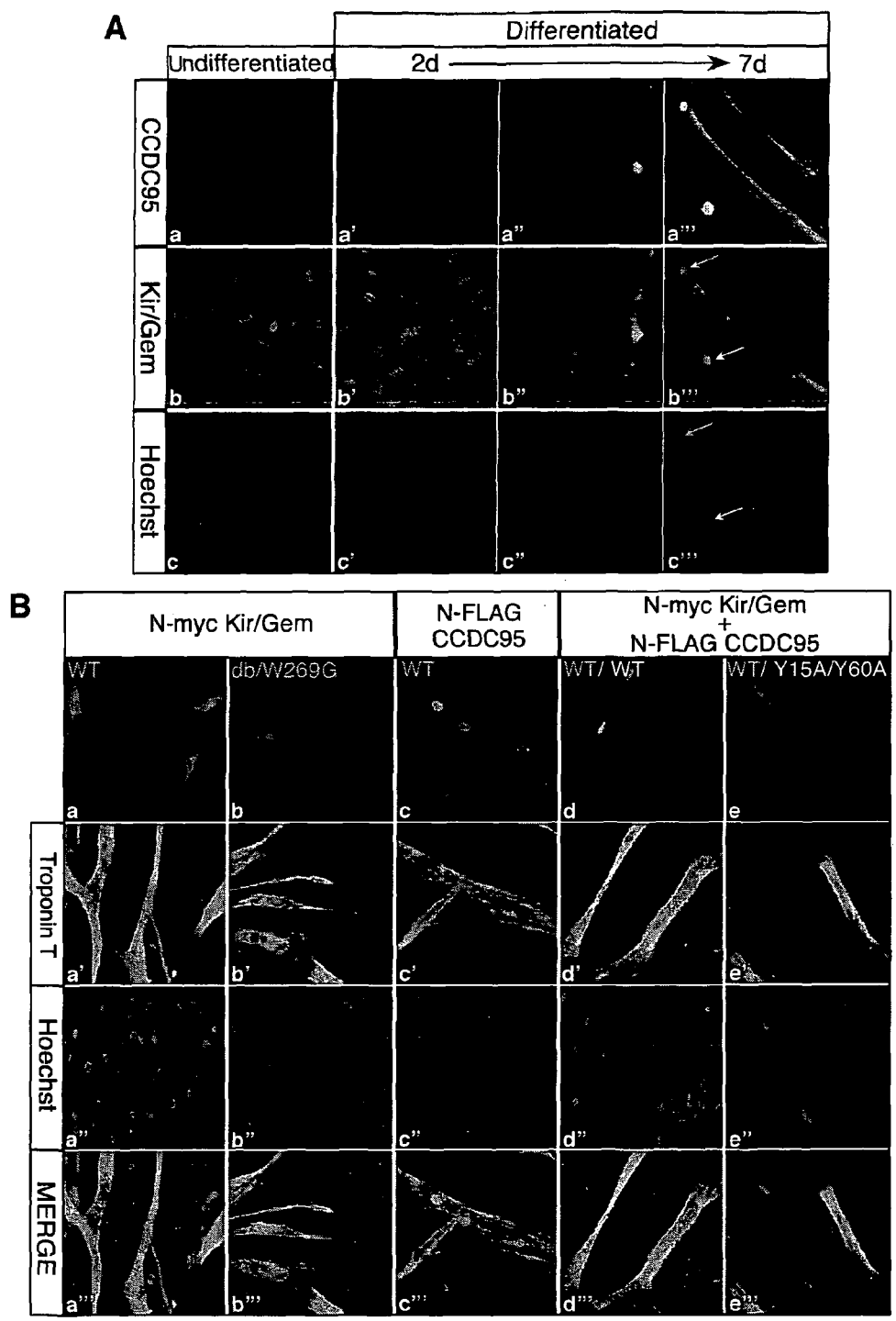
Figure 7:
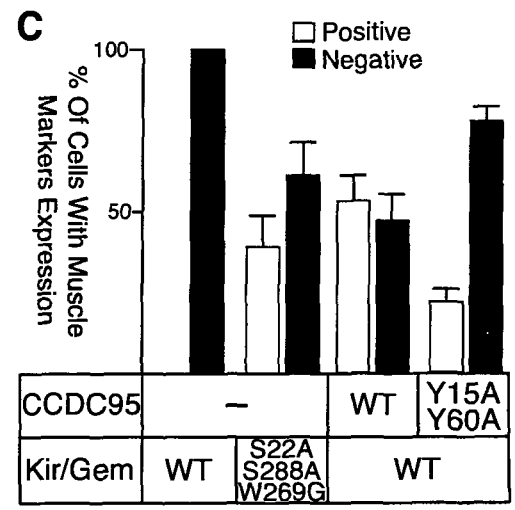
Figure 7:
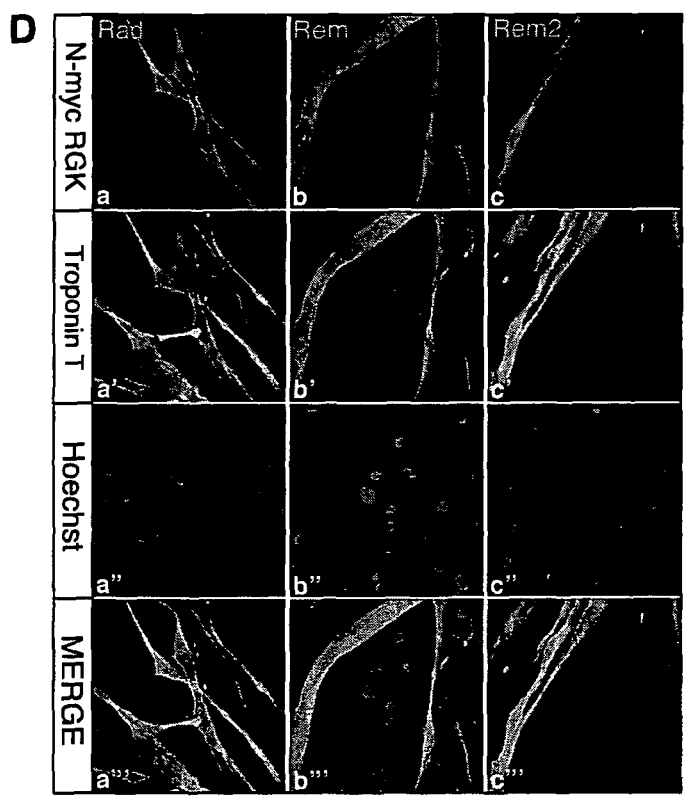

FIG. 7. Kir/Gem and CCDC95 play a coordinated role in muscle differentiation

A Subcellular distribution of Kir/Gem and CCDC95 during differentiation. Endogenous CCDC95 (green) and Kir/Gem (red) and nuclei (blue) were detected using monoclonal and polyclonal antibodies and Hoechst nuclear dye, respectively, in CCDC95 either undifferentiated H9c2 cells of cells differentiated with the indicated time periods.

B Cytoplasmic overexpression of Kir/Gem prevents muscle differentiation and CCDC95 partially relieves this block. Kir/Gem blocks muscle differentiation. H9c2 cells were transfected with cDNAs for WT or mutated Myc-Kir/Gem or FLAGCCDC95 alone, or cotransfected with cDNAs for WT Myc-Kir/Gem and WT or mutated FLAG-CCDC95. After 5-7 days of differentiation, overexpressed Kir/Gem, (red), endogenous troponin T (green) and nuclei (blue) were detected using antibodies or Hoechst nuclear dye, respectively. Note that WT Kir/Gem is restricted to single, undifferentiated cells when overexpressed alone, but present in differentiated myotubes when coexpressed with WT CCDC95. (C) Quantification of the fraction of cells that undergo muscle differentiation under the different conditions (see Material and Methods section).

D Overexpression of Rad, Rem or Rem2 does not affect muscle differentiation. H9c2 cells were transfected with cDNAs for WT Myc-Rad, Rem and Rem2 and cells analysed as described in section (B). RGK proteins and cells were processed as described in section (B).

Figure 8:
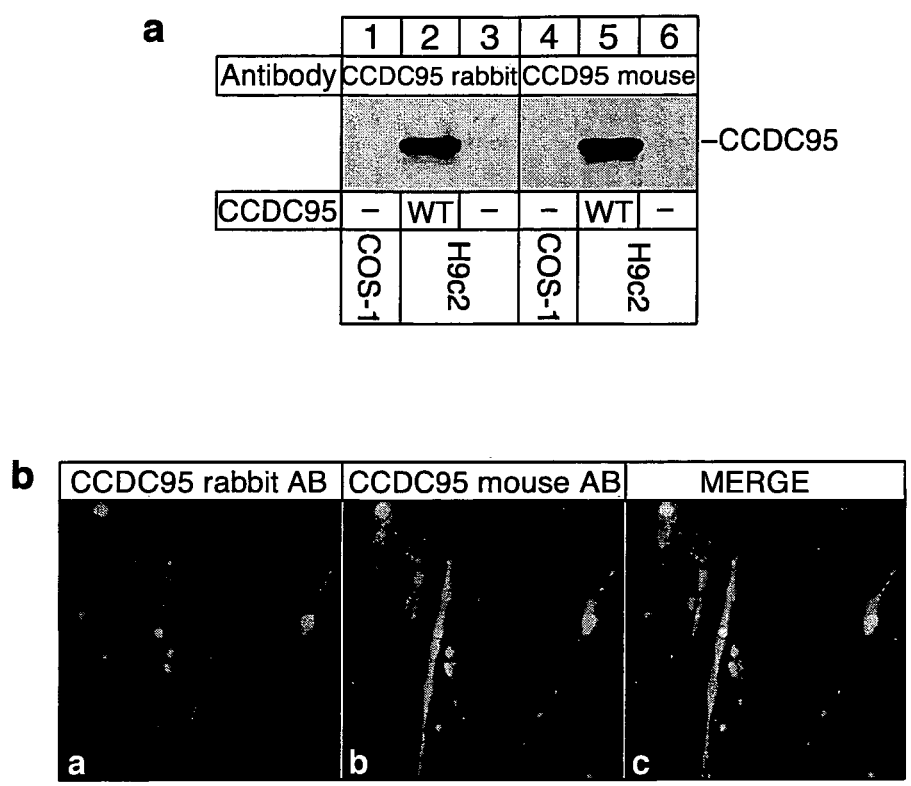

FIG. 8. Characterization of CCDC95 antibodies. (a) Western blot using rabbit and monoclonal mouse anti-CCDC95 antibodies. H9c2 cells were transfected with a cDNA for CCDC95. 48 h later, control cells of cells overexpressing CCDC95 were lysed and subjected to Western blot analysis. A single band of ~30 kDa was detected in transfected H9c2 cells, with a faint band likely corresponding to the endogenous CCDC95. No CCDC95 was detected in COS-1 cells. (b) Immunofluorescence microscopy. Differentiated H9c2 cells were stained with the rabbit and monoclonal mouse anti-CCDC95 antibodies to detect endogenous CCDC95. Areas of colocalization are in yellow in the merged image. Note that both antibodies label similar structures. Compared to the mouse antibody, the rabbit anti-CCDC95 recognized more cellular structures and was used in the present study, with the exception of the images in FIG. 7A and Supplemental Data 6b.

Figure 9:
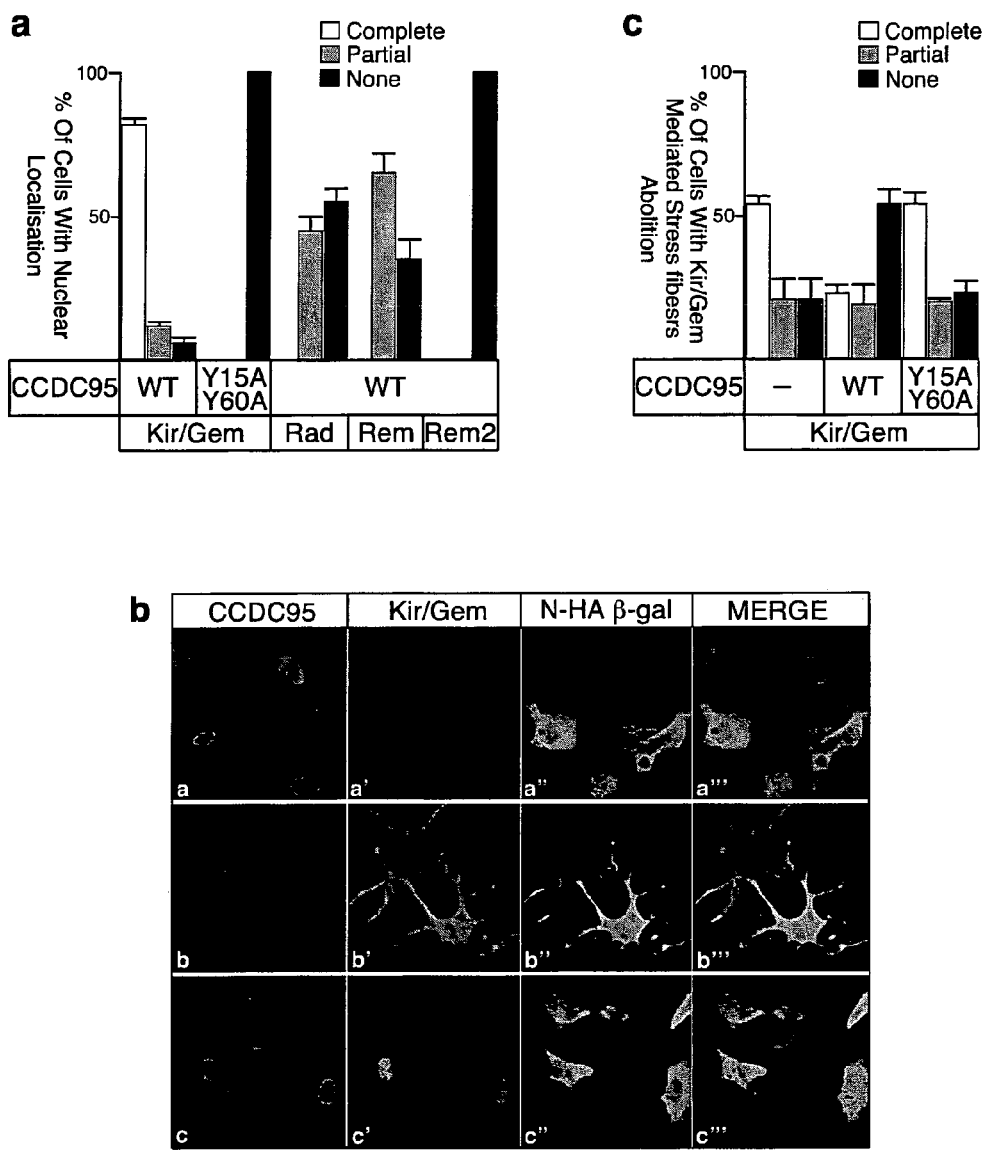

FIG. 9. (a) Quantification of the CCDC95-mediated nuclear relocalization of RGK proteins. The fraction of cells showing complete (white bar), partial (gray bar) and no (black bar) nuclear localization of the indiacted RKG protein is plotted. Partial nuclear localization was considered when a fraction of the RGK protein remained in the cytoplasm. (b) Cell morphology is not affected by Kir/Gem following coexpression with CCDC95 and nuclear relocalization. COS-1 cells were transfected with cDNAs for FLAG-CCDC95, Myc-Kir/Gem and HA-b-galactosidase (N-HA-b-gal). The proteins were detected using anti-tag antibodies and immunofluorescence microscopy, the β-galactosidase labeling served to assess changes in cell shape. Note how Kir/Gem overexpression produces dendrite-like extensions (panel b-b"), whereas no morphological changes are observed if CCDC95 is expressed alone or with Kir/Gem Regulation of nuclear transport of Kir/Gem-2-(panel a-a''' and c-c'''). (c) Quantification of the abrogation of Kir/Gem-induced stress fiber dissassembly. The fraction of cells showing complete (white bar), partial (gray bar) and no (black bar) stress fiber abolition is plotted.

Figure 10:
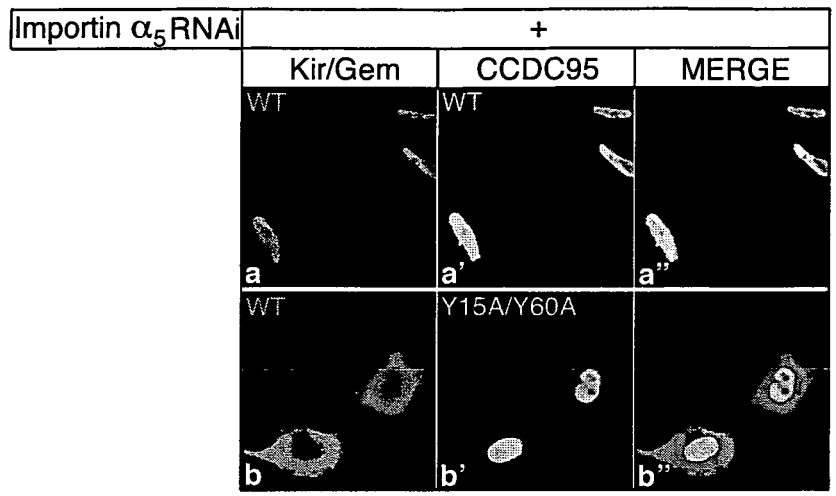

FIG. 10. CCDC95 contributes to nuclear transport of Kir/Gem. Importin α5 was depleted in Hela cells by RNAi and transfected with a cDNA for Myc-Kir/Gem W269G together with WT FLAG-CCDC95 (panel a-a") or a mutant defective in Kir/Gem binding (panel b-b"). Kir/Gem (red) and CCDC95 (green) were detected by immunofluorescence microscopy using anti-tag antibodies. Note that in the absence of importin α5, WT but not the mutant CCDC95 can translocate Kir/Gem W269G into the nucleus even in the absence of importin a5, previously shown to be required for nuclear localization of Kir/Gem.

Figure 11:
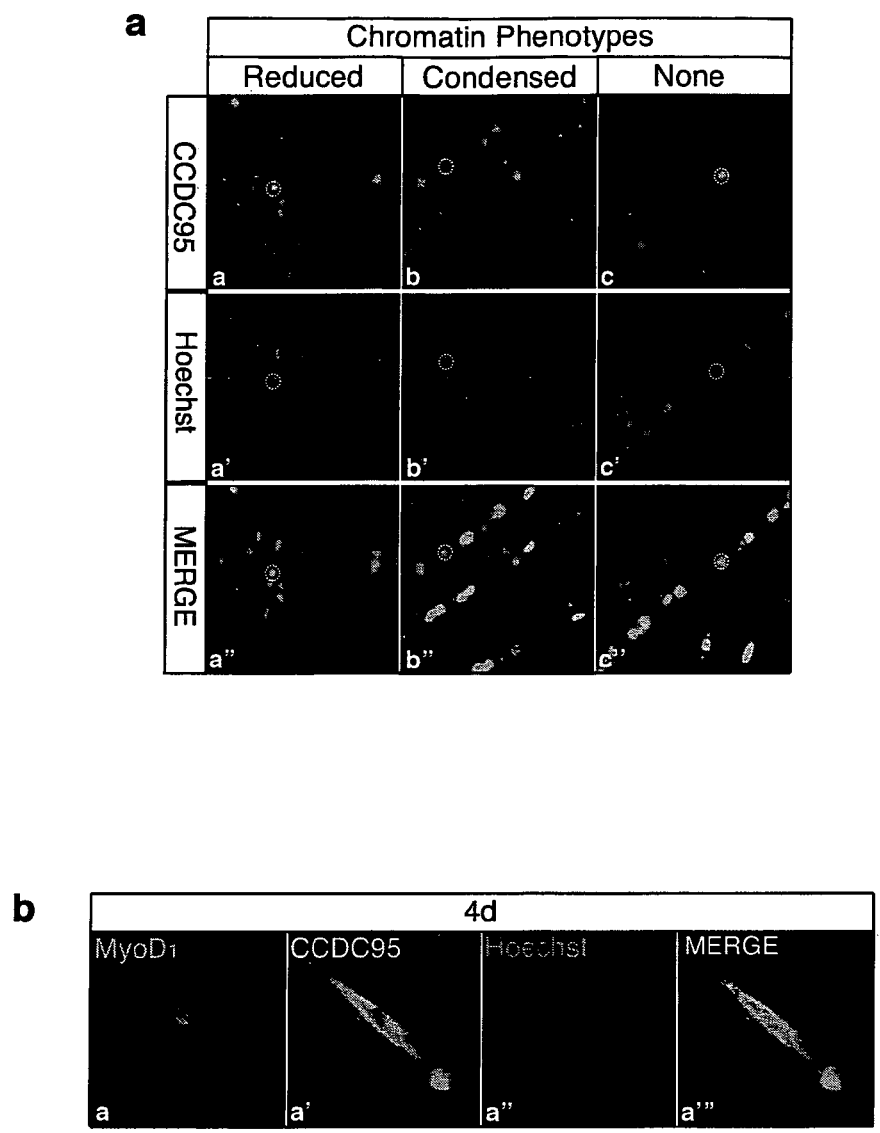

FIG. 11. (a) CCDC95 is expressed in remnant nuclei of mytotubes. H9c2 cardiomyocyte cells were differentiated for 7 days by serum withdrawal and then stained with an antibody-CCDC95 antibody (red) and Hoechst nuclear dye (blue). The outline of remnant nuclei is marked by a dotted circle. Note how in some of these nuclei the chromatin is reduced reduced (panel a-a"), condensed (panel b-b") or absent (panel c-c"). (b) CCDC95 is induced after exogenous expression of MyoD in fibroblast cells. NIH3T3 cells were transfected with a cDNA for MyoD and after 4 days of culture stained with an anti-MyoD (red) and monoclonal anti-CCDC95 (green) antibodies.

Figure 12:
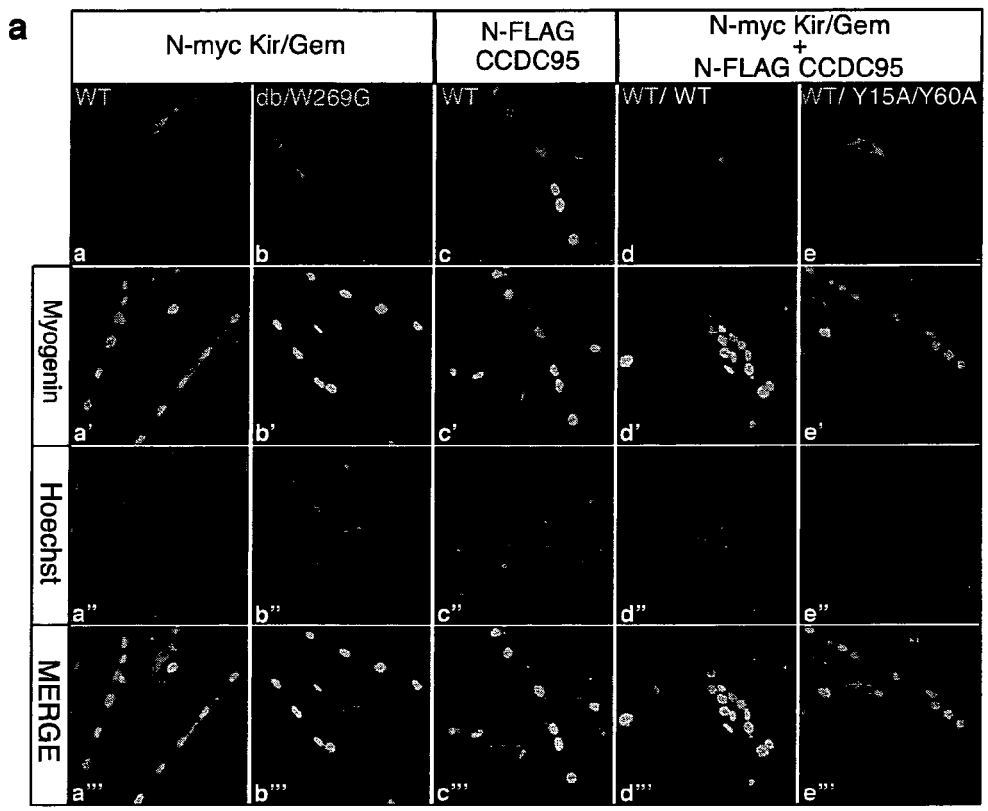
Figure 12:
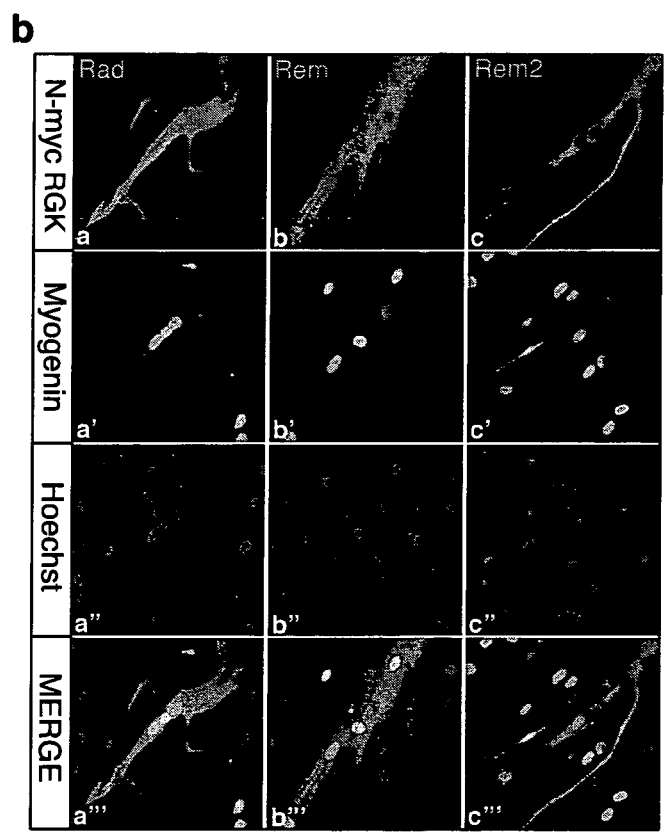

FIG. 12. Kir/Gem and CCDC95 play a coordinated role in muscle differentiation (a) Overexpression of Kir/Gem blocks muscle differentiation and CCDC95 partially Regulation of nuclear transport of Kir/Gem counterbalances this inhibitory effect. H9c2 cells were transfected with cDNAs for WT Myc-Kir/Gem, Kir/Gem S22A/S288A/W269G (db/W269G) or FLAGCCDC95 alone. Alternatively, cell were cotransfected with cDNAs for WT Myc-Kir/Gem and WT FLAG-CCDC95 or a mutant defective in Kir/Gem binding. After 5-7 days of differentiation, cells were analyzed by immunofluorescence microscopy using anti-tag antibodies to detect Kir/Gem (red). Muscle differentiation was monitored by staining for endogenous myogenin (green) and nuclei were labeled with Hoechst dye (blue). Note that the overexpressed WT Kir/Gem is present in single undifferentiated cells whereas CCDC95 and Kir/Gem are coexpressed in myotubes. (b) Overexpression of other RGK proteins does not affect muscle differentiation. H9c2 cells were transfected with cDNAs for Myc-Rad, Rem and Rem2 and the cells were analyzed as described in section (a).

Figure 13:
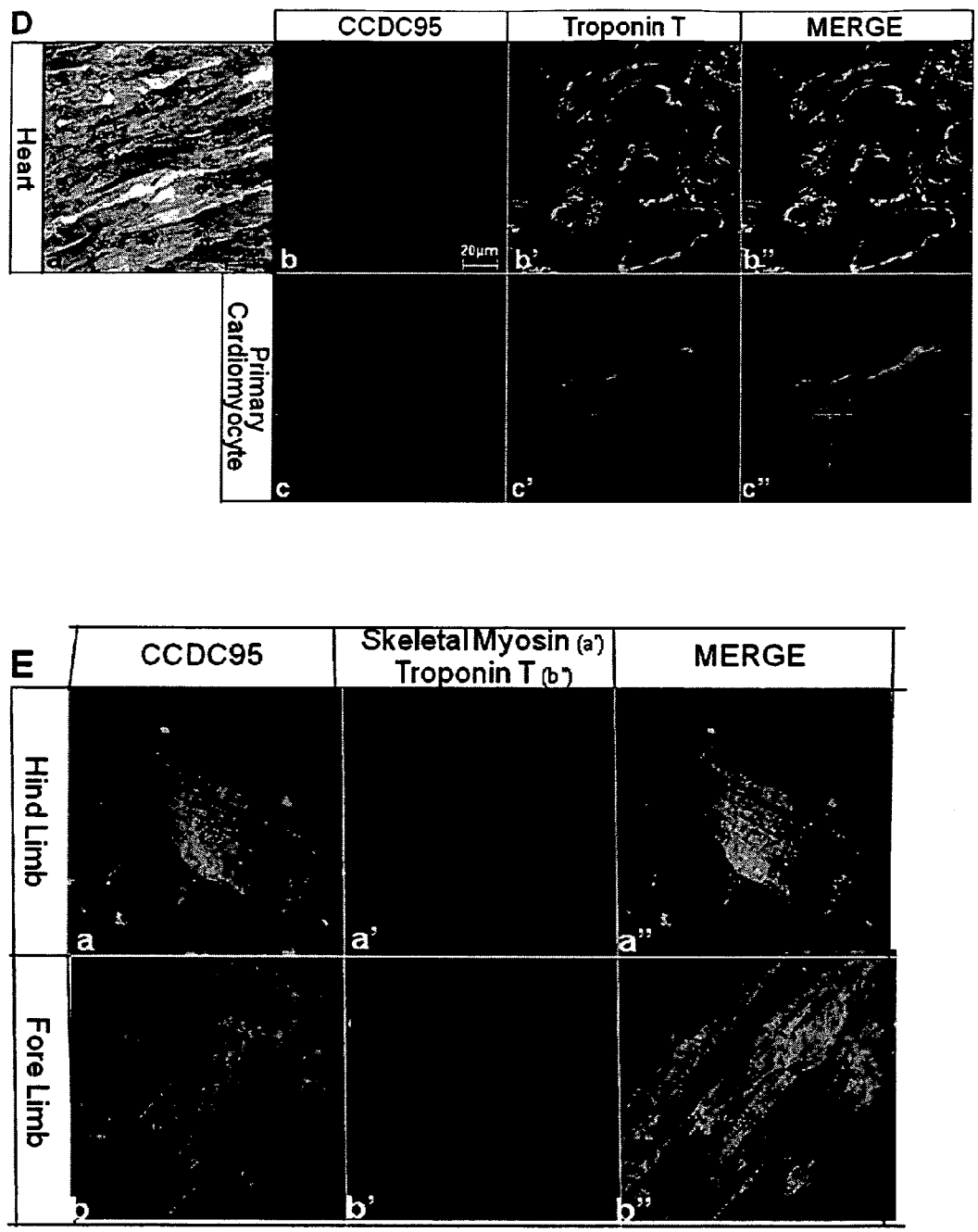

FIG. 13. Immunolocalization of CCDC95 in the heart and skeletal muscle using CCDC95 antibodies. Confocal immunofluorescence microscopy of mouse heart cryosections and primary cardiomyocytes (D) and mouse hind and fore limbs (E) co-stained for CCDC95 (red) and cardiac troponin T (green) antibody. Areas of colocalization are in yellow in the merged image.

Figure 14:
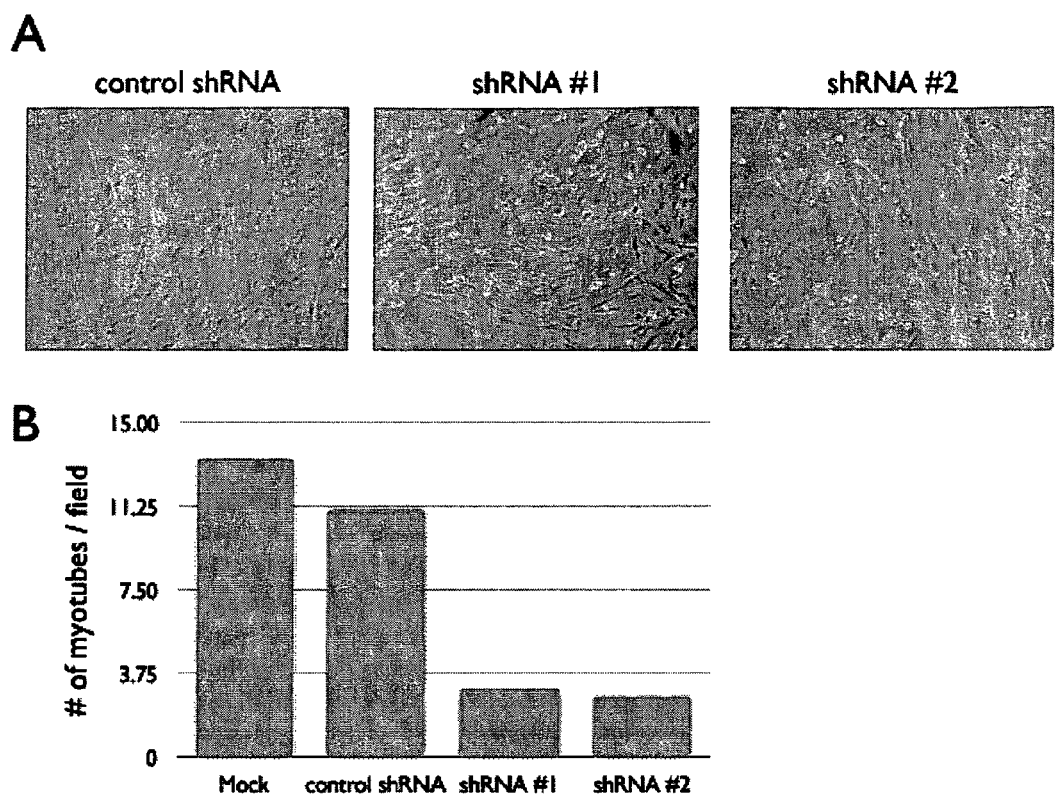

FIG. 14. Transformed C2C12 myoblast cells stably expressing wild type CCDC95 or Silencing RNA causing downregulation of CCDC95 expression. The mioblasts were allowed to differentiate into myotubes for 5 days. The number of myotubes are depicted with confocal microscopy (A) and plotted by the number (B).

DETAILED DISCLOSURE

Here we establish a novel role for Kir/Gem in myogenesis. Myogenic specification CCDC95 and muscle differentiation are orchestrated by the sequential activation of muscle specific HLH (helix-loop-helix) myogenic regulatory factors (MRFs). These transcription factors and regulators include Myf5, MyoD and members of the myocyte enhancer factor family (MEFs). Here we report the characterization of a novel glycoprotein (CCDC95) that is enriched in synapses with a expression predominantly in muscle cells.

The present invention relates to uses for a nucleic acid sequence, termed herein CCDC95, as well as the protein and amino acid sequences, including variations thereof which are capable of modulating RGK small GTP-binding proteins in either cells that express CCDC95 enogenously or those cell that do not express CCDC95 enogenously.

CCDC95 Polynucleotides

According to the invention there is provided an isolated CCDC95 nucleic acid molecule which molecule typically encodes a CCDC95 polypeptide, allelic variant, or analog, including fragments, thereof. Specifically provided are DNA molecules for use in screening for mutations in a CCDC95 gene and DNA molecules for securing expression of a CCDC95 polypeptide capable of modulating RGK small GTP-binding proteins activity in a mammal, and selected from the group consisting of: (a) DNA molecules set out in SEQ ID NOS: 1, 3, 5 or fragments thereof; (b) DNA molecules that hybridize to the DNA molecules defined in (a) or hybridisable fragments thereof; and (c) DNA molecules that code on expression for the amino acid sequence encoded by any of the foregoing DNA molecules.

Preferred DNA molecules according to the invention include DNA molecules comprising the sequence set out in SEQ ID NOS: 1, 3, 5 or fragments thereof.

A polynucleotide is said to "encode" a polypeptide if, in its native state or when manipulated by methods well known to those skilled in the art, it can be transcribed and/or translated to produce the mRNA for and/or the polypeptide or a fragment thereof. The anti-sense strand is the complement of such a nucleic acid, and the encoding sequence can be deduced therefrom.

An "isolated" or "substantially pure" nucleic acid (e.g., an RNA, DNA or a mixed polymer) is one which is substantially separated from other cellular components which naturally accompany a native human sequence or protein, e.g., ribosomes, polymerases, many other human genome sequences and proteins. The term embraces a nucleic acid sequence or protein that has been removed from its naturally occurring environment, and includes recombinant or cloned DNA isolates and chemically synthesized analogs or analogs biologically synthesized by heterologous systems.

"CCDC95 Allele" refers to normal alleles of the CCDC95 gene sequence as well as alleles carrying variations that predispose individuals to develop disorders related to calcium channel disfunction. Such predisposing alleles are also called "CCDC95 susceptibility alleles".

"CCDC95 gene sequence," "CCDC95 gene," "CCDC95 nucleic acids" or "CCDC95 polynucleotide" each refer to polynucleotides that are likely to be expressed in normal tissue, certain alleles of which predispose an individual to develop disorders related to RGK small GTP-binding proteins disfunction. Mutations at the CCDC95 gene sequence may be involved in disruption of calcium homeostasis, cell morphology, muscle or cardiac disorders. The gene sequence is indicated in part by mutations that predispose individuals to develop disorders related to RGK small GTP-binding proteins disfunction.

The CCDC95 gene sequence is intended to include coding sequences, intervening sequences and regulatory elements controlling transcription and/or translation. The CCDC95 gene sequence is intended to include all allelic variations of the DNA sequence.

These terms, when applied to a nucleic acid, refer to a nucleic acid that encodes a CCDC95 polypeptide, fragment, homologue or variant, including, e.g., protein fusions or deletions. The nucleic acids of the present invention will possess a sequence that is either derived from, or substantially similar to a natural CCDC95 encoding gene or one having substantial homology with a natural CCDC95 encoding gene or a portion thereof. The coding sequence for murine VDCC polypeptide is shown in SEQ ID NO: 1, with the amino acid sequence shown in SEQ ID NO: 2. The coding sequence for rodent CCDC95 polypeptide is shown in SEQ ID NO: 3, with the amino acid sequence shown in SEQ ID NO: 4. The coding sequence for human CCDC95 polypeptide is shown in SEQ ID NO: 5, with the amino acid sequence shown in SEQ ID NO: 6.

A nucleic acid or fragment thereof is "substantially homologous" ("or substantially similar") to another if, when optimally aligned (with appropriate nucleotide insertions or deletions) with the other nucleic acid (or its complementary strand), there is nucleotide sequence identity in at least about 60% of the nucleotide bases, usually at least about 70%, more usually at least about 80%, preferably at least about 90%, and more preferably at least about 95-98% of the nucleotide bases.

Alternatively, substantial homology or (identity) exists when a nucleic acid or fragment thereof will hybridise to another nucleic acid (or a complementary strand thereof) under selective hybridisation conditions, to a strand, or to its complement. Selectivity of hybridisation exists when hybridisation that is substantially more selective than total lack of specificity occurs. Typically, selective hybridisation will occur when there is at least about 55% identity over a stretch of at least about 14 nucleotides, preferably at least about 65%, more preferably at least about 75%, and most preferably at least about 90%. The length of homology comparison, as described, may be over longer stretches, and in certain embodiments will often be over a stretch of at least about nine nucleotides, usually at least about 20 nucleotides, more usually at least about 24 nucleotides, typically at least about 28 nucleotides, more typically at least about 32 nucleotides, and preferably at least about 36 or more nucleotides.

Thus, polynucleotides of the invention preferably have at least 75%, more preferably at least 85%, more preferably at least 90% homology to the sequences shown in the sequence listings herein. More preferably there is at least 95%, more preferably at least 98%, homology. Nucleotide homology comparisons may be conducted as described below for polypeptides. A preferred sequence comparison program is the GCG Wisconsin Bestfit program described below. The default scoring matrix has a match value of 10 for each identical nucleotide and −9 for each mismatch. The default gap creation penalty is −50 and the default gap extension penalty is −3 for each nucleotide.

In the context of the present invention, a homologous sequence is taken to include a nucleotide sequence which is at least 60, 70, 80 or 90% identical, preferably at least 95 or 98% identical at the amino acid level over at least 20, 50, 100, 200, 300, 500 or 1000 nucleotides with the nucleotides sequences set out in SEQ ID. Nos 1, 3 or 5. In particular, homology should typically be considered with respect to those regions of the sequence that encode contiguous amino acid sequences known to be essential for the function of the protein rather than non-essential neighbouring sequences. Thus, for example, homology comparisons are preferably made over regions corresponding to the coiled-coil domain and/or other domains of the CCDC95 amino acid sequence set out in SEQ ID NOS: 2, 4 or 6 (see the section on CCDC95 polypeptides below). Preferred polypeptides of the invention comprise a contiguous sequence having greater than 50, 60 or 70% homology, more preferably greater than 80, 90, 95 or 97% homology, to one or more of the nucleotides sequences of SEQ ID NO: 1 which encode amino acids 1 to 70, or 1 to 244 of SEQ ID NO:2 or the equivalent nucleotide sequences in SEQ ID NO: 3 or 5. Preferred polynucleotides may alternatively or in addition comprise a contiguous sequence having greater than 80, 90, 95 or 97% homology to the sequence of SEQ ID NO: 1 that encodes amino acids 1 to 70 of SEQ ID NO:2 or the corresponding nucleotide sequences of SEQ ID NO: 3 or 5.

Other preferred polynucleotides comprise a contiguous sequence having greater than 40, 50, 60, or 70% homology, more preferably greater than 80, 90, 95 or 97% homology to the sequence of SEQ ID NO: 1 that encodes amino acids 1 to 70, and/or 1 to 244 of SEQ ID No: 2 or the corresponding nucleotide sequences of SEQ ID NO: 3 or 5.

Nucleotide sequences are preferably at least 15 nucleotides in length, more preferably at least 20, 30, 40, 50, 100 or 200 nucleotides in length.

Generally, the shorter the length of the polynucleotide, the greater the homology required to obtain selective hybridization. Consequently, where a polynucleotide of the invention consists of less than about 30 nucleotides, it is preferred that the % identity is greater than 75%, preferably greater than 90% or 95% compared with the CCDC95 nucleotide sequences set out in the sequence listings herein. Conversely, where a polynucleotide of the invention consists of, for example, greater than 50 or 100 nucleotides, the % identity compared with the CCDC95 nucleotide sequences set out in the sequence listings herein may be lower, for example greater than 50%, preferably greater than 60 or 75%.

Nucleic acid hybridisation will be affected by such conditions as salt concentration, temperature, or organic solvents, in addition to the base composition, length of the complementary strands, and the number of nucleotide base mismatches between the hybridizing nucleic acids, as will be readily appreciated by those skilled in the art. Stringent temperature conditions will generally include temperatures in excess of 30 degrees C., typically in excess of 37 degrees C., and preferably in excess of 45 degrees C. Stringent salt conditions will ordinarily be less than 1000 mM, typically less than 500 mM, and preferably less than 200 mM. However, the combination of parameters is much more important than the measure of any single parameter. An example of stringent hybridization conditions is 65° C. and 0.1×SSC (1×SSC=0.15 M NaCl, 0.015 M sodium citrate pH 7.0).

The "polynucleotide" compositions of this invention include RNA, cDNA, genomic DNA, synthetic forms, and mixed polymers, both sense and antisense strands, and may be chemically or biochemically modified or may contain non-natural or derivatized nucleotide bases, as will be readily appreciated by those skilled in the art. Such modifications include, for example, labels, methylation, substitution of one or more of the naturally occurring nucleotides with an analog, internucleotide modifications such as uncharged linkages (e.g., methyl phosphonates, phosphotriesters, phosphoamidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.). Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule.

The present invention provides recombinant nucleic acids comprising all or part of the CCDC95 region. The recombinant construct may be capable of replicating autonomously in a host cell. Alternatively, the recombinant construct may become integrated into the chromosomal DNA of the host cell. Such a recombinant polynucleotide comprises a polynucleotide of genomic, cDNA, semi-synthetic, or synthetic origin which, by virtue of its origin or manipulation, 1) is not associated with all or a portion of a polynucleotide with which it is associated in nature; 2) is linked to a polynucleotide other than that to which it is linked in nature; or 3) does not occur in nature.

Therefore, recombinant nucleic acids comprising sequences otherwise not naturally occurring are provided by this invention. Although the wild-type sequence may be employed, it will often be altered, e.g., by deletion, substitution or insertion.

A "Recombinant nucleic acid" is a nucleic acid that is not naturally occurring, or which is made by the artificial combination of two otherwise separated segments of sequence. This artificial combination is often accomplished by either chemical syntheses means, or by the artificial manipulation of isolated segments of nucleic acids, by genetic engineering techniques. Such is usually done to replace a codon with a redundant codon encoding the same or a conservative amino acid, while typically introducing or removing a sequence recognition site. Alternatively, it is performed to join together nucleic acid segments of desired functions to generate a desired combination of functions.

cDNA or genomic libraries of various types may be screened as natural sources of the nucleic acids of the present invention, or such nucleic acids may be provided by amplification of sequences resident in genomic DNA or other natural sources, e.g., by PCR. The choice of cDNA libraries normally corresponds to a tissue source that is abundant in mRNA for the desired proteins. Phage libraries are normally preferred, but other types of libraries may be used. Clones of a library are spread onto plates, transferred to a substrate for screening, denatured and probed for the presence of desired sequences.

The nucleic acid sequences used in this invention will usually comprise at least about five codons (15 nucleotides), more usually at least about 7-15 codons, and most preferably, at least about 35 codons. One or more introns may also be present. This number of nucleotides is usually about the minimal length required for a successful probe that would hybridize specifically with a CCDC95-encoding sequence.

Techniques for nucleic acid manipulation are described generally, for example, in Sambrook et al., 1989: "Molecular Cloning: a laboratory manual. Sambrook, J., Fritsch, E. F. and Maniatis, T. (1989). Coldspring Harbour Laboratory Press, Coldspring Harbour, N.Y. or Ausubel et al., 1992 Current Protocols in Molecular Biology. Ausubel, F. M., Brent, R., Kingston, R. E., Moore, D. D., Seidman, J. G., Smith, J. G. and Struhl, K. (1987). John Wiley and Sons, NY. Reagents useful in applying such techniques, such as restriction enzymes and the like, are widely known in the art and commercially available from such vendors as New England BioLabs, Boehringer Mannheim, Amersham, Promega Biotec, U.S. Biochemicals, New England Nuclear, and a number of other sources. The recombinant nucleic acid sequences used to produce fusion proteins of the present invention may be derived from natural or synthetic sequences. Many natural gene sequences are obtainable from various cDNA or from genomic libraries using appropriate probes. See, GenBank, National Institutes of Health.

As used herein, the terms "CCDC95 gene sequence," and "CCDC95 allele" refer to the double-stranded DNA comprising the gene sequence, allele, or region, as well as either of the single-stranded DNAs comprising the gene sequence, allele or region (i.e. either of the coding and non-coding strands).

As used herein, a "portion" of the CCDC95 gene sequence or region or allele is defined as having a minimal size of at least about eight nucleotides, or preferably about 15 nucleotides, or more preferably at least about 25 nucleotides, and may have a minimal size of at least about 40 nucleotides.

Probe sequences may also hybridize specifically to duplex DNA under certain conditions to form triplex or other higher order DNA complexes. The preparation of such probes and suitable hybridisation conditions are well known in the art.

Detectably labeled nucleic acid molecules hybridisable to a DNA molecule of the invention are also provided and include nucleic acid molecules hybridisable to a non-coding region of a CCDC95 nucleic acid, which non-coding region is selected from the group consisting of an intron, a 5' non-coding region, and a 3' non-coding region. The present invention also provides oligonucleotide primers for amplifying human genomic DNA encoding a CCDC95 polypeptide such as oligonucleotides set out in the Examples.

"Probes". Polynucleotide polymorphisms associated with CCDC95 alleles which predispose to an imbalance of RGK small GTP-binding proteins concentration or subcellular location are detected by hybridisation with a polynucleotide probe which forms a stable hybrid with that of the target sequence, under stringent to moderately stringent hybridisation and wash conditions. If it is expected that the probes will be perfectly complementary to the target sequence, stringent conditions will be used. Hybridisation stringency may be lessened if some mismatching is expected, for example, if variants are expected with the result that the probe will not be completely complementary. Conditions are chosen which rule out nonspecific/adventitious bindings, that is, which minimize noise. Since such indications identify neutral DNA polymorphisms as well as mutations, these indications need further analysis to demonstrate detection of a CCDC95 susceptibility allele.

Probes for CCDC95 alleles may be derived from the sequences of the CCDC95 region or its cDNAs. The probes may be of any suitable length, which span all or a portion of the CCDC95 region and which allow specific hybridisation to the CCDC95 region. If the target sequence contains a sequence identical to that of the probe, the probes may be short, e.g., in the range of about 8-30 base pairs, since the hybrid will be relatively stable under even stringent conditions. If some degree of mismatch is expected with the probe, i.e., if it is suspected that the probe will hybridize to a variant region, a longer probe may be employed which hybridises to the target sequence with the requisite specificity.

The probes will include an isolated polynucleotide attached to a label or reporter molecule and may be used to isolate other polynucleotide sequences, having sequence similarity by standard methods. For techniques for preparing and labeling probes see, e.g Sambrook et al., 1989: "Molecular Cloning: a laboratory manual. Sambrook, J., Fritsch, E. F. and Maniatis, T. (1989). Coldspring Harbour Laboratory Press, Coldspring Harbour, N.Y. or Ausubel et al., 1992 Current Protocols in Molecular Biology. Ausubel, F. M., Brent, R., Kngston, R. E., Moore, D. D., Seidman, J. G., Smith, J. G. and Struhl, K. (1987). John Wiley and Sons, NY. Other similar polynucleotides may be selected by using homologous polynucleotides. Alternatively, polynucleotides encoding these or similar polypeptides may be synthesized or selected by use of the redundancy in the genetic code. Various codon substitutions may be introduced, e.g., by silent changes (thereby producing various restriction sites) or to optimize expression for a particular system. Mutations may be introduced to modify the properties of the polypeptide, perhaps to change ligand-binding affinities, interchain affinities, or the polypeptide degradation or turnover rate.

Probes comprising synthetic oligonucleotides or other polynucleotides of the present invention may be derived from naturally occurring or recombinant single- or double-stranded polynucleotides, or be chemically synthesized. Probes may also be labeled by nick translation, Klenow fill-in reaction, or other methods known in the art.

Portions of the polynucleotide sequence having at least about eight nucleotides, usually at least about 15 nucleotides, and fewer than about 6 kb, usually fewer than about 1.0 kb, from a polynucleotide sequence encoding CCDC95 are preferred as probes. The probes may also be used to determine whether mRNA encoding CCDC95 is present in a cell or tissue and whether the genomic organisation of the CCDC95 locus is deleted or otherwise damaged.

A variety of DNA technologies may thus be used to identify mutant alleles in a range of individuals. A number of these alleles may comprise minor alterations to the genomic sequence, such as point mutations including insertions deletions and/or substitutions. Fragments of nucleic acid which comprise these mutations may be used in diagnostic screening as described below. Accordingly, the present invention provides one or more CCDC95 polynucleotides or fragments thereof comprising mutations with respect to the wild type sequence, such as the sequence shown in SEQ ID No. 3. In a further embodiment, the present invention provides a plurality of CCDC95 polynucleotides or fragments thereof for use in screening the DNA of an individual for the presence of one or more mutations/polymorphisms. The plurality of sequences is conveniently provided immobilized to a solid substrate as is described below.

Nucleic Acid Arrays—"DNA Chip" Technology

Polynucleotides of the invention, including probes that may be used to detect both normal (wild type) and abnormal CCDC95 sequences in nucleic acid samples taken from patients, may be immobilized to a solid phase support. The probes for CCDC95 will typically form part of a library of DNA molecules that may be used to detect simultaneously a number of different genes in a given genome.

Techniques for producing immobilised libraries of DNA molecules have been described in the art. Generally, most prior art methods describe the synthesis of single-stranded nucleic acid molecule libraries, using for example masking techniques to build up various permutations of sequences at the various discrete positions on the solid substrate. U.S. Pat. No. 5,837,832, the contents of which are incorporated herein by reference, describes an improved method for producing DNA arrays immobilised to silicon substrates based on very large scale integration technology. In particular, U.S. Pat. No. 5,837,832 describes a strategy called "tiling" to synthesize specific sets of probes at spatially-defined locations on a substrate which may be used to produced the immobilised DNA libraries of the present invention. U.S. Pat. No. 5,837,832 also provides references for earlier techniques that may also be used. Thus nucleic acid probes may be synthesised in situ on the surface of the substrate.

Alternatively, single-stranded molecules may be synthesised off the solid substrate and each pre-formed sequence applied to a discrete position on the solid substrate. For example, nucleic acids may be printed directly onto the substrate using robotic devices equipped with either pins or pizo electric devices.

The library sequences are typically immobilised onto or in discrete regions of a solid substrate. The substrate may be porous to allow immobilisation within the substrate or substantially non-porous, in which case the library sequences are typically immobilised on the surface of the substrate. The solid substrate may be made of any material to which polypeptides can bind, either directly or indirectly. Examples of suitable solid substrates include flat glass, silicon wafers, mica, ceramics and organic polymers such as plastics, including polystyrene and polymethacrylate. It may also be possible to use semi-permeable membranes such as nitrocellulose or nylon membranes, which are widely available. The semipermeable membranes may be mounted on a more robust solid surface such as glass. The surfaces may optionally be coated with a layer of metal, such as gold, platinum or other transition metal. A particular example of a suitable solid substrate is the commercially available BiaCore™ chip (Pharmacia Biosensors).

Preferably, the solid substrate is generally a material having a rigid or semi-rigid surface. In preferred embodiments, at least one surface of the substrate will be substantially flat, although in some embodiments it may be desirable to physically separate synthesis regions for different polymers with, for example, raised regions or etched trenches. It is also preferred that the solid substrate is suitable for the high density application of DNA sequences in discrete areas of typically from 50 to 100 µm, giving a density of 10000 to 40000 $cm^{-2}$.

The solid substrate is conveniently divided up into sections. This may be achieved by techniques such as photoetching, or by the application of hydrophobic inks, for example teflon-based inks (Cel-line, USA).

Discrete positions, in which each different member of the library is located may have any convenient shape, e.g., circular, rectangular, elliptical, wedge-shaped, etc.

Attachment of the nucleic acid sequences to the substrate may be by covalent or non-covalent means. The nucleic acid sequences may be attached to the substrate via a layer of molecules to which the library sequences bind. For example, the nucleic acid sequences may be labelled with biotin and the substrate coated with avidin and/or streptavidin. A convenient feature of using biotinylated nucleic acid sequences is that the efficiency of coupling to the solid substrate can be determined easily. Since the nucleic acid sequences may bind only poorly to some solid substrates, it is often necessary to provide a chemical interface between the solid substrate (such as in the case of glass) and the nucleic acid sequences. Examples of suitable chemical interfaces include hexaethylene glycol. Another example is the use of polylysine coated glass, the polylysine then being chemically modified using standard procedures to introduce an affinity ligand. Other methods for attaching molecules to the surfaces of solid substrate by the use of coupling agents are known in the art see for example WO98/49557.

Binding of complementary nucleic acid sequence to the immobilised nucleic acid library may be determined by a variety of means such as changes in the optical characteristics of the bound nucleic acid (i.e. by the use of ethidium bromide) or by the use of labelled nucleic acids, such as polypeptides labelled with fluorophores. Other detection techniques that do not require the use of labels include optical techniques such as optoacoustics, reflectometry, ellipsometry and surface plasmon resonance (SPR)—see WO97/49989, incorporated herein by reference.

Thus the present invention provides a solid substrate having immobilized thereon at least one polynucleotide of the present invention, preferably two or more different polynucleotides of the present invention, for example two or more different CCDC95 polynucleotides corresponding to different alleles. In a preferred embodiment the solid substrate further comprises polynucleotides derived from genes other than the CCDC95 gene.

Preparation of Recombinant or Chemically Synthesised CCDC95 Nucleic Acids; Vectors, Transformation, Host Cells Any CCDC95 nucleic acid specimen, in purified or non-purified form, can be utilised as the starting nucleic acid or acids.

PCR is one such process that may be used to amplify CCDC95 gene sequences. This technique may amplify, for example, DNA or RNA, including messenger RNA, wherein DNA or RNA may be single stranded or double stranded. In the event that RNA is to be used as a template, enzymes, and/or conditions optimal for reverse transcribing the template to DNA would be utilized. In addition, a DNA-RNA hybrid that contains one strand of each may be utilized. A mixture of nucleic acids may also be employed, or the nucleic acids produced in a previous amplification reaction described herein, using the same or different primers may be so utilised.

The specific nucleic acid sequence to be amplified, i.e., the polymorphic gene sequence, may be a fraction of a larger molecule or can be present initially as a discrete molecule, so that the specific sequence constitutes the entire nucleic acid. It is not necessary that the sequence to be amplified is present initially in a pure form; it may be a minor fraction of a complex mixture, such as contained in whole human DNA.

DNA utilized herein may be extracted from a body sample, such as blood, tissue material, muscle tissue heart tissue and the like by a variety of techniques such as that described by Maniatis, et. al. in Molecular Cloning: A Laboratory Manual, Cold Spring Harbor, N.Y., p 280-281, 1982). If the extracted sample has not been purified, it may be treated before amplification with an amount of a reagent effective to open the cells, or animal cell membranes of the sample, and to expose and/or separate the strand(s) of the nucleic acid(s). This lysing and nucleic acid denaturing step to expose and separate the strands will allow amplification to occur much more readily.

The deoxyribonucleotide triphosphates dATP, dCTP, dGTP and dTTP are added to the synthesis mixture, either separately or together with the primers, in adequate amounts and the resulting solution is heated to about 90 degrees-100 degrees C. from about 1 to 10 minutes, preferably from 1 to 4 minutes. After this heating period, the solution is allowed to cool, which is preferable for the primer hybridization. To the cooled mixture is added an appropriate agent for effecting the primer extension reaction (called herein "agent for polymerization"), and the reaction is allowed to occur under conditions known in the art. The agent for polymerization may also be added together with the other reagents if it is heat stable. This synthesis (or amplification) reaction may occur at room temperature up to a temperature above which the agent for polymerization no longer functions. Thus, for example, if DNA polymerase is used as the agent, the temperature is generally no greater than about 40 degree C. Most conveniently the reaction occurs at room temperature.

Allele specific oligonucleotide primers derived from CCDC95 gene sequence may be useful in determining whether a subject is at risk of suffering from the ailments described herein. Primers direct amplification of a target polynucleotide (eg CCDC95) prior to sequencing. Primers used in any diagnostic assays derived from the present invention should be of sufficient length and appropriate sequence to provide initiation of polymerisation. Environmental conditions conducive to synthesis include the presence of nucleoside triphosphates and an agent for polymerisation, such as DNA polymerase, and a suitable temperature and pH.

Primers are preferably single stranded for maximum efficiency in amplification, but may be double stranded. If double stranded, primers may be first treated to separate the strands before being used to prepare extension products. Primers should be sufficiently long to prime the synthesis of CCDC95 extension products in the presence of the inducing agent for polymerization. The exact length of a primer will depend on many factors, including temperature, buffer, and nucleotide composition. Oligonucleotide primers will typically contain 12-20 or more nucleotides, although they may contain fewer nucleotides.

Primers that may be used in diagnostic assays derived from the present invention should be designed to be substantially complementary to each strand of the CCDC95 genomic gene sequence. This means that the primers must be sufficiently complementary to hybridise with their respective strands under conditions that allow the agent for polymerisation to perform. In other words, the primers should have sufficient complementarity with the 5' and 3' sequences flanking the mutation to hybridise therewith and permit amplification of the CCDC95 genomic gene sequence.

Oligonucleotide primers of the invention employed in the PCR amplification process that is an enzymatic chain reaction that produces exponential quantities of CCDC95 gene sequence relative to the number of reaction steps involved. Typically, one primer will be complementary to the negative (−) strand of the CCDC95 gene sequence and the other is complementary to the positive (+) strand. Annealing the primers to denatured nucleic acid followed by extension with an enzyme, such as the large fragment of DNA polymerase I (Klenow) and nucleotides, results in newly synthesised + and − strands containing the target a CCDC95 gene sequence. Because these newly synthesized sequences are also templates, repeated cycles of denaturing, primer annealing, and extension results in exponential production of the region (i.e., the CCDC95 gene sequence) defined by the primers. The product of the chain reaction is a discreet nucleic acid duplex with termini corresponding to the ends of the specific primers employed.

Oligonucleotide primers may be prepared using any suitable method, such as conventional phosphotriester and phosphodiester methods or automated embodiments thereof. In one such automated embodiment, diethylphosphoramidites are used as starting materials and may be synthesized as described by Beaucage, et al., Tetrahedron Letters, 22:1859-1862, 1981. One method for synthesising oligonucleotides on a modified solid support is described in U.S. Pat. No. 4,458,066.

The agent for polymerisation may be any compound or system which will function to accomplish the synthesis of primer extension products, including enzymes. Suitable enzymes for this purpose include, for example, E. coli DNA polymerase I, Klenow fragment of E. coli DNA polymerase, polymerase muteins, reverse transcriptase, other enzymes, including heat-stable enzymes (ie, those enzymes which perform primer extension after being subjected to temperatures sufficiently elevated to cause denaturation), such as Taq polymerase. Suitable enzyme will facilitate combination of the nucleotides in the proper manner to form the primer extension products that are complementary to each CCDC95 gene sequence nucleic acid strand. Generally, the synthesis will be initiated at the 3' end of each primer and proceed in the 5' direction along the template strand, until synthesis terminates, producing molecules of different lengths.

The newly synthesised CCDC95 strand and its complementary nucleic acid strand will form a double-stranded molecule under hybridizing conditions described above and this hybrid is used in subsequent steps of the process. In the next step, the newly synthesized CCDC95 double-stranded molecule is subjected to denaturing conditions using any of the procedures described above to provide single-stranded molecules.

The steps of denaturing, annealing, and extension product synthesis can be repeated as often as needed to amplify the target polymorphic gene sequence nucleic acid sequence to the extent necessary for detection. The amount of the specific nucleic acid sequence produced will accumulate in an exponential fashion.

Amplification is described in PCR. A Practical Approach, ILR Press, Eds. M. J. McPherson, P. Quirke, and G. R. Taylor, 1992.

The CCDC95 amplification products may be detected by Southern blots analysis, without using radioactive probes. In such a process, for example, a small sample of DNA containing a very low level of the nucleic acid sequence of the CCDC95 gene sequence is amplified, and analyzed via a Southern blotting technique or similarly, using dot blot analysis. The use of non-radioactive probes or labels is facilitated by the high level of the amplified signal. Alternatively, probes used to detect the amplified products can be directly or indirectly detectably labeled, as described herein.

Sequences amplified by the methods of the invention can be further evaluated, detected, cloned, sequenced, and the like, either in solution or after binding to a solid support, by any method usually applied to the detection of a specific DNA sequence such as PCR, oligomer restriction (Saiki, et. al., Bio/Technology, 3:1008-1012, 1985), allele-specific oligonucleotide (ASO) probe analysis (Conner, et. al., Proc. Natl. Acad. Sci. U.S.A., 80:278, 1983), oligonucleotide ligation assays (OLAs) (Landgren, et. al., Science, 241:1007, 1988), and the like. Molecular techniques for DNA analysis have been reviewed (Landgren, et. al., Science, 242:229-237, 1988).

Preferably, the method of amplifying CCDC95 is by PCR, as described herein and as is commonly used by those of ordinary skill in the art. Alternative methods of, amplification have been described and can also be employed as long as the CCDC95 gene sequence amplified by PCR using primers of the invention is similarly amplified by the alternative means. Such alternative amplification systems include but are not limited to self-sustained sequence replication, which begins with a short sequence of RNA of interest and a T7 promoter. Reverse transcriptase copies the RNA into cDNA and degrades the RNA, followed by reverse transcriptase polymerizing a second strand of DNA. Another nucleic acid amplification technique is nucleic acid sequence-based amplification (NASBA) which uses reverse transcription and T7 RNA polymerase and incorporates two primers to target its cycling scheme. NASBA can begin with either DNA or RNA and finish with either, and amplifies to $10^8$ copies within 60 to 90 minutes. Alternatively, nucleic acid can be amplified by ligation activated transcription (LAT). LAT works from a single-stranded template with a single primer that is partially single-stranded and partially double-stranded. Amplification is initiated by ligating a cDNA to the promoter oligonucleotide and within a few hours, amplification is $10^8$ to $10^9$ fold. The QB replicase system can be utilized by attaching an RNA sequence called MDV-1 to RNA complementary to a DNA sequence of interest. Upon mixing with a sample, the hybrid RNA finds its complement among the specimen's mRNAs and binds, activating the replicase to copy the tag-along sequence of interest. Another nucleic acid amplification technique, ligase chain reaction (LCR), works by using two differently labeled halves of a sequence of interest that are covalently bonded by ligase in the presence of the contiguous sequence in a sample, forming a new target. The repair chain reaction (RCR) nucleic acid amplification technique uses two complementary and target-specific oligonucleotide probe pairs, thermostable polymerase and ligase, and DNA nucleotides to geometrically amplify targeted sequences. A 2-base gap separates the oligonucleotide probe pairs, and the RCR fills and joins the gap, mimicking normal DNA repair. Nucleic acid amplification by strand displacement activation (SDA) utilizes a short primer containing a recognition site for hincII with short overhang on the 5' end that binds to target DNA. A DNA polymerase fills in the part of the primer opposite the overhang with sulfur-containing adenine analogs. HincII is added but only cuts the unmodified DNA strand. A DNA polymerase that lacks 5' exonuclease activity enters at the site of the nick and begins to polymerize, displacing the initial primer strand downstream and building a new one which serves as more primer. SDA produces greater than $10^7$-fold amplification in 2 hours at 37 degrees C. Unlike PCR and LCR, SDA does not require instrumented temperature cycling. Another amplification system useful in the method of the invention is the QB Replicase System. Although PCR is the preferred method of amplification if the invention, these other methods can also be used to amplify the CCDC95 gene sequence as described in the method of the invention.

Large amounts of the polynucleotides of the present invention may also be produced by replication in a suitable host cell. Natural or synthetic polynucleotide fragments coding for a desired fragment will be incorporated into recombinant polynucleotide constructs, usually DNA constructs, capable of introduction into and replication in a prokaryotic or eucaryotic cell. Usually the polynucleotide constructs will be suitable for replication in a unicellular host, such as yeast or bacteria, but may also be intended for introduction to (with and without integration within the genome) cultured mammalian or plant or other eucaryotic cell lines.

A double-stranded fragment may be obtained from the single-stranded product of chemical synthesis either by synthesizing the complementary strand and annealing the strands together under appropriate conditions or by adding the complementary strand using DNA polymerase with an appropriate primer sequence.

Nucleic Acid Constructs and Vectors

Polynucleotides of the invention may be incorporated into a recombinant replicable vector for introduction into a prokaryotic or eucaryotic host. Such vectors may typically comprise a replication system recognized by the host, including the intended polynucleotide fragment encoding the desired polypeptide, and will preferably also include transcription and translational initiation regulatory sequences operably linked to the polypeptide encoding segment. Expression vectors may include, for example, an origin of replication or autonomously replicating sequence (ARS) and expression control sequences, a promoter, an enhancer and necessary processing information sites, such as ribosome-binding sites, RNA splice sites, polyadenylation sites, transcriptional terminator sequences, and mRNA stabilizing sequences. localization signals may also be included where appropriate, whether from a native CCDC95 protein or from other receptors or from secreted polypeptides of the same or related species, which allow the protein to cross and/or lodge in cell membranes, and thus attain its functional topology. The localization signal may be a myristoylation signal. The localization signals may be used to target the CCDC95 protein or peptide to distinct cellular domains to modulate a RGK small GTP-binding protein population in different subcellular locations. Further fusion proteins capable of regulating dimerization such as FKBP may be included in a plasmid to facilitate localized dimerization in the presence of rapamycin or FK506 or any other immunosuppressive drugs that naturally act as dimerizers of FKBP and mTOR. Such vectors may be prepared by means of standard recombinant techniques well known in the art and discussed, for example, in Sambrook et al., 1989 supra or Ausubel et al. 1992 supra.

An appropriate promoter and other necessary vector sequences will be selected so as to be functional in the host, and may include, when appropriate, those naturally associated with CCDC95 genes. Examples of workable combinations of cell lines and expression vectors are described in Sambrook et al., 1989 or Ausubel et al., 1992. Many useful vectors are known in the art and may be obtained from such vendors as Stratagene, New England Biolabs, Promega Biotech, and others. Promoters such as the trp, lac and phage promoters, tRNA promoters and glycolytic enzyme promoters may be used in prokaryotic hosts. Useful yeast promoters include promoter regions for metallothionein, 3-phosphoglycerate kinase or other glycolytic enzymes such as enolase or glyceraldehyde-3-phosphate dehydrogenase, enzymes responsible for maltose and galactose utilization, and others. Vectors and promoters suitable for use in yeast expression are further described in Hitzeman et al., EP 73,675A. Appropriate non-native mammalian promoters might include the early and late promoters from SV40 or promoters derived from murine Moloney leukemia virus, mouse tumour virus, avian sarcoma viruses, adenovirus II, bovine papilloma virus or polyoma. In addition, the construct may be joined to an amplifiable gene (e.g., DHFR) so that multiple copies of the gene may be made. For appropriate enhancer and other expression control sequences.

While such expression vectors may replicate autonomously, they may also replicate by being inserted into the genome of the host cell, by methods well known in the art.

Expression and cloning vectors will likely contain a selectable marker, a gene encoding a protein necessary for survival or growth of a host cell transformed with the vector. The presence of this gene ensures growth of only those host cells that express the inserts. Typical selection genes encode proteins that a) confer resistance to antibiotics or other toxic substances, e.g. ampicillin, neomycin, methotrexate, etc.; b) complement auxotrophic deficiencies, or c) supply critical nutrients not available from complex media, e.g., the gene encoding D-alanine racemase for Bacilli. The choice of the proper selectable marker will depend on the host cell, and appropriate markers for different hosts are well known in the art.

The vectors containing the nucleic acids of interest can be transcribed in vitro, and the resulting RNA introduced into the host cell by well-known methods, e.g., by injection, or the vectors can be introduced directly into host cells by methods well known in the art, which vary depending on the type of cellular host, including electroporation; transfection employing calcium chloride, rubidium chloride, calcium phosphate, DEAE-dextran, or other substances; microprojectile bombardment; lipofection; infection (where the vector is an infectious agent, such as a retroviral genome); and other methods. The introduction of the polynucleotides into the host cell by any method known in the art, including, inter alia, those described above, will be referred to herein as "transformation." The cells into which have been introduced nucleic acids described above are meant to also include the progeny of such cells.

Thus the present invention provides host cells transformed or transfected with a nucleic acid molecule of the invention.

Preferred host cells include bacteria, yeast, mammalian cells, plant cells, insect cells, and human cells in tissue culture. Illustratively, such host cells are selected from the group consisting of *E. coli, Pseudomonas, Bacillus, Streptomyces*, yeast, CHO, R1.1, B-W, L-M, COS 1. COS 7, BSC1, BSC40, BMT10, and Sf9 cells.

Large quantities of the nucleic acids and polypeptides of the present invention may be prepared by expressing the CCDC95 nucleic acids or portions thereof in vectors or other expression vehicles in compatible prokaryotic or eucaryotic host cells. The most commonly used prokaryotic hosts are strains of *Escherichia coli*, although other prokaryotes, such as *Bacillus subtilis* or *Pseudomonas* may also be used.

Also provided are mammalian cells containing a CCDC95 polypeptide encoding DNA sequence and modified in vitro to permit higher expression of CCDC95 polypeptide by means of a homologous recombinational event consisting of inserting an expression regulatory sequence in functional proximity to the CCDC95 polypeptide encoding sequence. The expression regulatory sequence can be an CCDC95 polypeptide expression or not and can replace a mutant CCDC95 polypeptide regulatory sequence in the cell.

Thus, the present invention also provides methods for preparing an CCDC95 polypeptide comprising: (a) culturing a cell as described above under conditions that provide for expression of the CCDC95 polypeptide; and (b) recovering the expressed CCDC95 polypeptide. This procedure can also be accompanied by the steps of: (c) chromatographing the polypeptide using any suitable means known in the art; and (d) purifying the polypeptide by for example gel filtration.

Mammalian or other eucaryotic host cells, such as those of yeast, filamentous fungi, plant, insect, or amphibian or avian species, may also be useful for production of the proteins of the present invention. Propagation of mammalian cells in culture is per se well known. Examples of commonly used mammalian host cell lines are VERO and HeLa cells, Chinese hamster ovary (CHO) cells, and WI38, BHK, and COS cell lines, although it will be appreciated by the skilled practitioner that other cell lines may be appropriate, e.g., to provide higher expression, desirable glycosylation patterns, or other features.

Clones are selected by using markers depending on the mode of the vector construction. The marker may be on the same or a different DNA molecule, preferably the same DNA molecule. In procaryotic hosts, the transformant may be selected, e.g., by resistance to ampicillin, tetracycline or other antibiotics. Production of a particular product based on temperature sensitivity may also serve as an appropriate marker.

Procaryotic or eucaryotic cells transformed with the polynucleotides of the present invention will be useful not only for the production of the nucleic acids and polypeptides of the present invention, but also, for example, in studying the The vector can be designed to downregulate CCDC95 in host cells. Such a vector can be used to generate either cell cultures or knockout systems such as mouse models. Such cultures or models may provide systems to study the role of CCDC95 or screen for compounds that can compensate for the loss in CCDC95.

CCDC95 Polypeptides

Full length CCDC95 polypeptides of the present invention have about 250 amino acids, encode a modulator of RGK small GTP-binding protein in an animal, particularly a mammal, and include allelic variants or homologues. Full length CCDC95 polypeptides also typically comprise a coiled-coil domain and a nuclear localisation sequence (as defined below). CCDC95 polypeptides of the invention also include fragments and derivatives of full length CCDC95 polypeptides, particularly fragments or derivatives having substantially the same biological activity. The polypeptides can be prepared by recombinant or chemical synthetic methods. Presently preferred CCDC95 polypeptides include those comprising the amino acid sequence of SEQ ID NOS: 2, 4 and 6, or allelic variants or homologues, including fragments, thereof. A particularly preferred polypeptide consists of amino acids 1 to 70 of the amino acid sequence shown as SEQ ID NO: 2 or allelic variants, homologues or fragments, thereof.

The term "polypeptide" refers to a polymer of amino acids and its equivalent and does not refer to a specific length of the product; thus, peptides, oligopeptides and proteins are included within the definition of a polypeptide. This term also does not refer to, or exclude modifications of the polypeptide, for example, glycosylations, acetylations, phosphorylations, and the like. Included within the definition are, for example, polypeptides containing one or more analogs of an amino acid (including, for example, natural amino acids, etc.), polypeptides with substituted linkages as well as other modifications known in the art, both naturally and non-naturally occurring.

In the context of the present invention, a homologous sequence is taken to include an amino acid sequence which is at least 60, 70, 80 or 90% identical, preferably at least 95 or 98% identical at the amino acid level over at least 20, 50, 100, 200, 300 or 400 amino acids with the amino acid sequences set out in SEQ ID. NOS: 2, 4 or 6. In particular, homology should typically be considered with respect to those regions of the sequence known to be essential for the function of the protein rather than non-essential neighbouring sequences. Thus, for example, homology comparisons are preferably made over regions corresponding to the transmembrane domain, Domain I, Domain II and/or N glycosylation site of the CCDC95 amino acid sequence set out in SEQ ID NOS: 2, 4 or 6. The transmembrane domain corresponds to approximately amino acids 41 to 66 of SEQ ID NO:2. The Domain I corresponds to approximately amino acids 422 to 442 of SEQ ID NO: 2. The Domain II corresponds to approximately amino acids 525 to 563 of SEQ ID NO:2. The glycosylation site corresponds to approximately amino acid 25 of SEQ ID NO:2. Preferred polypeptides of the invention comprise a contiguous sequence having greater than 50, 60 or 70% homology, more preferably greater than 80 or 90% homology, to one or more of amino acids 25, 41 to 66, 422 to 442 or 525 to 563 of SEQ ID NO: 2 or the corresponding regions of SEQ ID NO: 4 or 6. Preferred polypeptides may alternatively or in addition comprise a contiguous sequence having greater than 80 or 90% homology, to amino acids 422 to 442 of SEQ ID NO: 2 or the corresponding region of SEQ ID NO: 4 or 6.

Other preferred polypeptides comprise a contiguous sequence having greater than 40, 50, 60, or 70% homology, more preferably greater than 80 or 90% homology to amino acids 25, 41 to 66, 422 to 442, and/or 525 to 563 of SEQ ID No: 2 or the corresponding regions of SEQ ID NO: 4 or 6. Although homology can also be considered in terms of similarity (i.e. amino acid residues having similar chemical properties/functions), in the context of the present invention it is preferred to express homology in terms of sequence identity. The terms "substantial homology" or "substantial identity", when referring to polypeptides, indicate that the polypeptide or protein in question exhibits at least about 70% identity with an entire naturally-occurring protein or a portion thereof, usually at least about 80% identity, and preferably at least about 90 or 95% identity.

Homology comparisons can be conducted by eye, or more usually, with the aid of readily available sequence comparison programs. These commercially available computer programs can calculate % homology between two or more sequences.

Percentage (%) homology may be calculated over contiguous sequences, i.e. one sequence is aligned with the other sequence and each amino acid in one sequence directly compared with the corresponding amino acid in the other sequence, one residue at a time. This is called an "ungapped" alignment. Typically, such ungapped alignments are performed only over a relatively short number of residues (for example less than 50 contiguous amino acids).

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example when using the GCG Wisconsin Bestfit package (see below) the default gap penalty for amino acid sequences is −12 for a gap and −4 for each extension.

Calculation of maximum % homology therefore firstly requires the production of an optimal alignment, taking into consideration gap penalties. A suitable computer program for carrying out such an alignment is the GCG Wisconsin Bestfit package (University of Wisconsin, U.S.A.; Devereux et al., 1984, Nucleic Acids Research 12:387). Examples of other software that can perform sequence comparisons include, but are not limited to, the BLAST package (see Ausubel et al., 1999 ibid—Chapter 18), FASTA (Atschul et al., 1990, J. Mol. Biol., 403-410) and the GENEWORKS suite of comparison tools. Both BLAST and FASTA are available for offline and online searching (see Ausubel et al., 1999 ibid, pages 7-58 to 7-60). However it is preferred to use the GCG Bestfit program.

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see user manual for further details). It is preferred to use the public default values for the GCG package, or in the case of other software, the default matrix, such as BLOSUM62.

Once the software has produced an optimal alignment, it is possible to calculate % homology, preferably % sequence identity. The software typically does this as part of the sequence comparison and generates a numerical result.

CCDC95 polypeptide homologues include those having the amino acid sequences, wherein one or more of the amino acids is substituted with another amino acid which substitutions do not substantially alter the biological activity of the molecule. An CCDC95 polypeptide homologue according to the invention preferably has 80 percent or greater amino acid sequence identity to the human CCDC95 polypeptide amino acid sequence set out in SEQ ID NO: 6. Examples of CCDC95 polypeptide homologues within the scope of the invention include the amino acid sequence of SEQ ID NOS: 6 wherein: (a) one or more aspartic acid residues is substituted with glutamic acid; (b) one or more isoleucine residues is substituted with leucine; (c) one or more glycine or valine residues is substituted with alanine; (d) one or more arginine residues is substituted with histidine; or (e) one or more tyrosine or phenylalanine residues is substituted with tryptophan.

"CCDC95 protein" or "CCDC95 polypeptide" refers to a protein or polypeptide encoded by the CCDC95 gene sequence, variants or fragments thereof. Also included are proteins encoded by DNA that hybridize under high or low stringency conditions, to CCDC95 encoding nucleic acids and closely related polypeptides or proteins retrieved by antisera to the CCDC95 protein(s).

"Protein modifications or fragments" are provided by the present invention for CCDC95 polypeptides or fragments thereof which are substantially homologous to primary structural sequence but which include, e.g., in vivo or in vitro chemical and biochemical modifications or which incorporate unusual amino acids. Such modifications include, for example, acetylation, carboxylation, phosphorylation, glycosylation, ubiquitination, labeling, e.g., with radionuclides, and various enzymatic modifications, as will be readily appreciated by those well skilled in the art. A variety of methods for labeling polypeptides and of substituents or labels useful for such purposes are well known in the art, and include radioactive isotopes such as $^{32}$P, ligands which bind to labeled antiligands (e.g., antibodies), fluorophores, chemiluminescent agents, enzymes, and antiligands which can serve as specific binding pair members for a labeled ligand. The choice of label depends on the sensitivity required, ease of conjugation with the primer, stability requirements, and available instrumentation. Methods of labeling polypeptides are well known in the art. See, e.g., Sambrook et al., 1989 supra or Ausubel et al., 1992 supra.

A polypeptide "fragment," "portion" or "segment" is a stretch of amino acid residues of at least about five to seven contiguous amino acids, often at least about seven to nine contiguous amino acids, typically at least about nine to 13 contiguous amino acids and, most preferably, at least about 20 to 30 or more contiguous amino acids.

Preferred polypeptides of the invention have substantially similar function to wild type full length CCDC95. Preferred polynucleotides of the invention encode polypeptides having substantially similar function to wild type full length CCDC95. "Substantially similar function" refers to the function of a nucleic acid or polypeptide homologue, variant, derivative or fragment of CCDC95 with reference to the wild-type CCDC95 nucleic acid or wild-type CCDC95 polypeptide.

However, non-functional forms of CCDC95 polypeptides may also be included within the scope of the invention since they may be useful, for example, as antagonists of CCDC95 function.

In addition to the similarity of function, the modified polypeptide may have other useful properties, such as a longer half-life. The similarity of function (activity) of the modified polypeptide may be substantially the same as the activity of the wild-type CCDC95 polypeptide. Alternatively, the similarity of function (activity) of the modified polypeptide may be higher than the activity of the wild-type CCDC95 polypeptide. The function/biological activity of homologues, variant, derivatives or fragments relative to wild type may be determined, for example, by means of biological assays. For example, when administered to stem cells, CCDC95 initiates myoblast differentiation, resulting in an increase in myoblasts. Thus one test for CCDC95 activity is to administer a variant to stem cells and determine whether myoblast differentiation results. Preferred homologues, variants and fragments are capable of initiating differentiation by a factor of at least 0.5 relative to full length CCDC95, preferably by a factor of at least 0.9. Another test, based on the interaction of CCDC95 with the NLS domain of kir/Gem to determine the extent of binding of a homologue, variant or fragment to the NLS binding domain of Kir/Gem in an in vitro binding assay. Preferred homologues, variants and fragments are capable of binding to the NLS binding domain of Kir/Gem by a factor of at least 0.5 relative to full length CCDC95, preferably by a factor of at least 0.9. Suitable in vitro binding assays are well known to skilled persons, such as GST 'pulldown' assays where one component is expressed as a fusion protein linked to glutathione-S-transferase an immobilized on glutathione-sepharose beads.

The modified polypeptide may be synthesised using conventional techniques, or is encoded by a modified nucleic acid and produced using conventional techniques. The modified nucleic acid is prepared by conventional techniques. A nucleic acid with a function substantially similar to the wild-type CCDC95 gene function produces the modified protein described above.

Besides substantially full-length polypeptides, the present invention provides for biologically active fragments of the polypeptides. Significant biological activities include ligand-binding, such as binding to the NLS binding domain of Kir/Gem or other identified RGK small binding protein interacting molecules, modulation of RGK small binding protein and other biological activities characteristic of CCDC95 polypeptides.

The polypeptides of the present invention, if soluble, may be coupled to a solid-phase support, e.g., nitrocellulose, nylon, column packing materials (e.g., Sepharose beads), magnetic beads, glass wool, plastic, metal, polymer gels, cells, or other substrates. Such supports may take the form, for example, of beads, wells, dipsticks, or membranes.

The present invention also provides for fusion polypeptides, comprising CCDC95 polypeptides and fragments. Homologous polypeptides may be fusions between two or more CCDC95 polypeptide sequences or between the sequences of CCDC95 and a related protein. Likewise, heterologous fusions may be constructed which would exhibit a combination of properties or activities of the derivative proteins. For example, ligand-binding or other domains may be "swapped" between different new fusion polypeptides or fragments. Such homologous or heterologous fusion polypeptides may display, for example, altered strength or specificity of binding. Fusion partners include immunoglobulins, bacterial .beta.-galactosidase, trpE, protein A, .beta.-lactamase, alpha amylase, alcohol dehydrogenase and yeast alpha mating factor.

Fusion proteins will typically be made by either recombinant nucleic acid methods, as described below, or may be chemically synthesized.

"Protein purification" refers to various methods for the isolation of the CCDC95 polypeptides from other biological material, such as from cells transformed with recombinant nucleic acids encoding CCDC95, and are well known in the art. For example, such polypeptides may be purified by immuno-affinity chromatography employing, e.g., the antibodies provided by the present invention. Various methods of protein purification are well known in the art.

The terms "isolated", "substantially pure", and "substantially homogeneous" are used interchangeably to describe a protein or polypeptide that has been separated from components that accompany it in its natural state. A monomeric protein is substantially purified when at least about 60 to 75% of a sample exhibits a single polypeptide sequence. A substantially purified protein will typically comprise about 60 to 90% W/W of a protein sample, more usually about 95%, and preferably will be over about 99% pure. Protein purity or homogeneity may be indicated by a number of means well known in the art, such as polyacrylamide gel electrophoresis of a protein sample, followed by visualizing a single polypeptide band upon staining the gel. For certain purposes, higher resolution may be provided by using HPLC or other means well known in the art which are utilized for application.

A CCDC95 protein is substantially free of naturally associated components when it is separated from the native contaminants that accompany it in its natural state. Thus, a polypeptide that is chemically synthesised or synthesised in a cellular system different from the cell from which it naturally originates will be substantially free from its naturally associated components. A protein may also be rendered substantially free of naturally associated components by isolation, using protein purification techniques well known in the art.

A polypeptide produced as an expression product of an isolated and manipulated genetic sequence is an "isolated polypeptide," as used herein, even if expressed in a homologous cell type. Synthetically made forms or molecules expressed by heterologous cells are inherently isolated molecules.

Diagnosis

The expression of CCDC95 varies in certain tissue types. This may be due to mutations in CCDC95 may be implicated in conditions related to RGK small binding protein disfunction. Consequently, establishing the CCDC95 status of an individual may be a useful diagnostic and/or prognostic tool.

Diagnostic and prognostic methods will generally be conducted using a biological sample obtained from a patient. A "sample" refers to a sample of tissue or fluid suspected of containing an analyte polynucleotide or polypeptide from an individual including, but not limited to, e.g., plasma, serum, spinal fluid, lymph fluid, the external sections of the skin, respiratory, intestinal, and genitourinary tracts, tears, saliva, blood cells, organs, tissue and samples of in vitro cell culture constituents.

According to the diagnostic and prognostic methods of the present invention, alteration of the wild-type CCDC95 gene sequence may be detected using anyone of the methods described herein. In addition, the diagnostic and prognostic methods can be performed to detect the wild-type CCDC95 gene sequence and confirm a lack of a predisposition to a disorder related to RGK small binding protein at the CCDC95 gene sequence.

"Alteration of a wild-type gene" encompasses all forms of mutations including deletions, insertions and point mutations in the coding and noncoding regions. Deletions may be of the entire gene or of only a portion of the gene. Point mutations may result in stop codons, frameshift mutations or amino acid substitutions. Somatic mutations are those that occur only in certain tissues, e.g., in pancreatic islets, pituitary, cerebrum, cerebellum or heart cells and are not inherited in the germline. Germline mutations can be found in any of a body's tissues and are inherited. If only a single CCDC95 allele is somatically mutated, a disorder related to RGK small binding protein may be indicated. The finding of CCDC95 mutations thus provides both diagnostic and prognostic information. A CCDC95 gene sequence that is not deleted can be screened for other mutations, such as insertions, small deletions, and point mutations.

The predisposition of a patient to disorders related to voltage gated calcium channels, such as ataxia, migraine, epilepsy, neurodegeneration, hypertension, cardiac disorders and diabetes, and other disorders related RGK small binding protein identified herein, can be ascertained by testing any tissue of the patient for mutations of the CCDC95 gene. For example, a person who has inherited a germline CCDC95 mutation might be prone to develop the above disorders. Most simply, blood can be drawn and DNA extracted from the cells of the blood. In addition, prenatal diagnosis can be accomplished by testing fetal cells, placental cells or amniotic cells for mutations of the CCDC95 gene. Alteration of a wild-type CCDC95 allele, whether, for example, by point mutation or deletion, can be detected by any of the means discussed herein.

To detect the alteration of the wild-type CCDC95 gene in a tissue, it is helpful to isolate the tissue free from surrounding normal tissues. Means for enriching tissue preparation are known in the art. For example, the tissue may be isolated from paraffin or cryostat sections. Cells may also be separated by flow cytometry.

A rapid preliminary analysis to detect polymorphisms in DNA sequences can be performed by looking at a series of Southern blots of DNA cut with one or more restriction enzymes, preferably with a large number of restriction enzymes. Each blot contains a series of normal individuals and a series of individuals with disorders related to voltage gated calcium channels, RGK small binding protein, or all of these. Southern blots displaying hybridising fragments (differing in length from control DNA when probed with sequences near or including the CCDC95 gene sequence) indicate a possible mutation. If restriction enzymes that produce very large restriction fragments are used, then pulsed field gel electrophoresis (PFGE) may also be employed.

Detection of point mutations may also be accomplished by molecular cloning of the CCDC95 allele(s) and sequencing the allele(s) using techniques well known in the art. Alternatively, the gene sequences can be amplified directly from a genomic DNA preparation from other minor tissue, using known techniques. The most popular method used today is target amplification. Here, the target nucleic acid sequence is amplified with polymerases. One particularly preferred method using polymerase-driven amplification is the polymerase chain reaction (PCR). The polymerase chain reaction and other polymerase-driven amplification assays can achieve over a million-fold increase in copy number through the use of polymerase-driven amplification cycles. Once amplified, the resulting nucleic acid can be sequenced or used as a substrate for DNA probes.

Some other useful diagnostic techniques for detecting the presence of CCDC95 and or mutations to the gene include, but are not limited to: 1) allele-specific PCR; 2) single stranded conformation analysis (SSCA); 3) denaturing gradient gel electrophoresis (DGGE); 4) RNase protection assays; 5) the use of proteins which recognize nucleotide mismatches, such as the *E. coli* mutS protein; 6) allele-specific oligonucleotides (ASOs); and 7) fluorescent in situ hybridisation (FISH). Other approaches based on the detection of mismatches between the two complementary DNA strands include clamped denaturing gel electrophoresis (CDGE), heteroduplex analysis (HA) and chemical mismatch cleavage (CMC).

For allele-specific PCR, primers are used which hybridize at their 3' ends to a particular CCDC95 mutation. If the particular CCDC95 mutation is not present, an amplification product is not observed. Amplification Refractory Mutation System (ARMS) can also be used, as disclosed in European Patent Application Publication No. 0332435. Insertions and deletions of genes can also be detected by cloning, sequencing and amplification. In addition, restriction fragment length polymorphism (RFLP) probes for the gene or surrounding marker genes can be used to score alteration of an allele or an insertion in a polymorphic fragment. Such a method is particularly useful for screening relatives of an affected individual for the presence of the CCDC95 mutation found in that individual.

SSCA detects a band which migrates differentially because the sequence change causes a difference in single-strand, intramolecular base pairing. This method does not detect all sequence changes, especially if the DNA fragment size is greater than 200 bp, but can be optimized to detect most DNA sequence variation. The reduced detection sensitivity is a disadvantage, but the increased throughput possible with SSCA makes it an attractive, viable alternative to direct sequencing for mutation detection on a research basis. The fragments that have shifted mobility on SSCA gels are then sequenced to determine the exact nature of the DNA sequence variation.

DGGE detects differences in migration rates of mutant sequences compared to wild-type sequences, using a denaturing gradient gel.

In the RNase protection method a labeled riboprobe that is complementary to the human wild-type CCDC95 gene coding sequence is used. The riboprobe and either mRNA or DNA isolated from the effected tissue are hybridised together and subsequently digested with the enzyme RNase A that is able to detect some mismatches in a duplex RNA structure. If a mismatch is detected by RNase A, it cleaves at the site of the mismatch. Thus, when the annealed RNA preparation is separated on an electrophoretic gel matrix, if a mismatch has been detected and cleaved by RNase A, an RNA product will be seen which is smaller than the full length duplex RNA for the riboprobe and the mRNA or DNA. The riboprobe need not be the full length of the CCDC95 mRNA or gene but can be a segment of either. If the riboprobe comprises only a segment of the CCDC95 mRNA or gene, it will be desirable to use a number of these probes to screen the whole mRNA sequence for mismatches.

In similar fashion, DNA probes can be used to detect mismatches, through enzymatic or chemical cleavage. Alternatively, mismatches can be detected by shifts in the electrophoretic mobility of mismatched duplexes relative to matched duplexes. With either riboprobes or DNA probes, the cellular mRNA or DNA that might contain a mutation can be amplified using PCR (see below) before hybridisation.

In the mutS assay, the protein binds only to sequences that contain a nucleotide mismatch in a heteroduplex between mutant and wild-type sequences.

Once a mutation is known, a gene specific detection approach such as allele specific oligonucleotide (ASO) hybridisation can be utilised to rapidly screen large numbers of samples for that same mutation. In an allele-specific oligonucleotide assay, an oligonucleotide is designed which detects a specific sequence which contains a region of the CCDC95 gene sequence harboring a known mutation, and the assay is performed by detecting the presence or absence of a hybridisation signal. For example, one oligomer may be about 30 nucleotides in length, corresponding to a portion of the CCDC95 gene sequence possibly in Domain I or Domain II. By use of a battery of such allele-specific probes, PCR amplification products can be screened to identify the presence of a previously identified mutation in the CCDC95 gene. Hybridisation of allele-specific probes with amplified CCDC95 sequences can be performed, for example, on a nylon filter. Hybridisation to a particular probe under stringent hybridisation conditions indicates the presence of the same mutation in the tissue with disrupted RGK small binding protein activity as in the allele-specific probe.

In addition to the above methods CCDC95 genes and mutants thereof may be detected using conventional probe technology. When probes are used to detect the presence of the target sequences (for example, in screening for susceptibility to disorders related to RGK small binding protein irregularity), the biological sample to be analysed, such as blood or serum, may be treated, if desired, to extract the nucleic acids. The sample nucleic acid may be prepared in various ways to facilitate detection of the target sequence; e.g. denaturation, restriction digestion, electrophoresis or dot blotting. The targeted region of the sample nucleic acid usually must be at least partially single-stranded to form hybrids with the targeting sequence of the probe. If the sequence is naturally single-stranded, denaturation will not be required. However, if the sequence is double-stranded, the sequence will probably need to be denatured. Denaturation can be carried out by various techniques known in the art.

Sample nucleic acid and probe are incubated under conditions that promote stable hybrid formation of the target sequence in the probe with the putative targeted sequence in the sample. The region of the probes that is used to bind to the sample can be made completely complementary to the targeted region of the human chromosomal location for CCDC95. Therefore, high stringency conditions are desirable in order to prevent false positives. However, conditions of high stringency may be used only if the probes are complementary to regions of the chromosome that are unique in the genome. The stringency of hybridisation is determined by a number of factors during hybridisation and during the washing procedure, including temperature, ionic strength, base composition, probe length, and concentration of formamide. Under certain circumstances, the formation of higher order hybrids, such as triplexes, quadraplexes, etc., may be desired to provide the means of detecting target sequences.

Detection, if any, of the resulting hybrid is usually accomplished by the use of labeled probes. Alternatively, the probe may be unlabeled, but may be detectable by specific binding with a ligand that is labeled, either directly or indirectly. Suitable labels, and methods for labeling probes and ligands are known in the art, and include, for example, radioactive labels which may be incorporated by known methods (e.g., nick translation, random priming or kinasing), biotin, fluorescent groups, chemiluminescent groups (e.g., dioxetanes, particularly triggered dioxetanes), enzymes, antibodies and the like. Variations of this basic scheme are known in the art, and include those variations that facilitate separation of the hybrids to be detected from extraneous materials and/or that amplify the signal from the labeled moiety.

Two detection methodologies that are particularly effective, work on the principle that a small ligand (such as digoxigenin, biotin, or the like) is attached to a nucleic acid probe capable of specifically binding CCDC95. The small ligand is then detected. In one example, the small ligand attached to the nucleic acid probe might be specifically recognized by an antibody-enzyme conjugate. For example, digoxigenin may be attached to the nucleic acid probe. Hybridisation is then detected by an antibody-alkaline phosphatase conjugate that turns over a chemiluminescent substrate. In a second example, the small ligand may be recognized by a second ligand-enzyme conjugate that is capable of specifically complexing to the first ligand. A well-known example is the biotin-avidin type of interactions.

It is also contemplated within the scope of this invention that the nucleic acid probe assays of this invention will employ a cocktail of nucleic acid probes capable of detecting CCDC95. Thus, in one example to detect the presence of CCDC95 in a cell sample, more than one probe complementary to CCDC95 is employed and in particular the number of different probes is alternatively 2, 3, or 5 different nucleic acid probe sequences. In another example, to detect the presence of mutations in the CCDC95 gene sequence in a patient, more than one probe complementary to CCDC95 is employed where the cocktail includes probes capable of binding to the allele-specific mutations identified in populations of patients with alterations in CCDC95. In this embodiment, any number of probes can be used, and will preferably include probes corresponding to the major gene mutations identified as predisposing an individual to the cancerous states described herein.

In a highly preferred embodiment, screening techniques based on hybridization to probes, particularly a plurality of probes that correspond to allele-specific mutations use probes immobilized to solid substrates as described above, for example in the form of DNA arrays on silicon substrates (DNA chips).

Alteration of wild-type CCDC95 genes can also be detected by screening for alteration of wild-type CCDC95 protein. Such alterations can be determined by amino acid sequence analysis in accordance with conventional techniques. More preferably, antibodies (polyclonal or monoclonal) may be used to detect differences in, or the absence of CCDC95 proteins or peptides. The antibodies may be prepared as discussed below under the heading "Antibodies". For example, monoclonal antibodies immunoreactive with CCDC95 can be used to screen a tissue. Lack of cognate antigen may indicate a CCDC95 mutation, expression or prostranslation deficiency. Antibodies specific for products of mutant alleles could also be used to detect mutant CCDC95 gene product. Such immunological assays can be done in any convenient format known in the art. These include Western blots, immunohistochemical assays and ELISA assays. Any means for detecting an altered CCDC95 protein can be used to detect alteration of wild-type CCDC95 genes. Functional assays, such as protein binding determinations, can be used. In addition, assays can be used which detect CCDC95 biological function. Finding a mutant CCDC95 gene product indicates alteration of a wild-type CCDC95 gene.

In a preferred embodiment of the invention, antibodies will immunoprecipitate CCDC95 proteins from solution as well as react with CCDC95 protein on Western or immunoblots of polyacrylamide gels. In another preferred embodiment, antibodies will detect CCDC95 proteins in paraffin or frozen tissue sections, using immunocytochemical techniques.

Preferred embodiments relating to methods for detecting CCDC95 or its mutations include enzyme linked immunosorbent assays (ELISA), radioimmunoassays (RIA), immunoradiometric assays (IRMA) and immunoenzymatic assays (IEMA), including sandwich assays using monoclonal and/or polyclonal antibodies.

Antibodies

The present invention also provides labeled and unlabeled monoclonal and polyclonal antibodies specific for CCDC95 polypeptides of the invention and immortal cell lines that produce a monoclonal antibody of the invention. Antibody preparation according to the invention involves: (a) conjugating an CCDC95 polypeptide to a carrier protein; (b) immunizing a host animal with the CCDC95 polypeptide fragment-carrier protein conjugate of step (a) admixed with an adjuvant; and (c) obtaining antibody from the immunized host animal.

According to the invention, CCDC95 polypeptide produced recombinantly or by chemical synthesis, and fragments or other derivatives or analogs thereof, including fusion proteins, may be used as an immunogen to generate antibodies that recognize the CCDC95 polypeptide. Such antibodies include but are not limited to polyclonal, monoclonal, chimeric, single chain, Fab fragments, and an Fab expression library.

Thus, the present invention also provides polyclonal and/or monoclonal antibodies and fragments thereof, and immunologic binding equivalents thereof, which are capable of specifically binding to the CCDC95 polypeptides and fragments thereof or to polynucleotide sequences from the CCDC95 region, particularly from the CCDC95 gene sequence or a portion thereof. Such antibodies thus include for example, but are not limited to polyclonal, monoclonal, chimeric, single chain, Fab fragments, and an Fab expression library. Production of antibodies specific for CCDC95 polypeptides or fragments thereof is described below.

A molecule is "antigenic" when it is capable of specifically interacting with an antigen recognition molecule of the immune system, such as an immunoglobulin (antibody) or T cell antigen receptor. An antigenic polypeptide contains at least about 5, and preferably at least about 10, amino acids. An antigenic portion of a molecule can be that portion that is immunodominant for antibody or T cell receptor recognition, or it can be a portion used to generate an antibody to the molecule by conjugating the antigenic portion to a carrier molecule for immunization. A molecule that is antigenic need not be itself immunogenic, i.e., capable of eliciting an immune response without a carrier.

An "antibody" is any immunoglobulin, including antibodies and fragments thereof, that binds a specific epitope. The term encompasses polyclonal, monoclonal, and chimeric antibodies, the last mentioned described in further detail in U.S. Pat. Nos. 4,816,397 and 4,816,567, as well as antigen binding portions of antibodies, including Fab, F(ab')$_2$ and F(v) (including single chain antibodies). Accordingly, the phrase "antibody molecule" in its various grammatical forms as used herein contemplates both an intact immunoglobulin molecule and an immunologically active portion of an immunoglobulin molecule containing the antibody combining site. An "antibody combining site" is that structural portion of an antibody molecule comprised of heavy and light chain variable and hypervariable regions that specifically binds antigen.

Exemplary antibody molecules are intact immunoglobulin molecules, substantially intact immunoglobulin molecules and those portions of an immunoglobulin molecule that contains the paratope, including those portions known in the art as Fab, Fab', F(ab')$_2$ and F(v), which portions are preferred for use in the therapeutic methods described herein.

Fab and F(ab')$_2$ portions of antibody molecules are prepared by the proteolytic reaction of papain and pepsin, respectively, on substantially intact antibody molecules by methods that are well-known. See for example, U.S. Pat. No. 4,342,566. Fab' antibody molecule portions are also well-known and are produced from F(ab')$_2$ portions followed by reduction of the disulfide bonds linking the two heavy chain portions as with mercaptoethanol, and followed by alkylation of the resulting protein mercaptan with a reagent such as iodoacetamide. An antibody containing intact antibody molecules is preferred herein.

The phrase "monoclonal antibody" in its various grammatical forms refers to an antibody having only one species of antibody combining site capable of immunoreacting with a particular antigen. A monoclonal antibody thus typically displays a single binding affinity for any antigen with which it immunoreacts. A monoclonal antibody may therefore contain an antibody molecule having a plurality of antibody combining sites, each immunospecific for a different antigen; e.g., a bi-specific (chimeric) monoclonal antibody.

The term "adjuvant" refers to a compound or mixture that enhances the immune response to an antigen. An adjuvant can serve as a tissue depot that slowly releases the antigen and also as a lymphoid system activator that non-specifically enhances the immune response [Hood et al., in *Immunology*, p. 384, Second Ed., Benjamin/Cummings, Menlo Park, Calif. (1984)]. Often, a primary challenge with an antigen alone, in the absence of an adjuvant, will fail to elicit a humoral or cellular immune response. Adjuvants include, but are not limited to, complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions, keyhole limpet hemocyanins, dinitrophenol, and potentially useful human adjuvants such as BCG (bacille Calmette-Guerin) and *Corynebacterium parvum*. Preferably, the adjuvant is pharmaceutically acceptable.

Various procedures known in the art may be used for the production of polyclonal antibodies to CCDC95 polypeptide, or fragment, derivative or analog thereof. For the production of antibody, various host animals can be immunized by injection with the CCDC95 polypeptide, or a derivative (e.g., fragment or fusion protein) thereof, including but not limited to rabbits, mice, rats, sheep, goats, etc. In one embodiment, the CCDC95 polypeptide or fragment thereof can be conjugated to an immunogenic carrier, e.g., bovine serum albumin (BSA) or keyhole limpet hemocyanin (KLH). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*.

For preparation of monoclonal antibodies directed toward the CCDC95 polypeptide, or fragment, analog, or derivative thereof, any technique that provides for the production of antibody molecules by continuous cell lines in culture may be used. These include but are not limited to the hybridoma technique originally developed by Kohler et al., *Nature,* 256: 495-497 (1975), as well as the trioma technique, the human B-cell hybridoma technique [Kozbor et al., *Immunology Today,* 4:72 (1983)], and the EBV-hybridoma technique to produce human monoclonal antibodies [Cole et al., in *Monoclonal Antibodies and Cancer Therapy,* pp. 77-96, Alan R. Liss, Inc., (1985)]. Immortal, antibody-producing cell lines can be created by techniques other than fusion, such as direct transformation of B lymphocytes with oncogenic DNA, or transfection with Epstein-Barr virus. See, e.g., M. Schreier et al., "Hybridoma Techniques" (1980); Hammerling et al., "Monoclonal Antibodies And T-cell Hybridomas" (1981); Kennett et al., "Monoclonal Antibodies" (1980); see also U.S. Pat. Nos. 4,341,761; 4,399,121; 4,427,783; 4,444,887; 4,451,570; 4,466,917; 4,472,500; 4,491,632; and 4,493,890.

In an additional embodiment of the invention, monoclonal antibodies can be produced in germ-free animals utilizing recent technology (PCT/US90/02545). According to the invention, human antibodies may be used and can be obtained by using human hybridomas [Cote et al., *Proc. Natl. Acad. Sci. USA*, 80:2026-2030 (1983)] or by transforming human B cells with EBV virus in vitro (Cole et al., 1985, supra). In fact, according to the invention, techniques developed for the production of "chimeric antibodies" [Morrison et al., *J. Bacteriol.*, 159-870 (1984); Neuberger et al., *Nature*, 312:604-608 (1984); Takeda et al., *Nature*, 314:452-454 (1985)] by splicing the genes from a mouse antibody molecule specific for an CCDC95 polypeptide together with genes from a human antibody molecule of appropriate biological activity can be used; such antibodies are within the scope of this invention. Such human or humanized chimeric antibodies are preferred for use in therapy of human diseases or disorders (described infra), since the human or humanized antibodies are much less likely than xenogenic antibodies to induce an immune response, in particular an allergic response, themselves.

According to the invention, techniques described for the production of single chain antibodies (U.S. Pat. No. 4,946,778) can be adapted to produce CCDC95 polypeptide-specific single chain antibodies. An additional embodiment of the invention utilizes the techniques described for the construction of Fab expression libraries [Huse et al., *Science*, 246:1275-1281 (1989)] to allow rapid and easy identification of monoclonal Fab fragments with the desired specificity for an CCDC95 polypeptide, or its derivatives, or analogs.

Antibody fragments which contain the idiotype of the antibody molecule can be generated by known techniques. For example, such fragments include but are not limited to: the F(ab')$_2$ fragment which can be produced by pepsin digestion of the antibody molecule; the Fab' fragments which can be generated by reducing the disulfide bridges of the F(ab')$_2$ fragment, and the Fab fragments which can be generated by treating the antibody molecule with papain and a reducing agent.

In the production of antibodies, screening for the desired antibody can be accomplished by techniques known in the art, e.g., radioimmunoassay, ELISA (enzyme-linked immunosorbent assay), "sandwich" immunoassays, immunoradiometric assays, gel diffusion precipitin reactions, immunodiffusion assays, in situ immunoassays (using colloidal gold, enzyme or radioisotope labels, for example), Western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. For example, to select antibodies that recognize a specific epitope of a CCDC95 polypeptide, one may assay generated hybridomas for a product that binds to an CCDC95 polypeptide fragment containing such epitope. For selection of an antibody specific to a CCDC95 polypeptide from a particular species of animal, one can select on the basis of positive binding with CCDC95 polypeptide expressed by or isolated from cells of that species of animal.

An exemplary antibody may include an affinity-purified rabbit anti-peptide LQYENVDEDSSDSDA antibody.

The foregoing antibodies can be used in methods known in the art relating to the localization and activity of the CCDC95 polypeptide, e.g., for Western blotting, imaging CCDC95 polypeptide in situ, measuring levels thereof in appropriate physiological samples, etc.

In a specific embodiment, antibodies are developed by immunizing rabbits with synthetic peptides predicted by the protein sequence or with recombinant proteins made using bacterial expression vectors. The choice of synthetic peptides is made after careful analysis of the predicted protein structure, as described above. In particular, peptide sequences between putative cleavage sites are chosen. Synthetic peptides are conjugated to a carrier such as KLH hemocyanin or BSA using carbodiimide and used in Freunds adjuvant to immunize rabbits. In order to prepare recombinant protein, the pGEX vector can be used to express the polypeptide. Alternatively, one can use only hydrophilic domains to generate the fusion protein. The expressed protein will be prepared in quantity and used to immunize rabbits in Freunds adjuvant.

In yet another embodiment, recombinant CCDC95 polypeptide is used to immunize rabbits, and the polyclonal antibodies are immunopurified prior to further use. The purified antibodies are particularly useful for semi-quantitative assays, particularly for detecting the presence of CCDC95 polypeptide.

Preferably, the anti-modulator antibody used in the diagnostic and therapeutic methods of this invention is an affinity-purified polyclonal antibody. More preferably, the antibody is a monoclonal antibody (mAb). In addition, it is preferable for the anti-modulator antibody molecules used herein be in the form of Fab, Fab', F(ab')$_2$ or F(v) portions of whole antibody molecules.

Assays

The present invention provides assays that are suitable for identifying substances that bind to CCDC95 polypeptides (reference to which includes homologues, variants, derivatives and fragments as described above). In addition, assays are provided that are suitable for identifying substances that interfere with CCDC95 binding to the NLS binding domain of RGK small binding protein, for example proteins identified in yeast two-hybrid screens as interacting with CCDC95 (such as the NLS binding domain of kir/Gem). Such assays are typically in vitro. Assays are also provided that test the effects of candidate substances identified in preliminary in vitro assays on intact cells in whole cell assays.

Candidate Substances

A substance that modulates RGK small binding protein activity, concentration and/or subcellular localization as a result of an interaction between CCDC95 polypeptide and RGK small binding protein may do so in several ways. It may directly disrupt the binding of CCDC95 to a RGK small binding protein by, for example, binding to CCDC95 and masking or altering the site of interaction with the other component. Candidate substances of this type may conveniently be preliminarily screened by in vitro binding assays as, for example, described below and then tested, for example in a whole cell assay as described below. Examples of candidate substances include antibodies which recognise CCDC95.

A substance which can bind directly to CCDC95 may also inhibit any interaction between CCDC95 and RGK small binding protein. This may affect nuclear sequestration of RGK small binding protein. This can be tested using, for example the whole cells assays described below. Non-functional homologues of CCDC95 may also be tested for inhibition of CCDC95 activity since they may compete with CCDC95 for binding to a RGK small binding protein. Such non-functional homologues may include naturally occurring CCDC95 mutants and modified CCDC95 sequences or fragments thereof. In particular, fragments of CCDC95 which comprise one or more of the Coiled-coil domain, NLS binding site Helix I, II or III or other functional domains that may be used to compete with full length CCDC95.

Where modulating a RGK small binding protein comprises inhibiting or reducing the RGK small binding protein concentration the modulator may comprise CCDC95 or peptide fragments such as a Coiled-coil domain, NLS binding site Helix I, II or III or a fusion polypeptide of Coiled-coil domain, NLS binding site or Helix I, II or III Preferably the coiled coil Domain is DGEVDYKKKYRNLKRKLKFLIYEHECFQEEL-RKAQRKLLKVSRDKSFLLDRLQYENV DEDSS roughly corresponding to amino acids 6 to 67 of SEQ ID NO: 2 and homologous amino acid sequences of corresponding SEQ ID NOS: 4 or 6. Preferably the coiled coil Domain fragment can interact with a RGK small binding protein thereby inhibiting calcium channel activity. The Coiled-coil domain may further comprise sub-domains such as NLS binding site Helix I, II or III. Preferably the Helix I is VDYKKKYRNLKRKLKF roughly corresponding to amino acids 9 to 24 of SEQ ID NO: 2; the Helix II is IYEHECFQEELRKAQRKLLKV roughly corresponding to amino acids 26 to 46 of SEQ ID NO: 2 and Helix II is KSFLLDRLQYEN roughly corresponding to amino acids 50 to 61 of SEQ ID NO: 2 and homologous amino acid sequences of corresponding SEQ ID NOS: 4 or 6.

Preferably the coiled coil Domain roughly corresponds to amino acids 6 to 67 of SEQ ID NO: 2 eg: DGEVDYKKKYRNLKRKLKFLIYEHECFQEEL-RKAQRKLLKVSRDKSFLLDRLQYENV DEDSS and homologous amino acid fragment sequences of corresponding SEQ ID NOS: 4 or 6. Preferably the coiled coil Domain fragment can interact with a RGK Small binding protein thereby modulating the RGK Small binding protein effecting calcium channel activity, cell morphology and myoblast differentiation.

Alternatively, instead of preventing the association of the components directly, the substance may alter the biologically available amount of CCDC95. This may be by inhibiting expression of the component, for example at the level of transcription, transcript stability, translation or post-translational stability. An example of such a substance would be antisense RNA or double-stranded interfering RNA sequences which suppresses the amount of CCDC95 mRNA biosynthesis. In particular, inhibition of CCDC95 binding to a RGK Small binding protein may decrease the amount of available CCDC95 in a cell.

Suitable candidate substances include peptides, especially of from about 5 to 30 or 10 to 25 amino acids in size, based on the sequence of the various domains of CCDC95 described above, or variants of such peptides in which one or more residues have been substituted. Peptides from panels of peptides comprising random sequences or sequences which have been varied consistently to provide a maximally diverse panel of peptides may be used.

Where modulating a RGK Small binding protein comprises competition for CCDC95 less RGK Small binding protein is sequested to the nucleus affecting changes in cell morphology the modulator may comprise mutated CCDC95 wherein amino acids are deleted from the RGK Small binding protein. Means of knocking out or knocking down RGK Small binding protein may be used including siRNA an RNA interference sequence capable of interfering with RGK Small binding protein gene expression; alternative RNA splicing techniques; posttranslational processing to RGK Small binding protein; the level of expression of RGK Small binding protein including both mRNA expression and protein expression; or any mutation of RGK Small binding protein that effects RGK Small binding protein's expression or journey to the membrane.

Suitable candidate substances also include antibody products (for example, monoclonal and polyclonal antibodies, single chain antibodies, chimeric antibodies and CDR-grafted antibodies) which are specific for CCDC95, the CCDC95 Y15A/Y60A mutant. Furthermore, combinatorial libraries, peptide and peptide mimetics, defined chemical entities, oligonucleotides, and natural product libraries may be screened for activity as regulators of CCDC95 activity. The candidate substances may be used in an initial screen in batches of, for example 10 substances per reaction, and the substances of those batches which show inhibition tested individually. Candidate substances which show activity in in vitro screens such as those described below can then be tested in whole cell systems, such as mammalian cells which will be exposed to the inhibitor and tested for effects on cell growth.

CCDC95 Binding Assays

One type of assay for identifying substances that bind to CCDC95 involves contacting a CCDC95 polypeptide, which is immobilised on a solid support, with a non-immobilised candidate substance determining whether and/or to what extent the CCDC95 polypeptide and candidate substance bind to each other. Alternatively, the candidate substance may be immobilised and the CCDC95 polypeptide non-immobilised.

In a preferred assay method, the CCDC95 polypeptide is immobilised on beads such as agarose beads. Typically this is achieved by expressing the component as a GST-fusion protein in bacteria, yeast or higher eukaryotic cell lines and purifying the GST-fusion protein from crude cell extracts using glutathione-agarose beads. As a control, binding of the candidate substance, which is not a GST-fusion protein, to the immobilised CCDC95 polypeptide is determined in the absence of the CCDC95 polypeptide. The binding of the candidate substance to the immobilised CCDC95 polypeptide is then determined. This type of assay is known in the art as a GST pulldown assay. Again, the candidate substance may be immobilised and the CCDC95 polypeptide non-immobilised.

Candidate substances are typically added to a final concentration of from 1 to 1000 nmol/ml, more preferably from 1 to 100 nmol/ml. In the case of antibodies, the final concentration used is typically from 100 to 500 µg/ml, more preferably from 200 to 300 µg/ml.

It is also possible to perform this type of assay using different affinity purification systems for immobilising one of the components, for example Ni-NTA agarose and hexahistidine-tagged components.

Binding of the CCDC95 polypeptide to the candidate substance may be determined by a variety of methods well-known in the art. For example, the non-immobilised component may be labelled (with for example, a radioactive label, an epitope tag or an enzyme-antibody conjugate). Alternatively, binding may be determined by immunological detection techniques. For example, the reaction mixture can be Western blotted and the blot probed with an antibody that detects the non-immobilised component. ELISA techniques may also be used.

Another type of in vitro assay involves determining whether a candidate substance modulates binding of a protein known to interact with CCDC95, such as a RGK Small binding protein. Such an assay typically comprises contacting CCDC95 protein with the known interacting protein in the presence or absence of the candidate substance and determining if the candidate substance has an affect on CCDC95 binding to the known interacting protein.

Whole Cell Assays

Candidate substances may also be tested on whole cells for their effect on cell morphology and differentiation. Preferably the candidate substances have been identified by the above-described in vitro methods. Alternatively, rapid throughput screens for substances capable of inhibiting or enhancing nuclear localisation of RGK Small binding protein, may be used as a preliminary screen and then used in the in vitro assay described above to confirm that the affect is on CCDC95.

The candidate substance, i.e. the test compound, may be administered to the cell in several ways. For example, it may be added directly to the cell culture medium or injected into the cell. Alternatively, in the case of polypeptide candidate substances, the cell may be transfected with a nucleic acid construct which directs expression of the polypeptide in the cell. Preferably, the expression of the polypeptide is under the control of a regulatable promoter.

Typically, an assay to determine the effect of a candidate substance identified by the method of the invention on RGK Small binding protein activity comprises administering the candidate substance to a cell and determining whether the substance affects RGK Small binding protein concentration or subcellular localisation.

The concentration of candidate substances used will typically be such that the final concentration in the cells is similar to that described above for the in vitro assays.

In a preferred embodiment, the candidate substance is administered to the cell together with functional CCDC95. Since CCDC95 has the effect of enhancing nuclear localization of RGK Small binding protein thereby inhibiting cell morphological changes, a substance that inhibits CCDC95 may serve to initiate cell morphological changes. Alternatively, if cell morphological changes are further reduced, then the substance may be an activator of CCDC95 function.

A candidate substance is typically considered to be an inhibitor of CCDC95 function if cell morphological activity is increased by at least 10%, preferably at least 20, 30 or 40% relative to the extent of cell morphological activity seen in the presence of CCDC95 and absence of the candidate substance. By contrast, a candidate substance is typically considered to be an activator of CCDC95 function if cell morphological activity is further decreased by at least 10%, preferably at least 20, 30 or 40% relative to the extent of cell morphological activity seen in the presence of CCDC95 and absence of the candidate substance.

Thus, this invention is also particularly useful for screening compounds by using the CCDC95 polypeptide or binding fragment thereof in any of a variety of drug screening techniques.

The CCDC95 polypeptide or fragment employed in such a test may either be free in solution, affixed to a solid support, or borne on a cell surface. One method of drag screening utilizes eucaryotic or procaryotic host cells which are stably transformed with recombinant polynucleotides expressing the polypeptide or fragment, preferably in competitive binding assays. Such cells, either in viable or fixed form, can be used for standard binding assays. One may measure, for example, for the formation of complexes between a CCDC95 polypeptide or fragment and the agent being tested, or examine the degree to which the formation of a complex between a CCDC95 polypeptide or fragment and a known ligand is interfered with by the agent being tested.

Thus, the present invention provides methods of screening for drugs comprising contacting such an agent with a CCDC95 polypeptide or fragment thereof and assaying (i) for the presence of a complex between the agent and the CCDC95 polypeptide or fragment, or (ii) for the presence of a complex between the CCDC95 polypeptide or fragment and a ligand, by methods well known in the art. In such competitive binding assays the CCDC95 polypeptide or fragment is typically labeled. Free CCDC95 polypeptide or fragment is separated from that present in a protein:protein complex, and the amount of free (i.e., uncomplexed) label is a measure of the binding of the agent being tested to CCDC95 or its interference with CCDC95:ligand binding, respectively.

Another technique for drug screening provides high throughput screening for compounds having suitable binding affinity to the CCDC95 polypeptides and is described in detail in Geysen, PCT published application WO 84/03564, published on Sep. 13, 1984. Briefly stated, large numbers of different small peptide test compounds are synthesised on a solid substrate, such as plastic pins or some other surface. The peptide test compounds are reacted with CCDC95 polypeptide and washed. Bound CCDC95 polypeptide is then detected by methods well known in the art.

Purified CCDC95 can be coated directly onto plates for use in the aforementioned drug screening techniques. However, antibodies to the polypeptide can be used to capture antibodies to immobilize the CCDC95 polypeptide on the solid phase.

This invention also contemplates the use of competitive drug screening assays in which antibodies capable of specifically binding the CCDC95 polypeptide compete with a test compound for binding to the CCDC95 polypeptide or fragments thereof. In this manner, the antibodies can be used to detect the presence of any peptide that shares one or more antigenic determinants of the CCDC95 polypeptide.

A further technique for drug screening involves the use of host eucaryotic cell lines or cells (such as described above) that have a nonfunctional CCDC95 gene. In one embodiment the polynucleotide's encoding coiled coil domains of the invention are deleted from the CCDC95 gene. These host cell lines or cells are defective in the CCDC95 at the polypeptide level. The host cell lines or cells are grown in the presence of drug compound. The cell morphological changes of the host cells is measured to determine if the compound is capable of regulating the cell morthological activity of CCDC95 defective cells.

The goal of rational drug design is to produce structural analogs of biologically active polypeptides of interest or of small molecules with which they interact (e.g., agonists, antagonists, inhibitors) in order to fashion drugs which are, for example, more active or stable forms of the polypeptide, or which, e.g., enhance or interfere with the function of a polypeptide in vivo. In one approach, one first determines the three-dimensional structure of a protein of interest (e.g., CCDC95 polypeptide) or, for example, of the ligand complex, by x-ray crystallography, by computer modeling or most typically, by a combination of approaches. Less often, useful information regarding the structure of a polypeptide may be gained by modeling based on the structure of homologous proteins. An example of rational drug design is the development of HIV protease inhibitors. In addition, peptides (e.g., CCDC95 polypeptide) are analysed by an alanine scan. In this technique, an amino acid residue is replaced by Ala, and its effect on the peptide's activity is determined. Each of the amino acid residues of the peptide is analysed in this manner to determine the important regions of the peptide.

It is also possible to isolate a target-specific antibody, selected by a functional assay, and then to solve its crystal structure. In principle, this approach yields a pharmacophore upon which subsequent drug design can be based. It is possible to bypass protein crystallography altogether by generating anti-idiotypic antibodies (anti-ids) to a functional, pharmacologically active antibody. As a mirror image of a mirror image, the binding site of the anti-ids would be expected to be an analog of the original receptor. The anti-id could then be used to identify and isolate peptides from banks of chemically or biologically produced peptides or other molecules. Selected peptides would then act as the pharmacophore.

Thus, one may design drugs that have, e.g., improved CCDC95 polypeptide activity or stability or which act as inhibitors, agonists, antagonists, etc. of RGK small binding proteins polypeptide activity. By virtue of the availability of cloned CCDC95 sequences, sufficient amounts of the CCDC95 polypeptide may be made available to perform such analytical studies as x-ray crystallography. In addition, the knowledge of the CCDC95 protein sequence provided herein will guide those employing computer modeling techniques in place of, or in addition to x-ray crystallography.

Therapeutic Uses

One aspect of the invention provides a method of modulating a RGK small binding proteins comprising the step of varying the concentration or subcellular location of RGK small binding proteins with CCDC95 polypeptides or peptide fragments as described above.

One approach is to administer elevated levels of functional CCDC95 proteins or nucleic acids by direct expression of the functional protein to target cells, a procedure termed gene therapy. The expression product increases nuclear localisation of RGK small binding proteins thereby initiating myoblast differentiation.

Thus the present invention provides a method of initiating myoblast differentiation which method comprises administering to said cell a functional CCDC95 polypeptide or polynucleotide encoding said polypeptide. The present invention further provides the use of a polypeptide or polynucleotide of the invention, which polypeptide or polynucleotide is, or encode, biologically active CCDC95 in gene therapy. Also provided is a method of treating a disease characterized by a heart disease resulting from deficiency in cardiomyocyte number, which method comprises administering to said cells a functional CCDC95 polypeptide or polynucleotide encoding said polypeptide to initiate myoblast differentiation. A wide variety of disorders or injuries can be treated with the myogenic protein isolate, alone or in combination with inducers of proliferation, such as one of the insulin growth factors, or other compounds, such as antibiotics or antiinflammatories. A preferred treatment is the treatment of wounds where the object is to enhance healing while minimizing scarring. Other diseases include muscular dystrophy, myasthenia gravis, multiple sclerosism, nerve block injuries, muscle atrophy, embryonic failure of myotomes to migrate, and rhabdomyosarcoma.

Examples of injuries or muscle weaknesses that can be treated include repair of aneurysms by increasing muscle bulk in the blood vessels, repair of hemorrhages by increasing muscle bulk around blood vessels, relief of ptosis (eye lid drep) by regeneration of non-damaged muscle in the eyelid, as well as tears in muscles and repair of muscle damaged by infarction, up to the point of growing new hearts or portions of heart muscle. The myogenic protein can also be used to form new tissues for transplantation, where a limited amount from the donor is available, particularly in the case of autologous transplants.

The myogenic protein can be administered directly to the stem cells to induce commitment prior to injection back into the patient, or implanted in a controlled release device at a selected site containing stem cells to induce commitment and differentiation. Once the gene is isolated for the myogenic protein, this can also be inserted directly into cells to induce commitment and differentiation.

Gene Therapy

According to the present invention, a method is also provided of supplying wild-type CCDC95 function to a cell that carries mutant CCDC95 alleles. Supplying such a function should initiate myoblast differentiation in deficient cells. CCDC95 function may be provided either through the use of gene therapy or alternatively it might be provided in the form of protein therapy which therapy is capable of delivering polypeptide over a sustained period of time.

The wild-type CCDC95 gene or a part of the gene may be introduced into the cell in a vector or as naked DNA such that the gene remains extrachromosomal. In such a situation, the gene will be expressed by the cell from the extrachromosomal location. If a gene fragment is introduced and expressed in a cell deficient in CCDC95 activity, the gene fragment should encode a part of the CCDC95 protein that is required for initiating myoblast differentiation. More preferred is the situation where the wild-type CCDC95 gene or a part thereof is introduced into a deficient cell in such a way that it compensates for the endogenous CCDC95 gene present in the cell. Vectors for introduction of genes both for recombination and for extrachromosomal maintenance are known in the art, and any suitable vector may be used. However, replication-incompetent retroviral vectors have proved safe and effective in recent trials and most of the approved human gene therapy trials to date rely on retroviral vectors. Thus it is preferred to use retroviral vectors, such as lentiviral vectors, comprising a polynucleotide of the invention and capable of expressing a polypeptide of the invention. Other viral vector systems include adenoviral vectors and herpes virus vectors.

Methods for introducing DNA into cells such as electroporation, calcium phosphate co-precipitation and viral transduction are known in the art, and the choice of method is within the competence of the person skilled in the art. A further gene transfer technique that has been approved by the FDA is the transfer of plasmid DNA in liposomes. Suitable liposome compositions include Lipofectin™.

Cells transformed with the wild-type CCDC95 gene can be used as model systems to study myoblast differentiation and drug treatments that promote such myoblast differentiation. Similarly mutants deficient in the CCDC95 gene or CCDC95 polypeptide function to screen molecules able to overcome the inhibition of myoblast differentiation.

As generally discussed above, the CCDC95 gene or fragment, where applicable, may be employed in gene therapy methods in order to increase the amount of the expression products of such genes in target cells. Such gene therapy is particularly appropriate for use in cells, in which the level of CCDC95 polypeptide is absent or diminished compared to normal cells. It may also be useful to increase the level of expression of a given CCDC95 gene even in those cells in which the CCDC95 gene is expressed at a "normal" level, but the gene product is not fully functional.

Gene therapy would be carried out according to generally accepted methods. Cells from a patient's would be first analysed by the diagnostic methods described above, to ascertain the production of CCDC95 polypeptide in the cells. A virus or plasmid vector (see further details below), containing a copy of the CCDC95 gene linked to expression control elements and capable of replicating inside the host cells, is prepared. Suitable vectors are known, such as disclosed in U.S. Pat. No. 5,252,479 and PCT published application WO 93/07282. The vector is then injected into the patient, either locally at the site of the disorder such as the heart. If the transfected gene is not permanently incorporated into the genome of each of the targeted cells, the treatment may have to be repeated periodically.

Gene transfer systems known in the art may be useful in the practice of the gene therapy methods of the present invention. These include viral and nonviral transfer methods. A number of viruses have been used as gene transfer vectors, including papovaviruses, e.g., SV40, adenovirus, vaccinia virus, adeno-associated virus, herpesviruses including HSV and EBV, and retroviruses of avian, murine, and human origin. Most human gene therapy protocols have been based on disabled murine retroviruses.

Nonviral gene transfer methods known in the art include chemical techniques such as calcium phosphate co-precipitation; mechanical techniques, for example microinjection; membrane fusion-mediated transfer via liposomes; and direct DNA uptake and receptor-mediated DNA transfer. Viral-mediated gene transfer can be combined with direct in vivo gene transfer using liposome delivery, allowing one to direct the viral vectors to the cells and not into the surrounding cells. Alternatively, the retroviral vector producer cell line can be injected into affected tissue.

In an approach which combines biological and physical gene transfer methods, plasmid DNA of any size is combined with a polylysine-conjugated antibody specific to the adenovirus hexon protein, and the resulting complex is bound to an adenovirus vector. The trimolecular complex is then used to infect cells. The adenovirus vector permits efficient binding, internalization, and degradation of the endosome before the coupled DNA is damaged.

Liposome/DNA complexes have been shown to be capable of mediating direct in vivo gene transfer. While in standard liposome preparations the gene transfer process is nonspecific, localized in vivo uptake and expression have been reported in tumour deposits, for example, following direct in situ administration.

Gene transfer techniques that target DNA directly to affected tissues are preferred. Receptor-mediated gene transfer, for example, is accomplished by the conjugation of DNA (usually in the form of covalently closed supercoiled plasmid) to a protein ligand via polylysine. Ligands are chosen on the basis of the presence of the corresponding ligand receptors on the cell surface of the target cell/tissue type. These ligand-DNA conjugates can be injected directly into the blood if desired and are directed to the target tissue where receptor binding and internalization of the DNA-protein complex occurs. To overcome the problem of intracellular destruction of DNA, coinfection with adenovirus can be included to disrupt endosome function.

Polypeptides that have CCDC95 activity can also be supplied to cells that are deficient in CCDC95 polypeptide or the polypeptide is inactive.

Active CCDC95 molecules can be introduced into cells by microinjection or by use of liposomes, for example. Alternatively, some active molecules may be taken up by cells, actively or by diffusion. Extracellular application of the CCDC95 gene product may be sufficient to affect calcium channel activity. Supply of molecules with CCDC95 activity should lead to partial reversal of the effects of an intercellular calcium imbalance. Other molecules with CCDC95 activity (for example, peptides, drugs or organic compounds) may also be used to effect such a reversal. Modified polypeptides having substantially similar function are also used for protein therapy.

Animals for testing therapeutic agents can be selected after mutagenesis of whole animals or after treatment of germline cells or zygotes. Such treatments include insertion of mutant CCDC95 alleles, usually from a second animal species, as well as insertion of disrupted homologous genes. Alternatively, the endogenous CCDC95 gene(s) of the animals may be disrupted by insertion or deletion mutation or other genetic alterations using conventional techniques. After test substances have been administered to the animals. If the test substance initiates myoblast differentiation, then the test substance is a candidate therapeutic agent for the treatment of the disorders related to cardiomyocyte deficiency identified herein. These animal models provide an extremely important testing vehicle for potential therapeutic products.

Therapeutic Compounds

A further aspect of the invention comprises a compound for modulating RGK small binding protein or protein mutants or peptide fragments thereof.

Examples of compounds for antagonistic activity of a voltage gated calcium channel may comprise CCDC95, peptide fragments: Coiled coil like domain of CCDC95 or variants thereof; fusion Sequences comprising Coiled coil like domain of CCDC95 or variants thereof. The compounds for antagonising activity of a RGK small binding protein may comprise a CCDC95 protein or variants thereof. Increasing CCDC95 activity or peptide interaction with RGK small binding protein moving the RGK small binding protein to the nucleus in any way including those mentioned above could be used to move treat Disorders related to voltage gated calcium channels including ataxia, migraine, epilepsy, neurodegeneration, hypertension and cardiac disorders including cardiomyocyte deficiency.

Examples of compounds for agonistic activity of a RGK small binding protein may comprise protein mutants of CCDC95 wherein the Coiled coil like domain are deleted from the CCDC95 protein, antibodies of CCDC95 as described above. The compounds for agonistic activity of a Coiled coil like domain may comprise a compound that reduces the level of expression of CCDC95 including both mRNA expression and protein expression; or the sub-cellular localisation of RGK small binding protein to the cytosol. Interfering with the binding of CCDC95 to RGK small binding protein or down regulating CCDC95 expression by small interfering RNA or in any alternative way including those mentioned above could be used to treat Disorders related to lack of RGK small binding protein. The silencing RNA for example may comprise SEQ ID NO. 7 AAGATGCCTCCA-CATACAATCCTGAGCAC or SEQ ID NO. 8 GATCGACT-TCTGCAGTATGAGAACGTGGA.

Compounds identified by the assay methods of the present invention as regulating CCDC95 function may also be used in therapeutic methods of the present invention. For example, a compound identified as binding to and enhancing CCDC95 function may be administered to cells exhibiting RGK small binding protein disorders.

Administration

Substances identified or identifiable by the assay methods of the invention may preferably be combined with various components to produce compositions of the invention. Preferably the compositions are combined with a pharmaceutically acceptable carrier or diluent to produce a pharmaceutical composition (which may be for human or animal use). Suitable carriers and diluents include isotonic saline solutions, for example phosphate-buffered saline. The composition of the invention may be administered by direct injection. The composition may be formulated for parenteral, intramuscular, intravenous, subcutaneous, intraocular, oral or transdermal administration. Typically, each substance may be administered at a dose of from 0.01 to 30 mg/kg body weight, preferably from 0.1 to 10 mg/kg, more preferably from 0.1 to 1 mg/kg body weight.

Polynucleotides/vectors encoding polypeptide components (or antisense constructs) for use in therapeutic methods may be administered directly as a naked nucleic acid construct. They may further comprise flanking sequences homologous to the host cell genome. When the polynucleotides/vectors are administered as a naked nucleic acid, the amount of nucleic acid administered may typically be in the range of from 1 µg to 10 mg, preferably from 100 µg to 1 mg. It is particularly preferred to use polynucleotides/vectors that target specific cells, for example by virtue of suitable regulatory constructs or by the use of targeted viral vectors.

Uptake of naked nucleic acid constructs by mammalian cells is enhanced by several known transfection techniques for example those including the use of transfection agents. Example of these agents include cationic agents (for example calcium phosphate and DEAE-dextran) and lipofectants (for example Lipofectam™ and Transfectam™). Typically, nucleic acid constructs are mixed with the transfection agent to produce a composition.

Preferably the polynucleotide or vector according to the invention is combined with a pharmaceutically acceptable carrier or diluent to produce a pharmaceutical composition. Suitable carriers and diluents include isotonic saline solutions, for example phosphate-buffered saline. The composition may be formulated for parenteral, intramuscular, intravenous, subcutaneous, intraocular, oral or transdermal administration.

Another aspect of the invention provides the use of any of the compositions of for modulation of RGK small binding protein in treating disorders related to RGK small binding protein. Disorders related to RGK small binding protein include ataxia, migraine, epilepsy, neurodegeneration, hypertension, cardiac disorders and diabetes.

The amino acid compositions of the invention may be delivered as peptides directly to the tissue where they are required; prepared in a biological scaffold; in a polymer delivery system or as nucleic acids in recombinant vectors capable of expressing the amino acid composition.

Generally, in humans, oral or topical administration of the compositions is the preferred route, being the most convenient. In circumstances where the recipient suffers from a swallowing disorder or from impairment of drug absorption after oral administration, the drug may be administered parenterally, e.g. sublingually or buccally. This is a particularly useful method of delivery for large peptide drugs. Peptides can be more easily absorbed and delivered to the location of action when they are delivered sublingually or buccally. The efficiency can be increased where the peptides are placed in a scaffold that can help maintain the peptide structure and hence activity. The compositions of the invention will normally be administered intravenously, or by any parenteral route, in the form of a pharmaceutical composition comprising the active ingredient, optionally in the form of a non-toxic organic, or inorganic, acid, or base, addition salt, in a pharmaceutically acceptable dosage form. Depending upon the RGK small binding protein dependant disorder and patient to be treated, as well as the route of administration, the compositions may be administered at varying doses.

In human therapy, the compositions can be administered alone but will generally be administered in admixture with a suitable pharmaceutical excipient diluent or carrier selected with regard to the intended route of administration and standard pharmaceutical practice.

The compositions of the invention can also be administered parenterally, for example, intravenously, intra-arterially, intraperitoneally, intrathecally, intraventricularly, intrasternally, intracranially, intra-muscularly or subcutaneously, or they may be administered by infusion techniques. They are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral compositions under sterile conditions is readily accomplished by standard pharmaceutical techniques well-known to those skilled in the art.

Compositions suitable for parenteral administration include aqueous and nonaqueous sterile injection solutions which may contain anti-oxidants, buffers, bacteriostats and solutes which render the composition isotonic with the blood of the intended recipient; and aqueous and non-aqueous sterile suspensions which may include suspending agents and thickening agents. The compositions may be presented in unit-dose or multi-dose containers, for example sealed ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets.

The compositions may also be transdermally administered, for example, by the use of a skin patch. In one embodiment preferably the composition may be administered transdermally. Transdermal administration may be via membranes, patches or sheets placed on the patient's skin. The membranes may be designed for slow release application of the composition, which may include admixtures. The membranes may also be designed to have the advantage of a substantially water free composition. The preparation of suitable membrane compositions under sterile conditions is readily accomplished by standard transdermal techniques well-known to those skilled in the art.

In one embodiment the composition comprises a formula suitable for aerosol delivery to a patient. The compositions of the invention can also be administered intranasally or by inhalation and are conveniently delivered in the form of a dry powder inhaler or an aerosol spray presentation from a pressurised container, pump, spray or nebuliser with the use of a suitable propellant, e.g. dichlorodifluoromethane, trichlorofluoromethane, dichlorotetrafluoro-ethane, a hydrofluoroalkane such as 1,1,1,2-tetrafluoroethane (HFA 134A3 or 1,1,1,2,3,3,3-heptafluoropropane (HFA 227EA3), carbon dioxide or other suitable gas. in the case of a pressurised aerosol, the dosage unit may be determined by providing a valve to deliver a metered amount. The pressurised container, pump, spray or nebuliser may contain a solution or suspension of the active composition, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of a composition of the invention and a suitable powder base such as lactose or starch.

Aerosol or dry powder compositions are preferably arranged so that each metered dose or "puff" contains at least 1 mg of a composition of the invention for delivery to the patient. It will be appreciated that the overall daily dose with an aerosol will vary from patient to patient, and may be administered in a single dose or, more usually, in divided doses throughout the day.

For example, the compositions of the invention can be administered orally, buccally or sublingually in the form of tablets, capsules, ovules, elixirs, solutions or suspensions, which may contain flavouring or colouring agents, for immediate-, delayed- or controlled-release applications. The preparation of suitable oral compositions under sterile conditions is readily accomplished by standard pharmaceutical techniques well-known to those skilled in the art. The compositions of invention may also be administered via intracavernosal injection. Alternatively, the compositions of the invention can be administered in the form of a suppository or pessary. Compositions may also be administered by the ocular route, For ophthalmic use, the compositions of the invention can be formulated as micronised suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

The invention may further comprise a method for identifying a composition expected to be useful for treating a disorders related to RGK small binding protein, the method comprising the steps of: treating a cell overproducing CCDC95 with a test composition; and assessing the effect of the test composition on the activity, concentration and/or subcellular location of RGK small binding protein.

The method of the invention may further comprise the steps of providing, synthesising, purifying and/or formulating a composition selected using computer modelling, as known by those in the art; and of assessing whether the composition modulates the activity of RGK small binding protein. The composition may be formulated for pharmaceutical use, for example for use in in vivo trials in animals or humans.

The routes of administration and dosages described are intended only as a guide since a skilled practitioner will be able to determine readily the optimum route of administration and dosage for any particular patient and condition.

Modulation of Myogenic Cell Differentiation

Stem cells and cell fate determination can be manipulated with the CCDC95 protein. Since CCDC95 is mostly in smooth and heart muscle, but Kir/Gem blocks skeletal muscle differentiation in vitro. Thus, the two proteins coordinate to favor differentiation into heart rather than skeletal muscle and may be used to regulate differentiation in vitro. Where it is preferable to obtain heart muscle this is achieved by varying the amounts of CCDC95 and RGK small binding protein protein in favour of head cell differentiation. Where it is preferable to obtain skeletal muscle this is achieved by varying the amounts of CCDC95 and RGK small binding protein in favour of skeletal cell differentiation.

Further features of the present invention are more fully described in the following non-limiting Examples. It is to be understood, however, that this detailed description is included solely for the purposes of exemplifying the present invention. It should not be understood in any way as a restriction on the broad description of the invention as set out above.

Methods of molecular cloning, immunology and protein chemistry which are not explicitly described in the following examples are reported in the literature and are known by those skilled in the art. General texts that described conventional molecular biology, microbiology, and recombinant DNA techniques within the skill of the art, included, for example: Sambrook et al., *Molecular Cloning: A Laboratory Manual*, Second Edition, Cold Spring Harbor Laboratory Press, Cold Spring Harbor, N.Y. (1989); Glover ed., *DNA Cloning: A Practical Approach*, Volumes I and II, MRL Press, Ltd., Oxford, U.K. (1985); and Ausubel, F., Brent, R., Kingston, R. E., Moore, D. D., Seidman, J. G., Smith, J. A., Struhl, K. *Current protocols in molecular biology*. Greene Publishing Associates/Wiley Intersciences, New York.

CCDC95 is a novel muscle specific protein that associates with Kir/Gem and under certain circumstances participates in nuclear transport of the GTP-binding protein. The interaction with CCDC95 involves positively charged amino acids in the C-terminal extension of Kir/Gem.

Isolation of Novel Proteins Interfering with RGK Proteins

To identify new regulators or effectors of Kir/Gem, a yeast two-hybrid (Y2H) screen was performed using a MIN6 library (Béguin et al., 2001 *Nature*. 411:701-6). This led to the identification of several positive clones, including CCDC95. CCDC95 (coiled-coiled domain containing 95) is a novel protein that contains as only protein motif a coiled-coiled domain, which is highly conserved from flies to mammals (FIG. 1A).

The yeast two-hybrid screen of a cDNA library from mouse MIN6 cell using the full length of Kir/Gem as bait was performed as described (Béguin et al., 2001 *Nature*. 411:701-6). Sequence analysis of EST clones from mouse, rat and human allowed us to identify the initiation Met for CCDC95, which conforms to a Kozak consensus sequence (Kozak, 1987 *Nucleic Acids Res.* 15:8125-48). CCDC95, RGK proteins, 14-3-3 and β-galactosidase were epitope tagged at their N-terminus as previously outlined (Béguin et al., 2005 *J. Cell Sci.* 118:1923-34). Fusion proteins between GST and different importins or CCDC95 were generated as described (Mahalakshmi et al., 2007 *Traffic*. 8:1150-63).

CCDC95 Protein Localisation

Northern blot analysis was performed under standard stringency hybridization and washing condition using the human CCDC95 cDNA as a probe. Northern blot analysis revealed that CCDC95 is widely expressed in all tissues analyzed (FIG. 2A). However, staining of a tissue array with two affinity-purified antibodies raised against different epitopes suggested that CCDC95 expression is mostly in smooth muscle and heart (FIGS. 1 C and D, and FIG. 8 *a*), expression was also observed in embryoskeletal muscle. The ubiquitous expression of CCDC95 mRNA therefore likely reflects the widespread presence of muscle cells in most tissues, for example as part of the vasculature.

Endogenous CCDC95 was detected either using a custom made affinity-purified rabbit anti-peptide LQYENVDEDSSDSDA antibody or a mouse monoclonal antibody against a GST fusion protein containing amino acids D64-G182). Endogenous Kir/Gem was revealed using a rabbit antibody (Mahalakshmi et al., 2007 Traffic. 8:1164-78).

Cells were fixed with 3.7% paraformaldehyde, washed twice with PBS, quenched with 50 mM NH4Cl and permeabilized with 0.2% Triton X-100. Cells were then incubated in blocking solution (PBS containing 0.1% Triton X-100, 0.1% bovine serum albumin (BSA) and 250 mM NaCl) for 30 min, followed by incubation with various primary antibodies (see above) in blocking solution for 1 h. After washing, Cy3-labeled donkey anti-rabbit IgG (Jackson Immuno Research Laboratories) and Alexafluor 488-labeled goat anti mouse IgG (Molecular Probes) were used as secondary antibodies. Actin filaments and nuclei were detected by incubating fixed cells for 15 min the fixed cells with Oregon green fluorescent-labeled phalloidin and Hoecht 33342 (Molecular Probes), respectively. Mouse brain cryosections were processed either for either immunolabeling using the Vectastain ABC kit (Vector Laboratories) or the standard immunofluorescence procedure (see above). Specimens were visualized with an Axiocam microscope (Carl Zeiss) or with a LSM 510 Meta confocal microscope (Carl Zeiss) at 40× and 63× magnifications.

In heart, CCDC95 was present in distinct stripes that partially colocalized with troponin T (FIG. 1D), a protein present in the Z-bands and involved in the regulation of muscle contraction (Gomes et al., 2004). The colocalization of CCDC95 with troponin T was confirmed in primary cardiomyocytes (FIG. 1D). These results identify CCDC95 as a novel interacting partner for Kir/Gem, with expression predominantly in muscle and different subcellular localizations.

CCDC95 expression is observed in smooth muscle, embryo skeletal muscle and heart and its expression temporally correlated with muscle differentiation and the expression of other muscle specific genes. In early stages of cardiomyocyte differentiation, CCDC95 is induced in a similar time frame as the αMHC and MLC2v, two major contractile proteins (Parisi et al., 2003). CCDC95 expression is also induced in fibroblasts following overexpression of myoD, a transcription factor known to activate other muscle specific genes in this system (Qin et al., 2007). MyoD and other MRF family members bind to E-box elements in the promoter regions of regulated genes and several E-boxes are present upstream of the coding region in the CCDC95 gene. It is thus conceivable that CCDC95 expression is directly regulated by MyoD. Interestingly, depending on the physiological or cellular context, CCDC95 is not only found in the nucleus, but also present in other subcellular locations. These include a colocalization with troponin T in striations of muscle fibers and actin filaments (data not shown). Thus, CCDC95 may be a novel regulatory component of the contractile system of muscle and/or the actin cytoskeleton.

The muscle specific expression of CDCC95 and its regulation during myogenesis led to the discovery of a novel function for Kir/Gem in muscle development. Although CCDC95 interacts with other RGK protein family members and Rad is expressed in heart and upregulated during muscle development (Hawke et al., 2006), only overexpression of Kir/Gem blocked muscle differentiation. The absence of the myogenic markers myogenin and troponin T in mono- and polynucleated cells overexpressing Kir/Gem suggest that the RGK protein inhibits early steps of myoblast differentiation. However, additional effects at later steps, for example on myoblast fusion, cannot be ruled out. Interestingly, endogenous Kir/Gem redistributes from a predominant nuclear to a cytoplasmic localization in myoblasts during early stages of differentiation and, concomitant with the appearance of CCDC95, relocalizes to apopotic nuclei of myotubes following fusion. The critical role for the temporally regulated subcellular distribution of Kir/Gem in the process is underscored by the observation that overexpression of either Kir/Gem W269G mutant or CCDC95 partially released the inhibitory effect of Kir/Gem on differentiation. Since Kir/Gem W269G predominantly localizes to the nucleus and CCDC95 favors the nuclear localization of WT Kir/Gem, the presence of the small GTP binding protein in the cytoplasm is likely required for its inhibitory effect.

Overexpression of the Protein

Surprisingly, overexpression of CCDC95 in either COS-1 or cardiomyocyte-derived H9c2(2-1) cells showed a predominant nuclear localization of the protein (FIG. 1E). Immunochemisty was conducted as previously described here. COS-1, Hela, PC-12, H9c2 (2-1) cells as well as undifferentiated ES cells were grown as previously described (Béguin et al., 2005a; Mahalakshmi et al., 2007a; Xu et al., 1999). Swiss 3T3 cells (purchased from ATCC) were maintained in DMEM high glucose with 10% fetal calf serum (FCS) medium. Primary cardiomyocytes were obtained from Cambrex and cultured according to the manufacturer's protocol. Transient transfections were carried out using Lipofectamine Plus or Lipofectamine 2000 and Opti-MEM I reagents (Invitrogen) according to the manufacturer's instructions. 100 mm dishes and 12 mm coverslips were used for biochemical and immunofluorescence studies, respectively. Experiments were performed 24-48 hours after transfection. Rat cardiomyocyte H9c2 cells were differentiated into myotubes by shifting the cells (at 80% confluence) from the standard 10% fetal bovine serum (FBS) medium to low serum condition (1% FBS) for 5-7 days. A similar procedure was carried out for the Swiss 3T3 cells, which were maintained in 1% FCS for 1 day. ES cells were cultured in the original medium without LIF (leukemia inhibitory factor) for several days.

Cells overexpressing CCDC95 and/or RGK proteins were lysed in a buffer containing 50 mM Tris-HCl (pH 7.5), 100 mM NaCl, 1 mM MgCl2, 0.5% Triton X-100 supplemented with 5 μg/ml of each of the protease inhibitors leupeptin, pepsatin, antipain and chymostatin (Calbiochem). For endogenous CCDC95 detection, a RIPA buffer was used. The subsequent steps of lysate preparation were then carried out as described (Béguin et al., 2005b).

Sequence Characterisation

To map the structural determinants responsible for the interaction between Kir/Gem and CCDC95, coimmunoprecipitation and Y2H assays were carried out. As shown in FIG. 2A, wild-type (WT) Kir/Gem or a mutant that does not bind CaM (Kir/Gem W269G) (Becker et al., 1995; Fischer et al., 1996) both co-immunoprecipitated with CCDC95 (FIG. 2A panel a, lane 1 and 4), confirming the specificity of the interaction. Truncations showed that the N-terminal part of CCDC95 containing the coiled-coil domain was sufficient for the interaction (FIG. 2A panel a, lane 2). Interestingly, although the C-terminus of CCDC95 did not bind to Kir/Gem (FIG. 2A panel a, lane 3), in its absence the slower migrating phosphorylated form of Kir/Gem (Beguin et al., 2007) was lost (FIG. 2A panel b, lane 2). This indicates that the C-terminus of CCDC95 affects the stability of Kir/Gem.

Cell lysates (400 μg total protein) were incubated with 4 μl FLAG-agarose beads (M2; Sigma) and 30 μl of protein G sepharose beads (Amersham) for 4 hours at 4° C. in lysis buffer. The beads were then washed extensively and eluted protein complexes were subjected to SDS-PAGE (8%) and Western blot analysis. In vitro pull down assays using purified GST-importins (2 μg) and cell lysate (400 μg total protein) containing WT or mutated Kir/Gem were carried out as detailed (Mahalakshmi et al., 2007a).

To identify the amino acids in the coiled-coil domain of CCDC95 important for the association with Kir/Gem, clusters of three residues were mutated to Ala and interaction of the mutants with Kir/Gem tested using the Y2H assay (data not shown). Individual amino acids in the susceptible region where then substituted with Ala residues, leading to the identification of 15 residues whose mutation interfered with Kir/Gem binding (FIG. 2B). These 15 critical amino acids cluster to helices I and III of the coiled-coil domain. The importance of the individual residues in CCDC95 for the interaction with Kir/Gem was confirmed in coimmunoprecipitation experiments (FIG. 2C).

For western blot analysis, mouse monoclonal anti-FLAG (M2; Sigma), mouse monoclonal anti-Myc, rabbit anti-GST (Santa Cruz) and mouse polyclonal anti-importin α5 (Abnova) antibodies were used. The same anti-FLAG and anti-Myc antibodies, as well as antibodies to MyoD1 (Abcam), troponin T (Sigma), myogenin (Abcam) and α-tubulin (Serotec) were used for immunofluorescence microscopy.

Next, we analyzed the structural features in Kir/Gem important for CCDC95 binding (FIGS. 2D and E). Several mutants of Kir/Gem known to be defective in both GTP and GDP binding (Béguin et al., 2005b) failed to coprecipitate with CCDC95 (FIG. 2E, panel a, lanes 2-5), indicating that this association requires an intact Kir/Gem conformation. N- and C-terminal truncations implicated the C-terminus of Kir/Gem, in particular the region between amino acids 235 and 282, in CCDC95 binding (FIG. 2E, panel a, lanes 6-9). Analysis of point mutations identified a cluster of Asn and Lys residues (K275, N276, N277, K278 and N279) to be critical for the association (FIG. 2E, panel a, lanes 10-16), with the interaction between Kir/Gem N277A/K278A/N279N and CCDC95 being almost abolished (lane 11).

Given the role of positively charged residues in the interaction with CCDC95 and their proximity to a previously identified bipartite nuclear localization signal (NLS3) rich in Lys and Arg residues (Mahalakshmi et al., 2007a), we extended our analysis to the NLS. Intriguingly, inactivation of NLS3 in Kir/Gem (NLS3 mutated) completely abolished its interaction with CCDC95 (FIG. 2E, panel a, lane 18). Although mutation of NLS1-2 in Kir/Gem also abolished its interaction with CCDC95 (FIG. 2E, panel a, lane 17), this most likely reflects and altered conformation since this mutant includes the Y156A substitution known to affect GTP/GDP binding (lane 4).

In summary, these experiments establish a specific interaction between Kir/Gem and the coiled-coil domain of CCDC95. Positively charged amino acids in the C-terminus of Kir/Gem as well as its conformational integrity are critical for the interaction.

Bound CaM and/or 14-3-3, which retain Kir/Gem in the cytoplasm may be displaced by CCDC95 to allow nuclear transport. Interestingly, many of the positively charged amino acids required for CCDC95 binding are located within or in the vicinity of the NLS that associates with importin α5, suggesting a mutually exclusive association. Furthermore, CCDC95 binding is sensitive to conformational changes in Kir/Gem since mutants that bind neither GTP nor GDP fail to interact, providing additional mechanisms to regulate the association.

The interaction of CCDC95 with Kir/Gem is linked to two distinct effects on the small GTP binding protein. First, CDCC95 enhanced the efficiency of nuclear localization of Kir/Gem. CCDC95 itself carries several NLSs and utilizes importins α6 and α7 for nuclear import. CCDC95 and importin α5 binds to a common Cterminal region in Kir/Gem (Mahalakshmi et al., 2007a) and CCDC95 can circumvent the requirement of importin α5 for nuclear transport of the RGK protein. These findings support a role for CCDC95 in nuclear import from the cytosol as opposed to nuclear retention of Kir/Gem. A second function of CCDC95 is to stabilize Kir/Gem, a function that has also been observed for 14-3-3 proteins (Ward et al., 2004). Since in contrast to other small GTPases RGK proteins are transcriptionally induced and subject to rapid turnover, CCDC95 may regulate the cellular levels of Kir/Gem and/or sequester the protein to a particular cellular location in an inactive state from where it can be readily released to exert its function.

Interaction of CCDC95 with Other RGK Small GTP Binding Protein Family

Kir/Gem is a member of the RGK small GTP binding protein family, which also comprises the closely related Rad, Rem and Rem2. To investigate if these other members of the RGK protein family interact with CCDC95, we carried out co-immunoprecipitation experiments (FIG. 3A). As compared to the interaction of Kir/Gem, Rad and Rem showed a consistently less efficient association with CCDC95 (FIG. 3A, panel a, lanes 1-3) and no co-precipitation with Rem2 could be detected (FIG. 3A, panel a, lane 4). Thus, it is possible that CCDC95 also regulates Rad and Rem (see below), but given the robust interaction with Kir/Gem, the subsequent characterization of the functional role of CCDC95 on RGK protein function focused on Kir/Gem.

CCDC95 Mediates Nuclear Localization of Kir/Gem and Abrogates the Kir/Gem Mediated Inhibition of the Rho Pathway To obtain further insight into the role of CCDC95, we analyzed by immunofluorescence microscopy its effect on the subcellular distribution of the RGK proteins and the changes in cell shape induced by these GTP binding proteins. Immunochemisty was conducted as previously described here. As reported previously (Béguin et al., 2006; Béguin et al., 2005a; Béguin et al., 2005b; Mahalakshmi et al., 2007a; Mahalakshmi et al., 2007b; Piddini et al., 2001), overexpression of RGK proteins in COS-1 cells induced dendrite-like extensions and cell flattening (FIG. 3B, panels, a, d, f, h). In cells co-expressing CCDC95, the RGK mediated changes in cell shape were mitigated and this correlated with an enhanced nuclear translocation of the RGK protein. The extent of nuclear accumulation of the small GTP binding protein closely correlated with their efficiency to co-precipitate with CCDC95, being most pronounced for Kir/Gem (FIG. 3B, panels b-b", FIG. 9b, panels c-c") and either reduced for Rad and Rem (FIG. 3B panels e-e" and g-g") or not apparent for Rem2 (FIG. 3B panels i-i"). In contrast to the wild-type protein, overexpression of CCDC95 Y15A/Y60A, a mutant defective in Kir/Gem binding to the RGK protein (see FIG. 2), neither altered the subcellular distribution of Kir/Gem nor abolished its induction of dendrite-like extensions (FIG. 3B, panels c-c").

Quantification of the effects of CCDC95 on the subcellular distribution of the RGK proteins and their induced changes in cell shape is shown in FIG. 9a and FIG. 3C respectively. For quantification of morphological changes, a similar analysis was performed and cells grouped into three categories (no, short and long extensions). Short extensions were defined as those with one length or less of the cell body diameter, whereas long extensions represented those longer that one length of the cell body diameter.

The effects of Kir/Gem on cell morphology have been attributed to reorganization of both the actin and microtubule cytoskeletons (Kelly, 2005). Kir/Gem negatively regulates the Rho pathway by directly interacting with the ROKβ kinase (Ward et al., 2002) and Gmip (Hatzoglou et al., 2007), a Rho GAP. We therefore determined if CCDC95 compensates the negative regulation of the Rho pathway by Kir/Gem. For this purpose, Kir/Gem and/or CCDC95 were expressed in Swiss 3T3 cells and the effect on the formation of stress fibers following serum starvation was monitored as a read-out for Rho activity.

Serum-starved Swiss 3T3 cells reorganized their actin cytoskeleton to promote long stress fibers spanning the whole cell (FIG. 3D, panel a). Overexpression of Kir/Gem provoked a collapse of the stress fibers, with actin now accumulating diffusely in the cell center (FIG. 3D, panels a-a"). In contrast, co-expression of Kir/Gem with CCDC95 resulted in the nuclear accumulation of Kir/Gem and the preservation of the stress fibers (FIG. 3D, panel b-b"). As a control, CCDC95 Y15A/Y60A, a mutant that fails to bind Kir/Gem, did not prevent the Kir/Gem induced collapse of the stress fibers (FIG. 3D, panel c-c"). Quantifications of this data is shown in FIG. 9c.

In conclusion, CCDC95 promotes nuclear localization of Kir/Gem and thereby abrogates the inhibitory effect of the small GTP binding protein on the Rho/Rho kinase pathway.

CCDC95 Stabilizes Kir/Gem by Preventing Proteasomal Degradation

The expression of Kir/Gem is tightly regulated both at the transcriptional (Cohen et al., 1994; Maguire et al., 1994; Warton et al., 2004) and translational levels, with a relatively short half-life of the protein of ~2 hours (Ward et al., 2004). To explore if CCDC95 binding affects the turnover of Kir/Gem, COS-1 cells co-expressing WT or mutated Kir/Gem and CCDC95 were subjected to cyclohexamide treatment to inhibit protein synthesis.

Cell lysates (400 µg total protein) were incubated with 4 µl FLAG-agarose beads (M2; Sigma) and 30 µl of protein G sepharose beads (Amersham) for 4 hours at 4° C. in lysis buffer. The beads were then washed extensively and eluted protein complexes were subjected to SDS-PAGE (8%) and Western blot analysis. In vitro pull down assays using purified GST-importins (2 µg) and cell lysate (400 µg total protein) containing WT or mutated Kir/Gem were carried out as detailed (Mahalakshmi et al., 2007a). The half-life of WT or mutated Kir/Gem was analyzed by blocking protein synthesis using cyclohexamide. COS-1 cells were incubated with 10 µg/ml cyclohexamide (Sigma) and cell lysates prepared at different time points. In some cases, cells were preincubated for one hour with 5 µM of the proteasome inhibitor MG132 (Sigma) prior to the addition of cycloheximide.

As shown in FIG. 4A, Kir/Gem was rapidly degraded with a half-life of ~1.5 hours (panel a). Turnover of Kir/Gem was slower in the presence of the proteasome inhibitor MG132 (FIG. 4A, lane 6), suggesting an involvement of the proteasomal degradation system. Albeit somewhat slower (t1/2: ~3 hrs), turnover of Kir/Gem W269G, which has predominant nuclear localization in COS-1 cells, was similarly affected (FIG. 4A, panel b). This indicates that the small GTP-binding protein was subject to degradation irrespective of its subcellular localization. Interestingly, co-expression of CCDC95, but not the Y15A/Y60A mutant that does not bind the RGK protein, resulted in a stabilization of Kir/Gem (FIG. 4A, panel c and e).

CCDC95 itself remained stable over the time course of the experiment (FIG. 4A, panel d and f). As reported previously (ref), Kir/Gem was also stabilized by overexpressing 14-3-3 proteins, but in contrast to CCDC95, 14-3-3 only protected the phosphorylated form of Kir/Gem from degradation (FIG. 4A, panel g). Coimmunoprecipitation experiments confirmed the association between Kir/Gem and CCDC95 at the different time points of the experiment (FIG. 4B, panel a), consistent with the notion that protection of Kir/Gem is linked to its association with CCDC95.

In summary, these experiments establish a role for CCDC95 in regulating the turnover of Kir/Gem by preventing its proteasomal degradation.

Nuclear localization signals mediate the interaction of CCDC95 with importins α6 and α7

Figure 1:
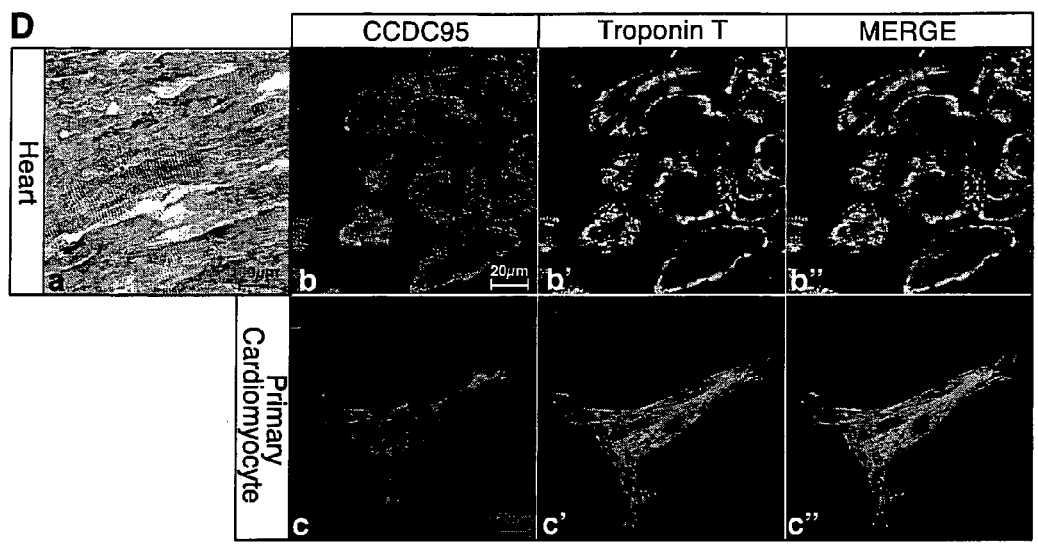
FIG. 1. Characterization of the new protein CCDC95
Figure 1:
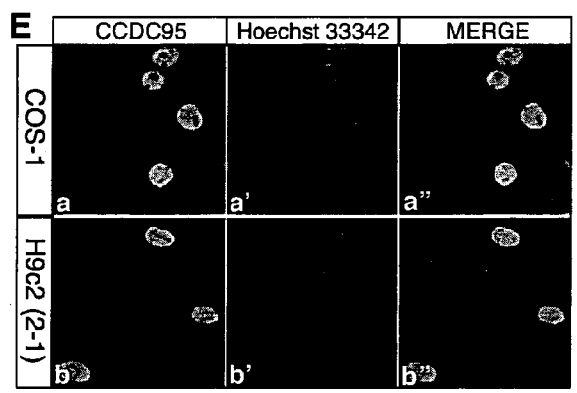

Whereas endogenous CCDC95 was found in the cytoplasm or nucleus depending on cell type and experimental condition (see below), the overexpressed protein efficiently localized to the nucleus (FIG. 1). To determine if nuclear localization may be of physiological relevance, we first analyzed if CCDC95 encodes nuclear localization signals (NLS). Classical NLSs are characterized by clusters of basic amino acids and can be classified into mono- or bipartite motifs (Dingwall and Laskey, 1991). CCDC95 contains four clusters, two in the N-terminal coiled-coil domain and two in the C-terminus, of positively charged residues reminiscent of canonical NLSs (NLS1-4) (FIG. 5A). By immunofluorescence microscopy, N- and C terminal truncated mutants of CCDC95 efficiently accumulated in the nucleus of COS-1 cells (FIG. 5A, panel 1 and 5). Immunochemisty was conducted as previously described here. Substitution of the positively charged residues in NLS2 with alanines abolished nuclear translocation of the coiled-coil domain (FIG. 5A, panel 3 and 4), whereas mutation of NLS1 showed an intermediate effect with an increased diffused localization (FIG. 5A, panel 2). Individual mutation of NLS3 or NLS4 partially affected the efficient nuclear localization of the C-terminal portion of CCDC95 (FIG. 5A, panel 6 and 7) and only the simultaneous mutation of both NLSs interfered with nuclear accumulation (FIG. 5A, panel 8). Analysis of the relevance of the four NLSs in the context of full-length CCDC95 revealed that the presence of two functional NLS was sufficient for nuclear localization (FIG. 5A, panel 9 and 10), whereas mutation of all four NLSs was required to prevent nuclear localization of the protein (FIG. 5A, panel 11). CCDC95 truncations and point mutations were generated by polymerase chain reaction (PCR) method.

Mutational analysis of other putative NLSs present in CCDC95 showed that they do not contribute to its subcellular distribution (data not shown). Classical NLSs facilitate nuclear transport by interacting with importins (Xu and Massague, 2004). To determine if CCDC95 associates with specific importins, pull down experiments were carried out by incubating different GST-importin fusion proteins lysates of COS-1 cells expressing either WT CCDC95 or a mutant lacking all four NLSs. CCDC95 showed a specific interaction with importins α6 and α7 (FIG. 5B, panel a, lane 6 and 7) and mutation of the NLSs abolished this association (FIG. 5B, panel a, lane 8 and 9).

These data thus identify NLSs in CCDC95 and show that nuclear localization is dependent on importins α6 and α7.

CCDC95 plays a role in nuclear transport as opposed to nuclear retention of Kir/Gem The nuclear redistribution of Kir/Gem induced by coexpression with CCDC95 (see above, FIG. 3) could reflect an enhanced rate of transport from the cytoplasm to the nucleus or, alternatively, nuclear retention and inhibition of nuclear export of the small GTP binding protein by CCDC95. To distinguish between these two mechanisms, we took advantage of the observation that nuclear localization of Kir/Gem in the absence of bound CaM (i.e. of Kir/Gem W269G) requires importin α5 (Mahalakshmi et al., 2007a), which is dispensable for nuclear transport of CCDC95 (see above). Thus, an enhanced nuclear localization of Kir/Gem when co-expressed with CCDC95 in cells depleted of importin α5 would argue for a role of CCDC95 in facilitating nuclear transport of Kir/Gem.

As previously reported (Mahalakshmi et al., 2007a), RNAi-mediated depletion of importin α5 in Hela cells prevented nuclear accumulation of Kir/Gem W269G (FIG. 5C, panel a and b and FIG. 10). Hela cells we transfected with a mix of 100 nM importin α5 Stealth siRNA (AATGT-GCTTTCCTGGTTGCTGTT) (Invitrogen) and Silencer Predesigned siRNA (GGCTCAGATTAGTAACATG) (Ambion) by the Oligofectamine method (Invitrogen) according to the manufacturer's instructions as previously described.

Co-expression of CCDC95, but not the mutant that does not bind Kir/Gem, could circumvent the requirement of importin α5 for nuclear localization of Kir/Gem W269G (FIG. 5C, and FIG. 10, panels c and d). Thus, even in the absence of the importin α5, nuclear transport of Kir/Gem can occur via CCDC95 and importins α6 and α7, suggesting a role for CCDC95 as a chaperone for nuclear import of the small GTP-binding protein. Immunochemisty was conducted as previously described here.

CCDC95 expression and Kir/Gem subcellular distribution are regulated during muscle differentiation The exclusive expression of CCDC95 in muscle and its ability to regulate the subcellular distribution of Kir/Gem, prompted us to analyze the endogenous expression of these proteins during muscle development. First, we used mouse embryonic stem (ES) cells, which can be differentiated into cardiomyocytes in culture and are widely used to study early events in heart development (Parisi et al., 2003). In this system, the expression of cardiomyocyte markers is first detected 7 days after the induction of differentiation (Parisi et al., 2003). Interestingly, CCDC95 expression was induced in a similar time frame and detected in a localized region of 7 day old embryoid bodies (FIG. 6A, panel c-c', d-d'). Analysis of newborn mice between postnatal day 1 and day 10 revealed that CCDC95 was already expressed in heart muscle (FIG. 6B), showing a similar subcellular localization as in adult cadiomyocytes (see FIG. 1). Immunochemisty was conducted as previously described here.

For quantification of the subcellular localizations, 100-150 randomly chosen cells from 3-5 independent experiments were analyzed and the localization of Kir/Gem grouped into different categories (no, partial or complete nuclear exclusion). H9c2 cardiomyocytes undergo differentiation into multinucleated myotubes following serum withdrawal (Pagano et al., 2004). Since undifferentiated H9c2 cells did not express CCDC95 (FIG. 6C, panel a and a'), we determined if similar to ES cells CCDC95 expression was induced upon differentiation. Indeed, after 7 days of serum deprivation, CCDC95 was coexpressed in multinucleated cells together with the muscle specific markers myogenin and troponin T (FIG. 6C, panel b' and c'). CCDC95 was present in striations in the cytoplasm as well as in a few nuclei, confirming its dual localization. Interestingly, CCDC95 containing nuclei in general showed reduced myogenin staining and, reminiscent of nuclei in apoptotic cells, their chromatin either appeared fragmented or was absent (FIG. 6C, panels b" and c"). Different stages of chromatin fragmentation and loss are shown in FIG. 11a.

To further establish the nature of the CCDC95 positive nuclear remnants, we analyzed the expression of additional markers. In contrast to the loss of myogenin (see FIGS. 6C and 6D, panel b'), MyoD, the primary myogenic regulatory factor (Parker et al., 2003; Taylor, 2002), was enriched in these structures and in CCDC95 positive myotubes in general (FIG. 6D, panel a'). Staining for α-tubulin established that the nuclear remnants were embedded in the microtubule network of the myotubes (FIG. 6D, panel c', arrows) and not associated with apoptotic cells lying on the myotubes. Thus, CCDC95 and MyoD appear to mark nuclear remnants devoid of chromatin formed following myotube differentiation. Apoptotic activity in these remnants was further established by the presence of activated caspase 3 (data not shown).

To confirm the induction of CCDC95 expression during muscle differentiation in yet another system, we took advantage of the activation of a myogenic differentiation program following exogenous expression of MyoD in NIH3T3 fibroblast cells (Qin et al., 2007). Indeed, expression of the muscle marker troponin T as well as CCDC95 was restricted to cells overexpressing MyoD (FIG. 6E and FIG. 11b). This suggests that expression of CCDC95 is directly or indirectly regulated by MyoD.

In summary, expression of CCDC95 is induced during muscle differentiation and displays a dual localization in myotubes to cytoplasmic striations and apoptotic nuclear remnants.

Given its interaction with Rho kinase, a possible mechanism by which Kir/Gem may be exerting its function during myogenesis is through the Rho pathway. While conflicting, Rho and Rho kinase have been implicated with both positive and negative regulatory roles in muscle development (Bryan et al., 2005; Pelosi et al., 2007). Since the subcellular localization of Kir/Gem varies during muscle development. it may only inhibit Rho kinase when present in the cytoplasm. Thus, depending on the subcellular distribution of Kir/Gem, Rho may indeed mediate positive and negative effects at different steps during myogenesis. In particular, inhibition of Rho kinase is thought to be required prior to myoblast fusion, a stage where Kir/Gem is found in the cytosol.

The induction of CCDC95 during myoblast fusion correlated with the relocalization of Kir/Gem to nuclei in myotubes. These nuclei also contained CCDC95 and, interestingly, were either devoid of chromatin, or their chromatin appeared fragmented. 30-40% of the myotubes contained nuclei that appeared to be at different stages of chromatin elimination and these remnant nuclei were no longer present 10 days after of differentiation. The presence of caspase-3 and myoD, both implicated in apoptosis (Fernando et al., 2002; Fimia et al., 1998), indicates that this process may account for the elimination of these nuclei. To our knowledge, it is not known if and how the number of nuclei following myoblast fusion is regulated and it will be of interest to explore a possible role of Kir/Gem and CCDC95 in this process.

Kir/Gem and CCDC95 play a coordinated role in muscle differentiation.

Given the functional interaction of CCDC95 with Kir/Gem and its ability to mediate nuclear localization of the RGK protein, we analyzed if H9c2 cells express Kir/Gem and how its expression and subcellular localization are affected during muscle differentiation. Kir/Gem was found in the nucleus of H9c2 myoblasts (FIG. 7A, panel b) and at early stages of differentiation relocalized to a more cytoplasmic distribution (FIG. 7A, panel b'). During myotube formation, the small GTP binding protein was detected in punctate structures in the cytoplasm. Interestingly, in cells where CCDC95 was already induced, Kir/Gem was prominently located to the nucleus (FIG. 7A, panel b"). At a later stage when CCDC95 was strongly induced, Kir/Gem colocalized with CCDC95 either in the remnant nuclei described above or in the cytoplasm (FIG. 7A, panel b"', white arrow). These results strongly suggest that CCDC95 may control the subcellular distribution of Kir/Gem during later stages of muscle differentiation. Immunochemisty was conducted as previously described here.

To obtain insights into the role of the two proteins in muscle differentiation, we first overexpressed Kir/Gem and CCDC95 individually in H9c2 cells and monitored myoblasts differentiation based on the induction of troponin T (FIG. 7B) and myogenin (FIG. 12 a) expression. While overexpressed CCDC95 was present in the nucleus of multinucleated myotubes (FIGS. 7B and 12a, panel c-c'"), Kir/Gem (FIG. 7B and 12a, panel a-a") overexpressing cells failed to differentiate and form myotubes. Kir/Gem S22A/S288A/W269G, a mutant that localizes to the nucleus (Béguin et al., 2005b), only showed a partial effect (FIGS. 7B and 12a, panel b-b"), indicating that the Kir/Gem-mediated inhibition is dependent on its subcellular localization. Importantly, concomitant overexpression of Kir/Gem and CCDC95 also partially restored myoblast differentiation (FIGS. 7B and 12a, panel d-d"), suggesting that CCDC95 mediated nuclear localization of Kir/Gem abrogates its inhibitory effect. As a control, the CCDC95 mutant that does not bind Kir/Gem did not prevent the Kir/Gem-mediated inhibition of myotube formation (FIGS. 7B and 12a, panel e-e'"). Interestingly, in contrast to Kir/Gem, overexpression of Rad, Rem or Rem2 did not affect myotube formation (FIG. 7D and FIG. 12b).

For quantification of cells undergoing muscle differentiation after Kir/Gem overexpression, 100-150 randomly chosen cells from 5-7 independent experiments were analyzed. The number of cells was normalized to the efficiency of muscle differentiation (i.e. troponin T and myogenin expression) after β-galactosidase overexpression. Of the cells expressing muscle specific markers, 50% were multinucleated for control cells and cells expressing Kir/Gem S22A/S288A/W269G (db/W269G), 35%±5 for the cells coexpressing WT Kir/Gem and CCDC95.

Muscle differentiation is a tightly orchestrated process that involves the execution of regulated gene expression program leading to the fusion of myoblast into multinucleated myotubes. The identification of the novel muscle specific protein CCDC95 as a specific modulator of Kir/Gem and the implication of Kir/Gem in muscle development will allow further insight into the mechanism of this multilayered and complex process.

In conclusion, these results reveal a novel role for Kir/Gem in muscle differentiation, which is not shared by the other RGK family members. This function is dependent on the subcellular localization of Kir/Gem and regulated by CCDC95.

Statistical significance of the combined independent experiments was assessed using unpaired Student's t-tests.

C2C12 myoblast cells were transformed to either stably express a non-targeting interfering RNA, labeled as control or two distinct CCDC95 interfering RNA's to silence CCDC95 expression (FIG. 14). The first interfering RNA being Origene TI100126: AAGATGCCTCCACATACAATCCTGAGCAC (SEQ ID NO. 7, shRNA#1) and the second interfering RNA being Origene TI100128: GATCGACTTCTGCAGTATGAGAACGTGGA (SEQ ID NO. 8, shRNA#2). The transformed cells were allowed to differentiate into myotubes for 5 days. The number of myotubes per field was then determined and plotted. When the mock transfected cells or cells transfected with a non-targeting control interfering RNA are compared to the transfected cells expressing the first (shRNA #1) or second (shRNA #2) CCDC95 interfering RNA, the cells transfected with the CCDC95 interfering RNA show a greatly reduced potential to differentiate into myotubes (FIG. 14). Down-regulating CCDC95 expression with interfering RNA can be used to reduce myotube differentiation and allow the study of myoblasts.

While the invention has been described with reference to specific methods and embodiments, it will be appreciated that various modifications and changes may be made without departing from the invention.

The invention claimed is:

1. A method of inhibiting transport of an RGK protein to a nucleus comprising administering an antibody capable of binding selectively to the amino acid sequence set out in SEQ ID NO: 2, or SEQ ID NO: 4, or SEQ ID NO: 6 or a fragment thereof having a N-terminus coiled-coil domain interactable with the RGK protein thereby varying a concentration or subcellular location of a CCDC95 polypeptide comprising the amino acid sequence set out in SEQ ID NO: 2, or SEQ ID NO: 4, or SEQ ID NO: 6 or a fragment thereof.

2. The method of claim 1 wherein the RGK protein comprises Kir/Gem.

3. The method of claim 1 wherein the antibody is administered to a myoblast in vitro, thereby inhibiting the formation of a myotube.

4. A method of inhibiting sub-cellular location of a concentration of an RGK protein to a nucleus comprising the step of administering an antibody capable of binding selectively to the amino acid sequence set out in SEQ ID NO: 2, or SEQ ID NO: 4, or SEQ ID NO: 6 or a fragment thereof having a N-terminus coiled-coil domain interactable with the RGK protein thereby varying a concentration of CCDC95 polypeptide comprising the amino acid sequence set out in SEQ ID NO: 2, or SEQ ID NO: 4, or SEQ ID NO: 6 or a fragment thereof.

* * * * *